US009084896B2

(12) United States Patent
Kokones et al.

(10) Patent No.: US 9,084,896 B2
(45) Date of Patent: Jul. 21, 2015

(54) CLINICIAN PROGRAMMER SYSTEM AND METHOD FOR STEERING VOLUMES OF ACTIVATION

(75) Inventors: Scott Kokones, Boston, MA (US); David Arthur Blum, Boston, MA (US); Keith Carlton, Boston, MA (US); Troy Sparks, Woodbury, MN (US)

(73) Assignee: Intelect Medical, Inc., Cleveland, OH (US)

( * ) Notice: Subject to any disclaimer, the term of this patent is extended or adjusted under 35 U.S.C. 154(b) by 0 days.

(21) Appl. No.: 13/534,700

(22) Filed: Jun. 27, 2012

(65) Prior Publication Data

US 2012/0271376 A1    Oct. 25, 2012

Related U.S. Application Data

(62) Division of application No. 12/454,340, filed on May 15, 2009.

(60) Provisional application No. 61/053,449, filed on May 15, 2008, provisional application No. 61/055,398, (Continued)

(51) Int. Cl.
*A61N 1/00* (2006.01)
*A61N 1/36* (2006.01)
(Continued)

(52) U.S. Cl.
CPC ........ *A61N 1/36128* (2013.01); *G06F 19/3437* (2013.01); *G06K 9/00885* (2013.01);
(Continued)

(58) Field of Classification Search
CPC ........... A61N 1/36128; A61N 1/36082; A61N 1/37247; A61N 1/36185; G06K 9/00885; G06F 19/3437; G06F 19/3406

USPC .......................................... 607/45, 46, 30, 59
See application file for complete search history.

(56) References Cited

U.S. PATENT DOCUMENTS 5,099,846 A    3/1992  Hardy
5,361,763 A   11/1994  Kao et al.
(Continued)

FOREIGN PATENT DOCUMENTS

WO    2001/90876 A1    11/2001
WO    2004/019799 A2    3/2004
(Continued)

OTHER PUBLICATIONS

Butson et al., "Current Steering to Control the Volume of Tissue Activated During Deep Brain Stimulation," Brain Stimulation 1, 2008, pp. 7-15.
(Continued)

*Primary Examiner* — Michael Kahelin
*Assistant Examiner* — Mallika D Fairchild
(74) *Attorney, Agent, or Firm* — Lowe Graham Jones PLLC; Bruce E. Black

(57) ABSTRACT

A system and method for selection of stimulation parameters for Deep Brain Stimulation (DBS) may include a processor that displays in a display device and in relation to a displayed model of a leadwire including model electrodes, a current field corresponding to a first stimulation parameter set, provides a user interface for receipt of user input representing a shift of the current field, in response to the user input, moves, in the display device, the current field with respect to the displayed model, determines a second stimulation parameter set that results in the moved current field, and outputs the second stimulation parameter set and/or sets a stimulation device with the second stimulation parameter set, where the stimulation device is configured for performing a stimulation using the leadwire in accordance with the second stimulation parameter set.

25 Claims, 34 Drawing Sheets

Related U.S. Application Data filed on May 22, 2008, provisional application No. 61/079,362, filed on Jul. 9, 2008, provisional application No. 61/111,523, filed on Nov. 5, 2008, provisional application No. 61/113,927, filed on Nov. 12, 2008, provisional application No. 61/201,037, filed on Dec. 4, 2008.

(51) Int. Cl.
*G06K 9/00* (2006.01)
*A61N 1/372* (2006.01)
*G06F 19/00* (2011.01)

(52) U.S. Cl.
CPC .......... *A61N1/36082* (2013.01); *A61N 1/36185* (2013.01); *A61N 1/37247* (2013.01); *G06F 19/3406* (2013.01)

(56) References Cited

U.S. PATENT DOCUMENTS

| | | |
|---|---|---|
| 5,452,407 A | 9/1995 | Crook |
| 5,724,985 A | 3/1998 | Snell et al. |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,826,902 B2 | 11/2010 | Stone et al. |
| 7,848,802 B2 | 12/2010 | Goetz et al. |
| 8,180,601 B2 | 5/2012 | Butson et al. |
| 8,452,415 B2 | 5/2013 | Goetz et al. |
| 2004/0034394 A1 | 2/2004 | Woods et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0171587 A1 | 8/2005 | Daglow et al. |
| 2005/0228250 A1* | 10/2005 | Bitter et al. .................. 600/407 |
| 2006/0017749 A1 | 1/2006 | McIntyre et al. |
| 2006/0020292 A1 | 1/2006 | Goetz et al. |
| 2006/0094951 A1 | 5/2006 | Dean et al. |
| 2006/0235472 A1 | 10/2006 | Goetz et al. |
| 2006/0259079 A1 | 11/2006 | King |
| 2007/0017749 A1 | 1/2007 | Dold et al. |
| 2007/0043268 A1 | 2/2007 | Russell |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203537 A1* | 8/2007 | Goetz et al. .................. 607/59 |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1* | 8/2007 | Stone et al. .................. 607/59 |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0123923 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |

(56) References Cited

U.S. PATENT DOCUMENTS

| | | |
|---|---|---|
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0204192 A1 | 8/2009 | Carlton et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0023130 A1 | 1/2010 | Henry et al. |
| 2010/0049276 A1 | 2/2010 | Blum et al. |
| 2010/0049280 A1 | 2/2010 | Goetz |
| 2011/0191275 A1 | 8/2011 | Lujan et al. |

FOREIGN PATENT DOCUMENTS

| | | |
|---|---|---|
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2010/120823 A2 | 10/2010 |
| WO | 2011/139779 A1 | 11/2011 |
| WO | 2011/159688 A2 | 12/2011 |

OTHER PUBLICATIONS

Butson et al., "Patient-Specific Analysis of the Volume of Tissue Activated During Deep Brain Stimulation," Neuroimage 34, 2007, pp. 661-670.

Butson et al., "Role of Electrode Design on the Volume of Tissue Activated During Deep Brain Stimulation," Journal of Neural Engineering, Mar. 1, 2006, vol. 3, No. 1, pp. 1-8.

Butson et al., "StimExplorer: Deep Brain Stimulation Parameter Selection Software System," Acta Neurochirugica, Jan. 1, 2007, vol. 97, No. 2, pp. 569-574.

Miocinovic et al. ,"Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al., "Sketching and Composing Widgets for 3D Manipulation," Eurographics, Apr. 2008, vol. 27, No. 2, pp. 301-310.

PCT Search Report from PCT/US09/03017, dated Aug. 3, 2009.
PCT Search Report from PCT/US09/03038, dated Oct. 8, 2009.
PCT Search Report from PCT/US09/03040, dated Aug. 13, 2009.
PCT Search Report from PCT/US09/03041, dated Aug. 20, 2009.
PCT Search Report from PCT/US09/03049, dated Jan. 26, 2010.

Izad, Olivier, "Computationally Efficient Method in Predicating Axonal Excitation," Dissertation for Masters Degree, Department of Biomedical Engineering, Case Western Reserve University, May 2009, 144 pages.

Jaccard, Paul, "Étude comparative de la distribution florale dans une portion odes Aples et des Jura," Bulletin de la SociétéVaudoise des Sciences Naturelles (1901), vol. 37, pp. 547-579.

Dice, Lee R., "Measures of the Amount of Ecologic Association Between Species," Ecology 26(3) (1945), pp. 297-302. doi:10.2307/1932409, http://jstor.org/stable/1932409.

Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.

Hubert, Lawrence et al., "Comparing partitions," Journal of Classification 2(1) (1985), pp. 193-218, doi:10.1007/BF01908075.

Cover, T.M. et al., "Elements of information theory," (1991) John Wiley & Sons, New York, NY, pp. 1-542.

Meila, Marina, "Comparing Clusterings by the Variation of Information," Learning Theory and Kernel Machines (2003), pp. 173-187.

European Patent Office, International Search Report in International Application No. PCT/US2012/053344, dated Nov. 26, 2012, 8 pages.

European Patent Office, International Search Report in International Application No. PCT/US2012/050181, dated Jan. 3, 2013, 7 pages.

Euopean Patent Office, International Search Report and the Written Opinion in International Application No. PCT/US2012/050170, dated Oct. 5, 2012, 15 pages.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al, "Fast and robust multi-atlas segmentation of brain magnetic resonance images," NeuroImage, Academic Press, vol. 49, No. 3, Feb. 1, 2010, pp. 2352-2365.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

European Patent Office, partial International Search Report in International Application No. PCT/US2012/030701, dated Feb. 15, 2013, 7 pages.

European Patent Office, partial International Search Report in International Application No. PCT/US2012/030705, dated Mar. 6, 2013, 7 pages.

European Patent Office, International Search Report and Written Opinion in International Application No. PCT/US2012/030700, dated Feb. 27, 2013, 9 pages.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

European Patent Office, International Search report and Written Opinion in PCT application No. PCT/US12/050174, dated Mar. 6, 2013, 20 pages.

European Patent Office, International Search Report and Written Opinion in International Application No. PCT/US2012/050187, dated Feb. 27, 2013, 9 pages.

European Patent Office, International Search Report and the Written Opinion of the International Searching Authority in International Application No. PCT/US2012/050175, dated Oct. 26, 2012, 15 pages.

* cited by examiner

FIG. 11

DIRECTIONAL LEAD WITH 4 CONTACTS LOCATED CIRCUMFERENTIALLY AROUND THE DIAMETER.

CROSS SECTIONAL VIEW OF A DIRECTIONAL ELECTRODE

GRADUAL SHIFT OF THE STIMULATION FIELD ABOUT THE X AXIS BASED
ON A DIRECTIONAL INPUT

TRANSPOSING OF THE STIMULATION FIELD IN THE X AXIS, ABOUT THE
Y AXIS BASED ON A DIRECTIONAL INPUT

SMOOTH STEERING OF THE STIMULATION FIELD BASED ON A ROTATIONAL INPUT

CUBE WITH DIRECTIONAL INPUTS

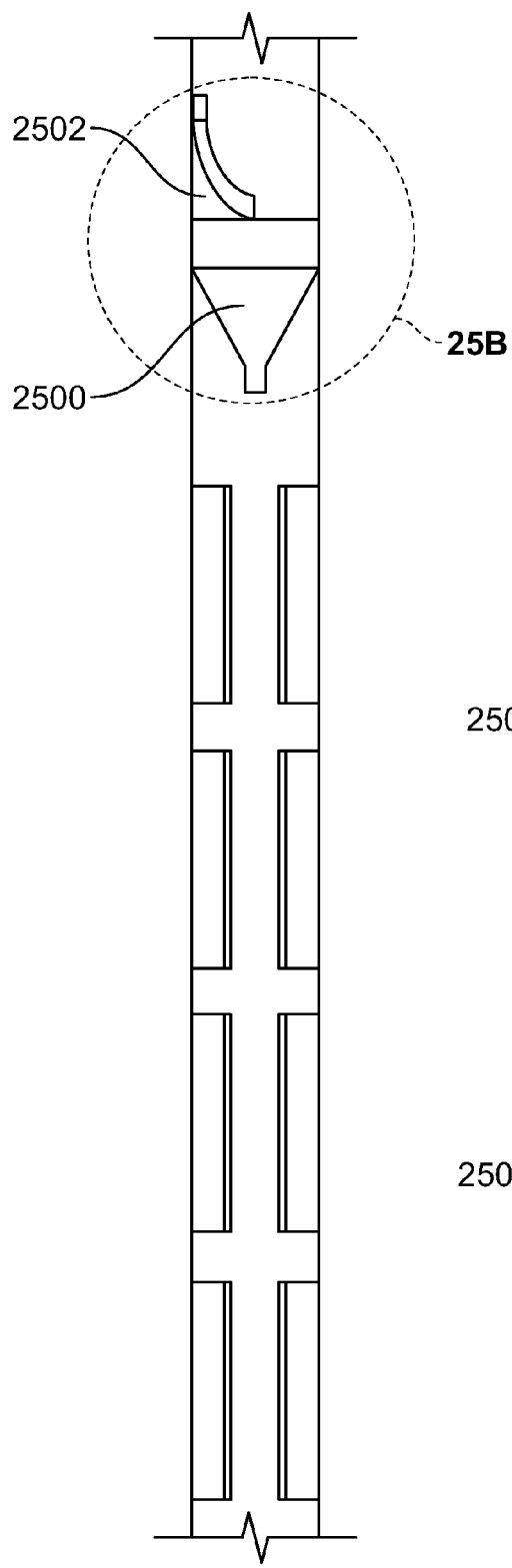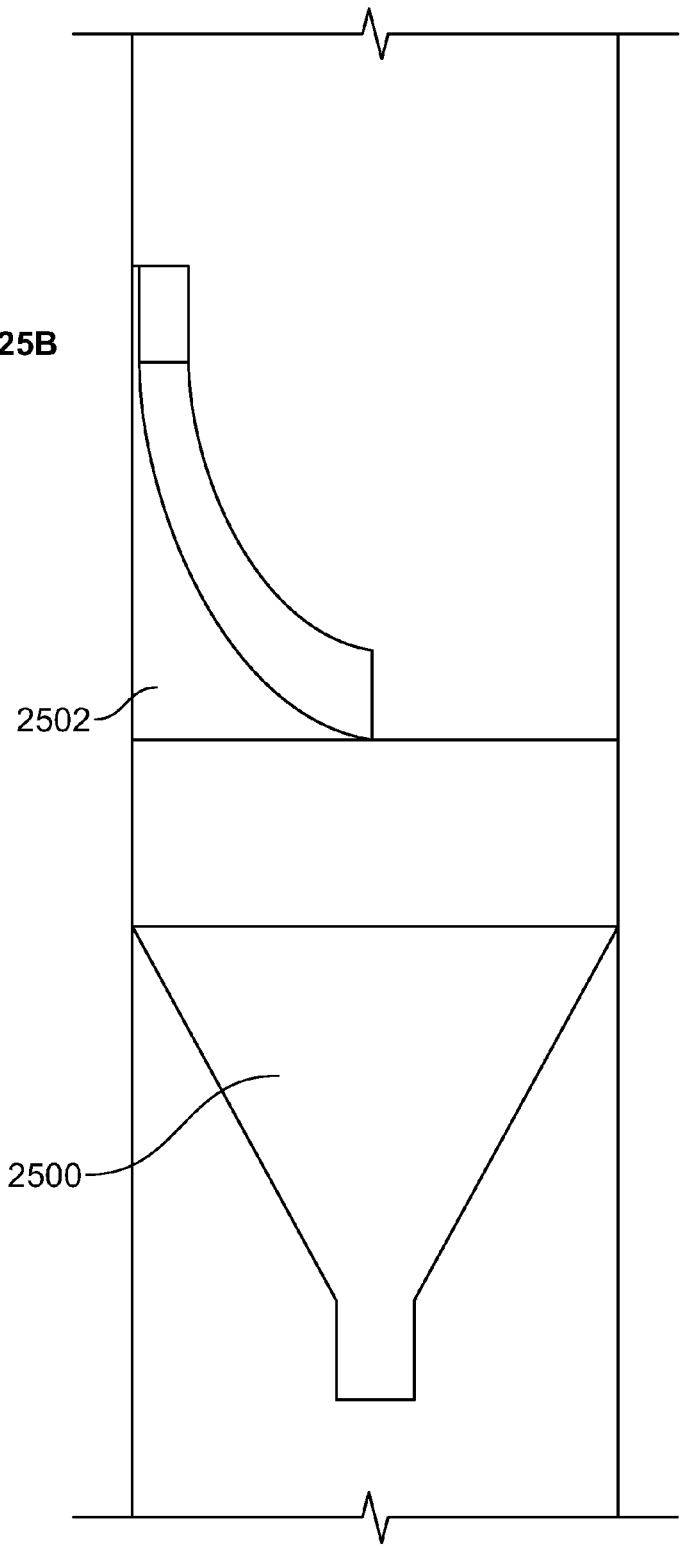
FIG. 25A  FIG. 25B

CLINICIAN PROGRAMMER SYSTEM AND METHOD FOR STEERING VOLUMES OF ACTIVATION

CROSS-REFERENCE TO RELATED APPLICATIONS

This application is a divisional of U.S. patent application Ser. No. 12/454,340, filed May 15, 2009, which claims priority to U.S. Provisional Patent Application Ser. No. 61/053,449, filed May 15, 2008, U.S. Provisional Patent Application Ser. No. 61/055,398, filed May 22, 2008, U.S. Provisional Patent Application Ser. No. 61/079,362, filed Jul. 9, 2008, U.S. Provisional Patent Application Ser. No. 61/111,523, filed Nov. 5, 2008, U.S. Provisional Patent Application Ser. No. 61/113,927, filed Nov. 12, 2008, and U.S. Provisional Patent Application Ser. No. 61/201,037, filed Dec. 4, 2008, the disclosures of all of which are herein incorporated by reference in their entireties.

FIELD OF THE INVENTION

The present invention relates to a 3-D programming environment, e.g., usable for an electrical stimulation system for one or more physiologic areas, such as neural, cardiac or one or more other areas of a mammalian body, such as a human or other animal.

BACKGROUND

Deep brain stimulation (DBS), such as of the thalamus or basal ganglia, is a clinical technique for the treatment of disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder. However, understanding of the therapeutic mechanisms of action remains elusive. The stimulation parameters, electrode geometries, or electrode locations that are best suited for existing or future uses of DBS also are unclear.

A DBS procedure typically involves first obtaining preoperative images of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, such as the STEALTHSTATION® from the Surgical Navigation Technologies, Inc. (SNT) subsidiary of Medtronic, Inc., for example. Using the preoperative images being displayed on the IGS workstation, a neurosurgeon can select a target region within the brain, an entry point on the patient's skull, and a desired trajectory between the entry point and the target region. The entry point and trajectory are typically carefully selected to avoid intersecting or otherwise damaging certain nearby critical brain structures or vasculature.

In the operating room, the patient is immobilized and the patient's actual physical position is registered to the preoperative images displayed on the IGS workstation, such as by using a remotely detectable IGS wand. In one example, the physician marks the entry point on the patient's skull, drills a burr hole at that location, and affixes a trajectory guide device about the burr hole. The trajectory guide device includes a bore that can be aimed using the IGS wand to obtain the desired trajectory to the target region. After aiming, the trajectory guide is locked to preserve the aimed trajectory toward the target region.

After the aimed trajectory has been locked in using the trajectory guide, a microdrive introducer is used to insert the surgical instrument along the trajectory toward the target region of the brain. The surgical instrument may include, among other things, a recording electrode leadwire, for recording intrinsic electrical brain signals; a stimulation electrode leadwire, for providing electrical energy to the target region of the brain; or associated auxiliary guidewires or guide catheters for steering a primary instrument toward the target region of the brain.

The recording electrode leadwire is typically used first to confirm, by interpreting the intrinsic electrical brain signals, that a particular location along the trajectory is indeed the desired target region of the brain. The stimulation electrode leadwire, which typically includes multiple closely-spaced electrically independent stimulation electrode contacts, is then introduced to deliver the therapeutic DBS to the target region of the brain. The stimulation electrode leadwire is then immobilized, such as by using an instrument immobilization device located at the burr hole entry in the patient's skull, in order for the DBS therapy to be subsequently performed.

The subthalamic nucleus (STN) represents the most common target for DBS technology. Clinically effective STN DBS for PD has typically used electrode contacts in the anterior-dorsal STN. However, STN DBS exhibits a low threshold for certain undesirable side effects, such as tetanic muscle contraction, speech disturbance and ocular deviation. Highly anisotropic fiber tracks are located about the STN. Such nerve tracks exhibit high electrical conductivity in a particular direction. Activation of these tracks has been implicated in many of the DBS side effects. However, there exists a limited understanding of the neural response to DBS. The three-dimensional (3-D) tissue medium near the DBS electrode typically includes both inhomogeneous and anisotropic characteristics. Such complexity makes it difficult to predict the particular volume of tissue influenced by DBS.

After the immobilization of the stimulation electrode leadwire, the actual DBS therapy is often not initiated until after a time period of about two-weeks to one month has elapsed. This is due primarily to the acute reaction of the brain tissue to the introduced DBS electrode leadwire (e.g., the formation of adjacent scar tissue), and stabilization of the patient's disease symptoms. At that time, a particular one or more of the stimulation electrode contacts is selected for delivering the therapeutic DBS, and other DBS parameters are adjusted to achieve an acceptable level of therapeutic benefit.

SUMMARY

Parameter selections for DBS and other forms of neuromodulation (central nervous system and peripheral nervous system) are typically currently achieved via arbitrary trial-and-error, without visual aids of the electrode location in the tissue medium or computational models of the volume of tissue influenced by the stimulation.

A treating physician typically would like to tailor the DBS parameters (such as which one or more of the stimulating electrode contacts to use, the stimulation pulse amplitude, the stimulation pulse width, and/or the stimulation frequency) for a particular patient to improve the effectiveness of the DBS therapy. This is a complex problem because there are several different DBS parameters than can be varied. Because selecting a particular DBS electrode contact and parameter combination setting is typically a trial-and-error process, it is difficult and time-consuming and, therefore, expensive. Moreover, it may not necessarily result in the best possible therapy or in avoiding the above-mentioned undesirable side effects. Therefore, there is a need to provide help to speed or otherwise improve this DBS parameter selection process or to otherwise enhance DBS techniques. Additionally, there is a need for a better interface via which to control the electrode selections and values.

Example embodiments of the present invention provide a system and methods for efficient parameter selection. The system and methods may produce visual aids that help in a DBS parameter selection process. In an example embodiment of the present invention, a system and method determines a Stimulation Field Model (SFM) representing a volume of tissue likely to be stimulated by input stimulation parameters of the DBS electrode(s). The SFM is also referred to as a Volume of Influence (VOI), Volume of Activation (VOA), or Volume of Tissue Activated (VTA). The VOA may be based on voltages of an Electrical Stimulation Field (ESF).

In an example embodiment, the VOA is calculated for a monopolar electrode leadwire, where the current source is from one or more contacts on the DBS electrode leadwire and the ground is at a casing of an Implantable Pulse Generator (IPG) located some distance from the DBS leadwire. In another example embodiment, the VOA is calculated for a bipolar electrode leadwire, where the current source is from one or more contacts on the DBS electrode leadwire and the ground is at another one or more contacts of the DBS electrode leadwire.

In an example embodiment of the present invention, a system and method may determine an optimal DBS parameter set for a desired VOA.

In an example embodiment of the present invention, a system and method may provide a graphical user interface (GUI) display on a user interface machine in which a user may view the generated VOAs. The user may set various DBS parameter combinations and view the predicted VOAs, so that the user can use the information to decide which parameters to set during the brain stimulation. The display may illustrate, for example, a VOA and anatomical structures, and their overlap, for example as described in U.S. Provisional Patent Application Ser. No. 61/079,362, filed Jul. 9, 2008, which is incorporated herein by reference. The user may thereby determine whether an anatomical structure intended to be activated is activated in a displayed VOA and/or whether anatomical structures for which activation is detrimental is activated in the displayed VOA, for example, as described in U.S. Provisional Patent Application Ser. No. 61/055,398, filed May 22, 2008, which is incorporated by reference herein.

Example embodiments of the present invention provide a clinician programmer system configured to import one or more medical images of a patient (e.g., MRI image, CT image, or other medical image or scan); to use the one or more medical images to create a patient brain anatomy (e.g., fitting the medical image to a pre-loaded brain anatomy, such as by using a best-fit technique); to display a 3-dimensional (3-D) rendition of one or more substructures of the patient's brain; to obtain microelectrode recording (MER) data and incorporate the MER data into the 3-D rendition of the one or more substructures of the patient's brain; to predict one or more programming settings; to show a side effect of the one or more programming settings; to define a desired VOA (e.g., define the desired VOA on the 3-D rendition of the one or more substructures of the patient's brain); to define programming settings using the desired VOA defined on the 3-D rendition of the one or more substructures of the patient's brain; to obtain information from one or more sensors located in the clinician programmer system or other system components (e.g., an implantable medical device (IMD), an IPG, a patient programmer module, a leadwire, an extension, or a burr-hole cap); to receive electroencephalography (EEG) information; to receive video information; to analyze received information; and/or to store information for clinician review.

In an example embodiment, the clinician programmer system is configured to program an IMD, such as an IPG DBS, or other patient application or therapy. In an example embodiment, a system can include a clinician programmer or a therapy delivery module, the clinician programmer module optionally including at least one of a viewer/navigator or programming software.

In an example embodiment of the present invention, a method includes: receiving a stimulation parameter; calculating a VOA using the stimulation parameter and a model electrode leadwire including a plurality of model electrode leadwire contacts; displaying the electrical stimulation field in relation to the model electrode leadwire; adjusting, in response to a user input, the VOA; and displaying the adjusted VOA.

In a further example embodiment of the method: the adjusting in response to the user input includes adjusting in response to at least one of a directional user input and an amplitude user input; the directional user input includes at least one input related to moving the VOA with respect to the model electrode leadwire or altering the shape of the VOA; and the amplitude user input includes at least one of adjusting the amplitude of the stimulation and adjusting a size of the VOA.

In an example embodiment of the present invention, a method includes: delivering an electrical stimulation; calculating a VOA; receiving at least one of a benefit and a side effect from the electrical stimulation; registering at least one of the side effect and the benefit with the VOA; and displaying at least one of the side effect and the benefit with respect to the VOA. The at least one of the side effect and the benefit may be received as user input via a user interface of the system. For example, the physician may observe and enter into the system certain benefits and/or side effects resulting from a stimulation using a certain set of stimulation parameters.

An example embodiment of the present invention is directed to a processor, which may be implemented using any conventional processing circuit and device or combination thereof, e.g., a Central Processing Unit (CPU) of a Personal Computer (PC) or other workstation processor, to execute code provided, e.g., on a hardware-implemented computer-readable medium including any conventional memory device, to perform any of the methods described herein, alone or in combination. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware-implemented computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 11-12 illustrate example screenshots of system output for patient history functions.

FIGS. 25A-B illustrate a 2 triangle concept for directional leadwire location, according to an example embodiment of the present invention.

DETAILED DESCRIPTION

System Components

Figure 2:
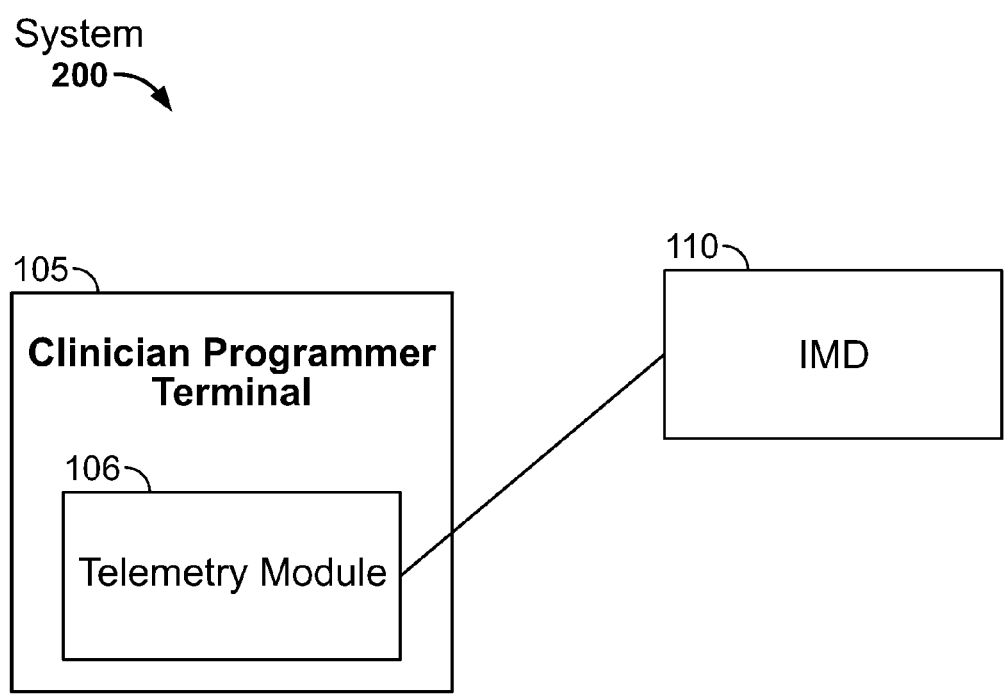
FIG. 2 illustrates generally an example of a system including a clinician programmer and an implantable medical device (IMD).

FIG. 2 illustrates generally an example of a system 200 including a clinician programmer terminal 105. The clinician programmer terminal 105 includes any suitably appropriate computing device or combination of computing devices, a non-exhaustive list of which includes a desktop computer or other workstation, a laptop, notebook computer, tablet PC, and handheld. The clinician programmer terminal 105 can include any device configured to send, receive, analyze, compute, and/or display information.

In an example, the clinician programmer terminal 105 may include a memory device and a processor. The memory device may be configured to store, and the processor may be configured to run, software, such as clinician programming software. The memory device may also be used for storing various information as described in detail below.

Method examples described herein can be machine or computer-implemented at least in part. Some examples can include a computer-readable medium or machine-readable medium encoded with instructions operable to configure an electronic device to perform methods as described herein. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, RAM, ROM, and the like.

As shown in FIG. 2, the clinician programmer terminal 105 may be coupled (e.g., wirelessly, directly, etc.) to an IMD 110. For example, the clinician programmer terminal 105 may include a telemetry module 106. The telemetry module may be configured for wireless, electrical, optical, or other telemetry. In an example embodiment, the telemetry module 106 may include a universal serial bus (USB) dongle that attaches to the clinician programmer terminal 105 (e.g., used to communicate with the IMD 110).

In an example embodiment, the IMD 110 may include an IPG, various implantable sensors, or other implantable energy delivery circuits. In other examples, the clinician programmer terminal 105 may include or can be communicatively coupled to other external devices, such as an external pulse generator (EPG), a patient programmer device, etc.

In example embodiments of the present invention, the clinician programmer system may include one or more of the following: password protection; data storage capabilities including storage and use of patient, physician, and device information, diagnostic tracking, usage statistics, storage and usage of therapy information, user access, and printable data recovery; support of IPG/EPG/PP capabilities; foreign language support; 3-D visualization of stimulation field including capabilities for importing MRI/CT scans, a module(s) for automatically merging scans and allowing a user to manually verify, capabilities for locating frame fiducials, an interface for manual selection of Anterior Commissure (AC)-Posterior Commissure (PC), a 3-D stretchable/deformable atlas of the thalamus with defined substructures, basal ganglia and cerebellum, input MER tracks, translation of 3-D structures based on MER, placement of leadwire including x, y, z, arc, ring, and rotation; an interface for entering parameter data and capabilities for stretching the stimulation field; support for logging or displaying calculated VOAs; and interpolation between different VOAs including linear or nonlinear, stored gradient fields, and choosing an isosurface on gradient.

Programmer Overview

Figure 4:
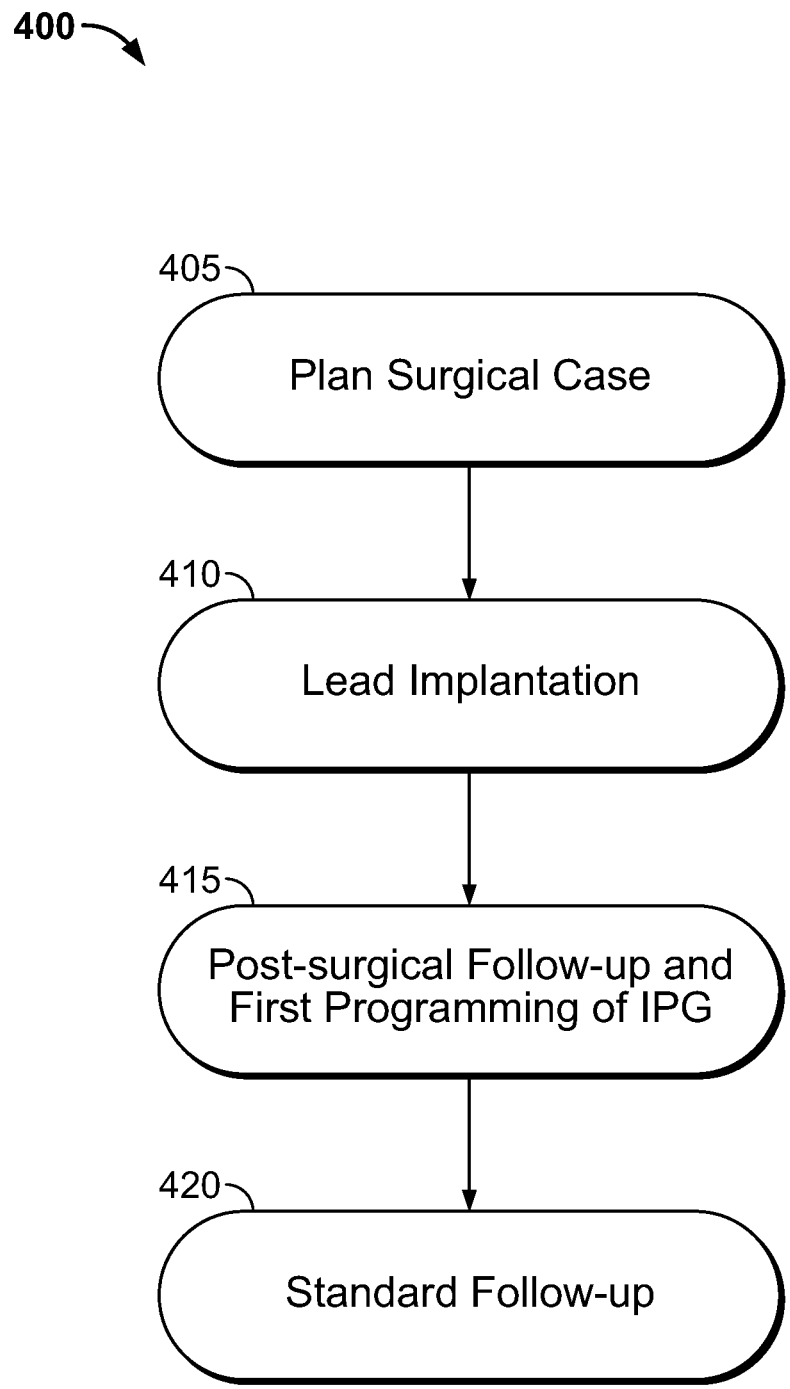
FIG. 4 illustrates generally an example of a method including a providing a standard follow-up.

FIG. 4 illustrates generally an example of a method 400 including planning a surgical case, implanting a leadwire, conducting post-surgical follow-up, programming the IPG, and conducting standard follow-up, according to an example embodiment of the present invention.

At step 405, the surgical case is planned. In certain examples, the surgical planning can include pre-visualizing a surgical intervention, determining the area or location for intervention (e.g., an area or a location of a brain), determining the amount of intervention (e.g., determining the electrical or other stimulation or stimulation parameters), determining or planning a method or route for intervention, etc.

In an example, surgical planning for deep brain stimulation (or other neurosurgery) can include taking, receiving, or importing one or more images (e.g., CT, MR, etc.) of the patient, including one or more possible areas of intervention. In certain example embodiments of the present invention, the system is configured to generate and display a 3-D model of one or more areas of the patient, e.g., using the one or more images, or an existing 3-D model can be adapted to fit the one or more areas of the patient, e.g., using the one or more images.

In an example, once created or adapted, the 3-D model can be used to plan a path or entry point for a proposed therapy or intervention. In certain examples, the path can be planned to avoid entrance to, disturbance of, or damage to one or more areas of the brain or surrounding tissue and vasculature, to achieve a desired efficacy, to avoid one or more predicted side effects, etc. In other examples, at least one of a stimulation parameter or the path or entry point can be planned or predicted based upon a desired intervention, stimulation, or other outcome.

At step 410, a leadwire is implanted. In an example, the leadwire can be implanted using the planned surgical case or surgical planning In an example, the leadwire can be a stimulation leadwire. In other examples, features described herein with respect to a leadwire may be applied to other intervention or therapy devices, e.g., lesioning or therapy delivery devices, implanted instead of, or in conjunction with, the stimulation leadwire.

At step 415, post-surgical follow-up is conducted and an initial programming of the IPG is conducted. Further, a stimulation therapy may be administered in accordance with therapy parameters of the initial programming. In an example, once the leadwire has been implanted, one or more medical images can be taken to evaluate the location of the leadwire. In certain examples, a 3-D model can be created, using the one or more medical images, and displayed to show the actual location of the leadwire or other implanted intervention or therapy device.

In certain examples, the actual leadwire location, path, or entry point can be compared to a planned, predicted, or desired leadwire location (e.g., the path or entry point planned during the surgical planning or the plan surgical case step 405). For example, if it is determined that the actual leadwire location is different than the planned position, a model of the leadwire relative to anatomical structures may be accordingly modified.

In an example embodiment of the present invention, once the leadwire has been implanted, a desired therapy, intervention, stimulation, or other treatment can be predicted or computed at or for the actual leadwire location. In certain examples, the leadwire can include one or more electrodes in one or more locations. In this example, the prediction or computation of the desired therapy, intervention, stimulation, or other treatment can include a prediction or computation of a direct effect (e.g., desired therapy, etc.), indirect effect (e.g., side effect, etc.), or other effect of the desired therapy, intervention, stimulation (e.g., including stimulation parameters), or other treatment at the location using the one or more electrodes or specific combinations of the one or more electrodes.

At step 420, standard follow-up is conducted. In certain examples, the standard follow-up can include further imaging, one or more tests or experiments, further programming of the IPG or EPG, analysis of recorded data, and/or follow-up medical examinations or appointments.

In an example, one or more steps of method 400 can be completed using the clinician programmer terminal 105.

Modeling

In an example embodiment of the present invention, a system includes a clinician programmer system executing a clinician programmer software module configured to import one or more medical images of a patient, such as a patient's MRI or CT scans (pre-implant or post-implant). The clinician programmer system may be configured to display the one or more medical images, e.g., using a viewer/navigator module and GUI display device coupled to the clinician programmer module.

In an example, the clinician programmer system may be configured to change or alternate between different medical images, such as different MRI or CT images or views. Further, the clinician programmer system may be configured to display different brain slices to show different sections, areas, slices, structures, or substructures of the brain or other parts of the nervous system being modeled.

In example embodiments of the present invention, the clinician programmer system is configured to create, e.g., using one or more medical images of the patient, a 3-D rendering of anatomical substructures of the brain that, in certain examples, can be overlaid over appropriate sections of the one or more medical images stored, imported, or otherwise received by the clinician programmer system. In an example, the 3-D rendering can include a scalable (e.g., stretchable or deformable) brain atlas. In an example, the stretchable or deformable atlas can include an atlas of a single brain, or a single atlas created as an average of multiple brains. Alternatively, the system may be configured to select, from a multitude of atlases, a closest match to a current patient.

Figure 27:
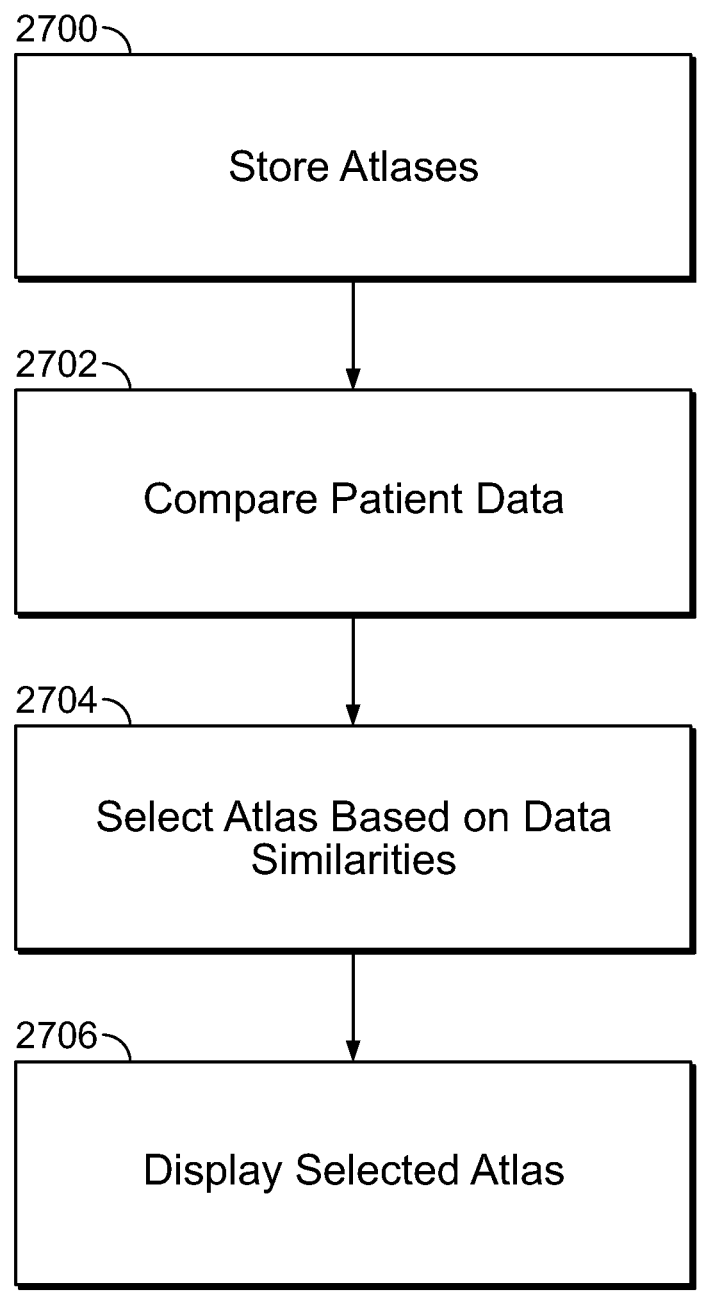
FIG. 27 is a flowchart that illustrates a method for selecting an atlas, according to an example embodiment of the present invention.

For example, as shown in FIG. 27, the system may, at step 2700, store in an atlas repository multiple 3-D atlases of individual brains (or other physiological area), e.g., corresponding to a patient population. The system may further compute and/or store in the atlas repository at step 2700 a statistical 3-D atlas constructed based on a combination of all of the stored multiple 3-D atlases. The system may further compute and/or store in the atlas repository at step 2700 statistical 3-D atlases, each constructed based on a respective combination of a subset of all of the patient population atlases.

At step 2702, the system may compare image data and/or MER data of the subject patient and the patients to whom the atlases of the atlas repository correspond. For example, MRI or other image data of the patient may be compared to image data of patients of the patient population, or MER data of the patient may be compared directly to the atlases.

At step 2704, the system may select one of the atlases from the atlas repository as a best fit atlas. The selection may be based on similarities between the image data and/or MER data determined in the comparison step 2702.

At step 2706, the system may display the selected best fit atlas, which may be further deformed automatically or manually.

The clinician programmer system can be configured to automatically co-register, scale, and/or adjust the one or more medical images (e.g., a MRI or a CT image); identify the AC, the PC, the AC/PC line, the midline, and/or other identifiable structure or landmark of the brain; calculate the mid-commissural point (MCP); and/or provide ventricle segmentation or frame fiducial identification through an algorithmic process.

For example, one or more medical images of the patient can be uploaded. Then, using the one or more uploaded medical images, the AC/PC line can be detected. In certain examples, the AC/PC line can be detected manually by a clinician. Alternatively, the system can automatically detect the AC/PC line. In an example, the AC/PC line, or other information about the AC or PC, can be coordinated or detected in relation to surgical hardware, such as a headframe or other surgical marker. Once the AC/PC line is detected, adjustments can be made to a model or brain atlas to fit the one or more medical images. In an example, the adjustments can include linear stretching to match the general shape and size of the brain as shown in the one or more medical images, and further adjustments using the detected AC/PC line. In an example, the linear adjustments can be made manually by a clinician or other user, or the linear adjustments can be made automatically using one or more image processing techniques.

In an example embodiment, once the general shape of the model or brain atlas has been met, the system is configured for receiving input to stretch or deform at least a portion of the model or brain atlas to better fit certain structures or substructures that were not closely fit using the automatic or manual linear adjustments. Alternatively or additionally, the system may be configured to perform the additional stretching or deformation of the at least a portion of the model or brain atlas.

In an example embodiment, the system is configured to control the stretching or deforming of the model or brain atlas using one or more nodes or boundaries placed throughout at least a portion of the model or brain atlas.

For example, if at least a portion of a patient's brain is abnormally shaped or different than the base model or brain atlas (e.g., if a portion of the brain has been damaged or is otherwise different from the base model or brain atlas), the at least a portion of the model or brain atlas (e.g., a structure, substructure, or other portion of the brain) can be stretched or deformed, while leaving the remainder of the model or brain atlas, or a portion of the remainder of the model or brain atlas, unchanged. In an example, this can be accomplished using one or more nodes or boundaries.

Figure 9A:
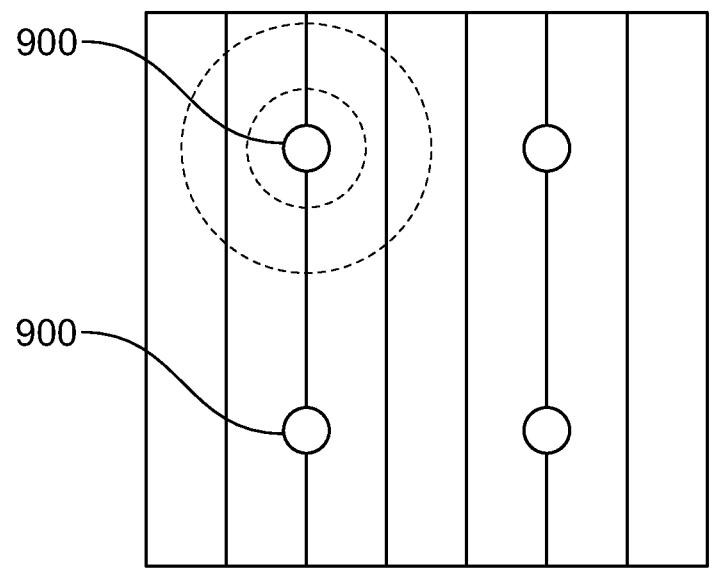
FIGS. 9A-9B illustrate generally an example of deforming an image using one or more node.
Figure 9B:
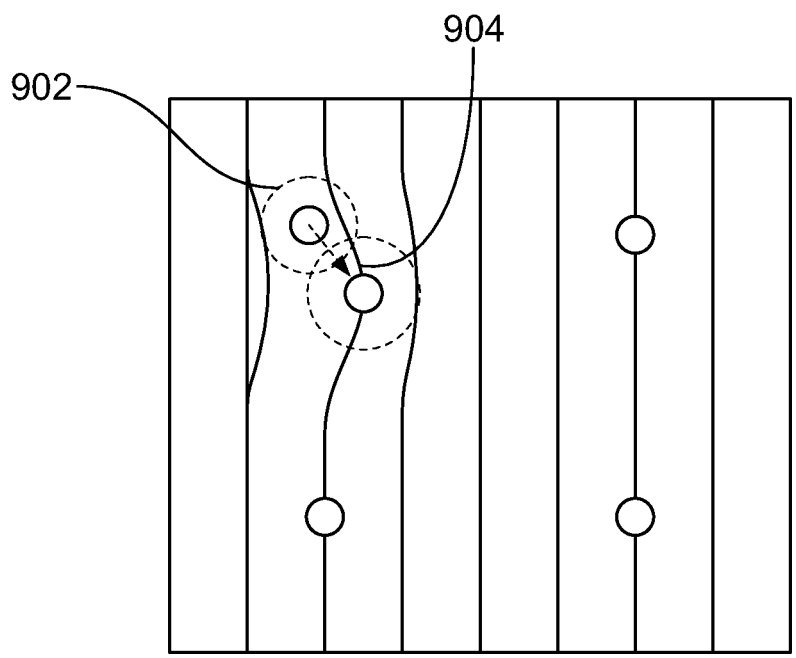

FIGS. 9A-9B illustrate generally an example of deforming an image using one or more nodes. In an example embodiment of the present invention, the system provides for one or more nodes 900 to be located on the model or brain atlas. For example, FIG. 9A shows four nodes 900. The one or more nodes 900 can be manually added by a clinician or other user, or the node 900 can be automatically placed on the model or brain atlas (e.g., a uniform distribution automatically placed across the slice or other view of the model or brain atlas). In an example, the clinician or other user can select a node 900 and move it to a location (e.g., manually, such as by dragging the node 900 with a mouse or other input device, by entering a location for the node 900 to be moved to, or by other input methods) in order to better fit the one or more medical images of the patient to the model or brain atlas. For example, FIG. 9B shows the node 900 at the top-left corner of FIG. 9A being moved from location 902 to location 904.

The system may be configured such that moving the node 900 causes the system to stretch, deform, or otherwise move the portion of the model or brain atlas immediately under or in contact with the node 900, as well as an area around the node. In certain examples, the area around the node 900 is automatically set, or the area can be manually defined (e.g., larger or smaller). In an example embodiment, the system is configured with one or more modes, where a first mode corresponds to one or more settings being in a default mode (e.g., automatic settings), and where a second mode corresponds to one or more settings being in a manual mode (e.g., clinician or other user defined settings).

In certain examples, the area that is stretched or deformed can be linearly deformed (e.g., the area closest to the node can be stretched or deformed the same amount as, or a linear amount more or less than, the area farthest from the node), or the area that is stretched or deformed can be nonlinearly deformed. Further, the amount or distribution of the magnitude of the stretching or deforming can be automatically set to a default amount, or manually set or adjusted by a clinician or other user.

Figure 10A:
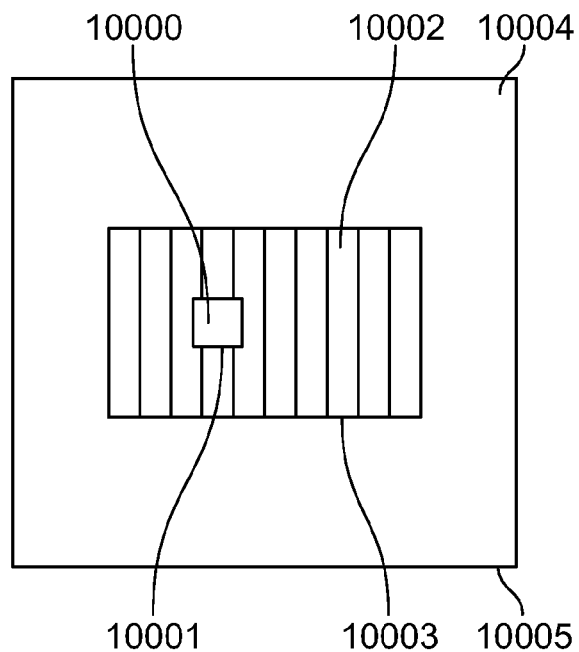
FIGS. 10A-10B illustrate generally an example of deforming an image using one or more boundary.
Figure 10B:
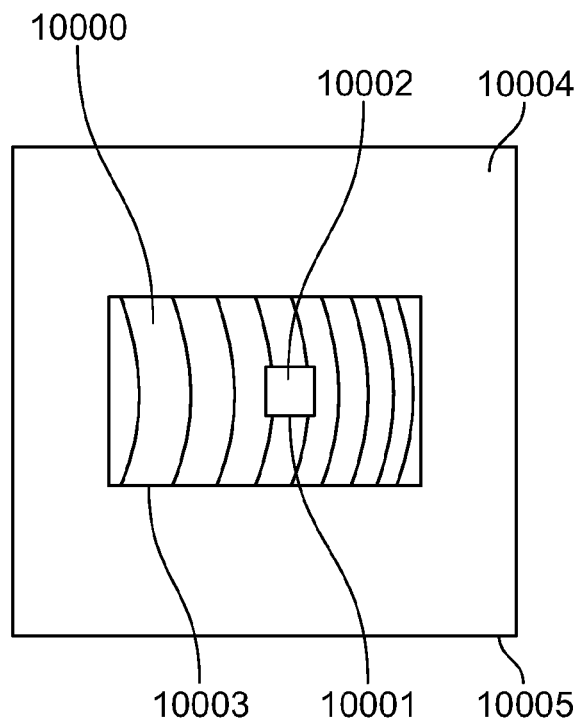

FIGS. 10A-10B illustrate generally an example of deforming an image using one or more boundaries. In an example embodiment of the present invention, one or more boundaries can be placed on the model or brain atlas. In an example, a boundary can be defined using one or more nodes, or using some other method (e.g., a dashed line, etc.). In certain examples, the boundary can define an area on the model or atlas that will (or conversely, that will not) be changed, stretched, deformed, or otherwise altered. Thus, the boundary can protect one or more areas that do not need to be changed, or it can define one or more areas that can be changed.

In an example embodiment, the boundary can include a boundary around one or more specific structures or substructures of the brain that can be manually defined by a clinician or other user, or that can be automatically defined (e.g., already defined in the model or brain atlas, or automatically detected and placed by the clinician programmer system or other device, system, or method).

In an example embodiment, and as shown in FIGS. 10A-10B, two or more boundaries can define a first area 10000, a second area 10002, and a third area 10004. The first area 10000 can be defined using a first border 10001. The first area 10000 can be defined as one that can be moved, relocated, or otherwise altered. The third area 10004 can be defined using a second border 10003 (e.g., the second border 10003 coupled with one or more other boundaries, such as the edge of the model or brain atlas or other boundary 10005). The third area 10004 can be defined as one that cannot be moved, relocated, or otherwise altered. The second area 10002 can be defined as the area between the first border 10001 and the second border 10003 and can be defined as an area that can be stretched or deformed (e.g., linearly or nonlinearly, automatically or manually set or adjusted) to accommodate the movement, relocation, or other alteration of the first area 10000. For example, FIG. 10B shows area 10000 shifted to the right as compared to its position in FIG. 10A, with a corresponding deformation of area 10002.

In an example embodiment of the present invention, the system is configured to automatically adjust a model or brain atlas according to specific brain injuries or deformities.

Figure 5:
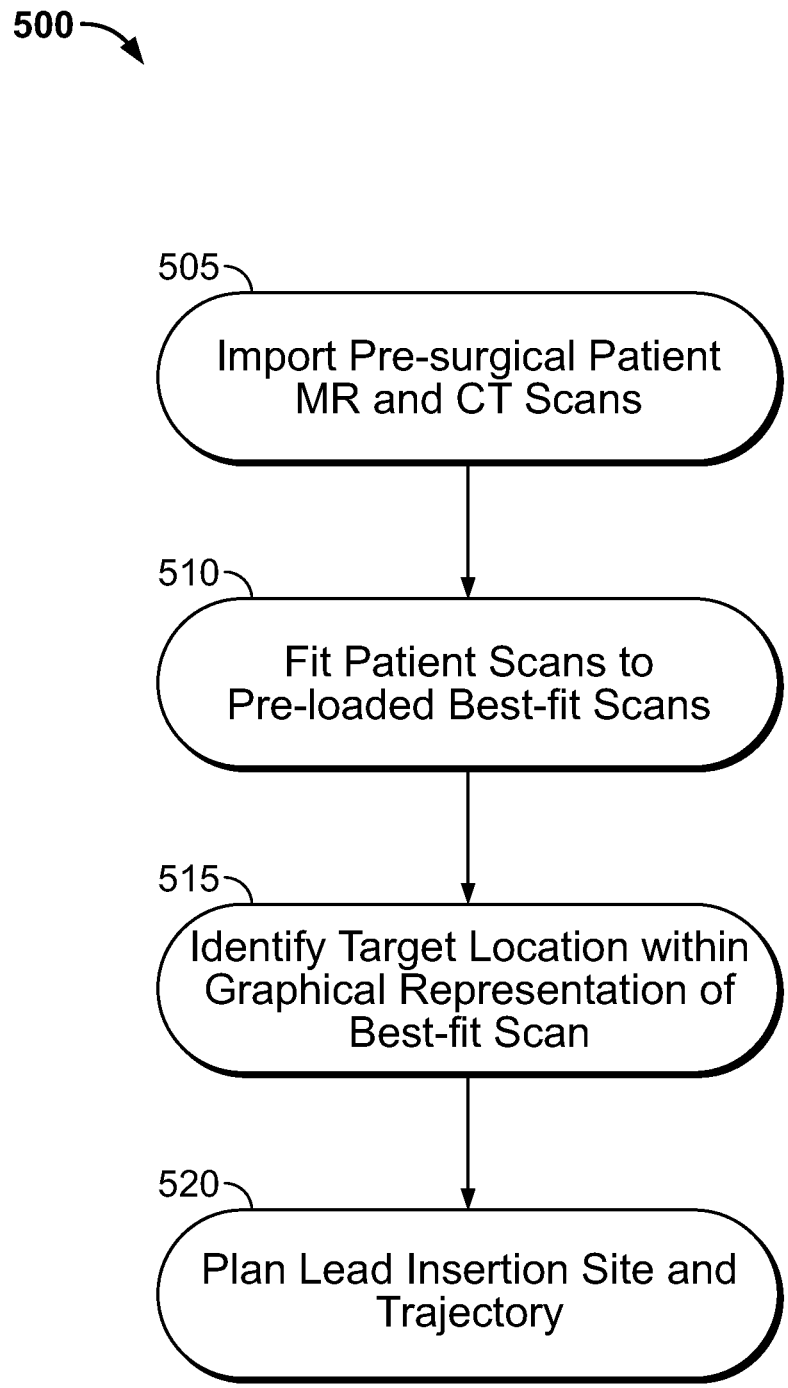
FIG. 5 illustrates generally an example of a method including importing pre-surgical medical images, identify a target location, and plan a lead insertion site through its territory.

FIG. 5 illustrates generally an example of a method 500, according to an example embodiment of the present invention, including importing pre-surgical patient MR (or MRI) and CT scans, fitting patient scans to a pre-loaded best-fit atlas(es), identifying a target location within a graphical representation of a best-fit scan, and planning the lead insertion site and trajectory.

At step 505, pre-surgical patient MR and CT scans are imported. In an example, the MR and CT scans include at least one of MR, CT, or other medical scan, image, or data. In an example, the scans are imported into the clinician programmer system, such as into the clinician programmer terminal 105.

At step 510, patient scans are fit to pre-loaded best-fit atlases or scans. In certain examples, the patient scans can be automatically fit (e.g., by the clinician programmer system) to pre-loaded best-fit atlases or scans, or the patient scans can be manually fit (e.g., by a user) to pre-loaded best-fit atlases or scans.

In an example, once imported, the scans can be analyzed, such as automatically by the clinician programmer system using image processing or other techniques or algorithms, for example, to automatically create a model (e.g., a 3-D model) of at least a portion of the patient's brain anatomy, including brain structures, substructures, or other anatomy, or to automatically fit a pre-loaded best-fit scan or preloaded model (e.g., a preloaded 3-D model, such as one of a plurality of stored 3-D models) of the patient's brain anatomy. In other examples, the scans can be analyzed, such as manually by a user, or a combination of automatically by the clinician programmer system or manually by the user, to create a model of the patient's brain anatomy, or to fit a pre-loaded best-fit scan or preloaded model of the patient's brain anatomy, such as a brain atlas.

At step 515, the target location for treatment is identified within the graphical representation of the best-fit scan. In an example, the target location can be identified by a clinician using the model or pre-loaded best-fit scans. For example, the system may provide for receipt and processing of user input selecting a plurality of points within a 2-D or 3-D model to outline a 2-D or 3-D target location. The system may further provide for clicking and dragging upon one or more points of a displayed target location to change its shape. Any suitably appropriate user input device, e.g., a computer pen, a touch-sensitive screen, a mouse, joystick, and/or other controller, may be used for obtaining the user input.

In other examples, the target location can be identified or suggested by the clinician programmer system, for example, using clinician input, the patient's information (such as a patient disorder, patient history, etc.) population information (such as learned information from one or more other patients).

At step 520, a lead insertion site and trajectory are planned. In an example, the lead insertion site can be planned according to the identified target location.

In an example embodiment of the present invention, the clinician programmer system is configured to plan a surgical path for implantation of a stimulation leadwire using a head-frame (e.g., Lexcel), a frameless head mount (e.g., Nexframe), or other surgical tool.

In an example embodiment of the present invention, the system is configured to receive information from a microelectrode, e.g., a microelectrode recording (MER), including information about the trajectories of each MER track into the brain or a log of critical points on each track. In certain examples, the system receives MER data entered manually by a user or automatically entered by receiving data directly from a MER system (e.g., the MER system including a microelectrode coupled to a lead or other communicative element).

In an example embodiment, information detected at certain depths or locations inside the brain can be used for indications of structure, substructure, boundaries, or other medical or location specific information. In an example, the system uses the information obtained from the microelectrode, such as the critical points, to create or alter a model or scalable atlas to create an accurate rendition of the patient's brain or one or more substructures of the patient's brain.

Figure 6:
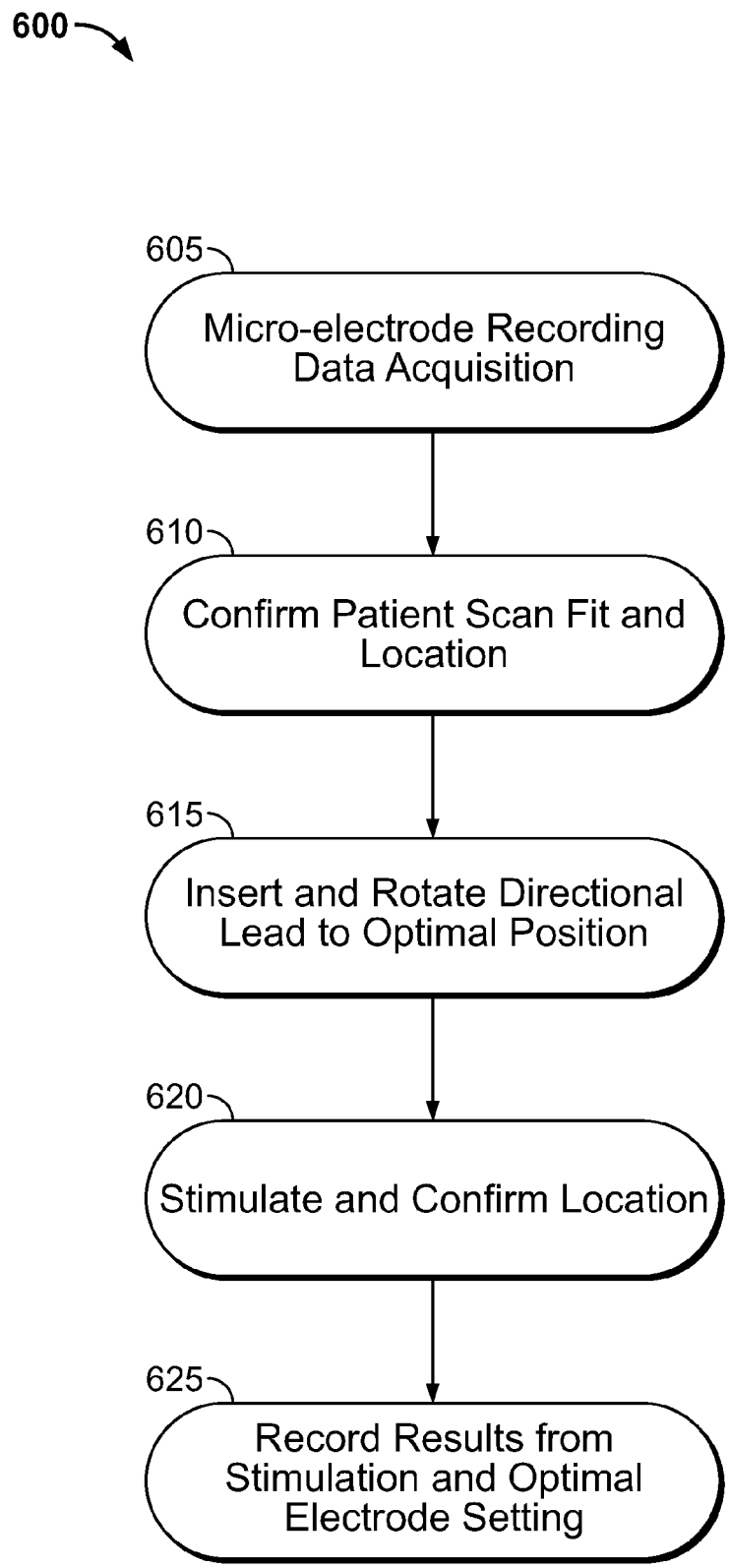
FIG. 6 illustrates generally an example of a method including acquiring MER data, stimulating and confirmation lead location, and recording the results.

FIG. 6 illustrates generally an example of a method 600 including acquiring microelectrode recording (MER) data, confirming patient scan fit and location, inserting and rotating a directional leadwire to an optimal position, stimulating and confirming location, and recording results from the stimulation and optimal electrode setting.

At step 605, MER data is acquired. Example embodiments provide for MER data to be acquired, uploaded, input, or stored manually, such as by a clinician or other user, or automatically in the clinician programmer system.

In an example embodiment, a microelectrode can include an electrode having a tip dimension small enough (e.g., less than 1 mm) to allow nondestructive puncturing of a plasma membrane. The size of the microelectrode can allow intracellular recording of resting and action potentials, the measurement of intracellular ion or pH levels, or microinjection.

In an example embodiment, the microelectrode can be inserted into the brain, such as at a proposed or actual trajectory of a therapy delivery or other device or at another area, and can be configured to receive physiological information indicative of a location, structure, or substructure of the brain at which the microelectrode is located or with which the microelectrode is in contact.

At step 610, patient scan fit and location is confirmed. In an example, once acquired, the MER data can be used to, manually via an interface of the clinician programmer system or automatically, create, confirm, or adjust a model or best-fit scan of the patient's brain anatomy. For example, the scan fit performed at step 510 may be modified. For example, a light brain shift that occurs due to the DBS operation, e.g., specifically the drilling of the burr hole, for which the brain atlas may be corrected based on the MER data.

After confirmation, at step 615, the stimulation leadwire is inserted and, if necessary, the leadwire is rotated to an optimal position. In an example, the optimal position can include a position predicted using the clinician programmer system, or a position selected by the clinician or other user.

In example embodiments of the present invention, the clinician programmer system can receive post-operative medical images, e.g., to show the exact location of an implanted stimulation leadwire. In certain example embodiments, the system is configured to superimpose a model of the stimulation leadwire over the location of the implanted stimulation leadwire, and/or to adjust the scalable atlas to show the appropriate rendition of the patient's brain or one or more substructures of the patient's brain.

Image Importation for Atlas Generation

In an example embodiment of the present invention, the creation or adjustment of a patient brain atlas may be performed with images obtained from external patient medical files recorded independent of any DBS therapy procedures, including medical images taken prior to and/or subsequent to the leadwire implantation. While FIGS. 1a-1b refer specifically to MRI and CT data, it will be appreciated, that images and/or data of other modalities, such as Functional Magnetic Resonance Imaging (fMRI), Diffusion Tensor Imaging (DTI), Positron Emission Tomography (PET), and/or X-ray, may be used.

Figure 1A:
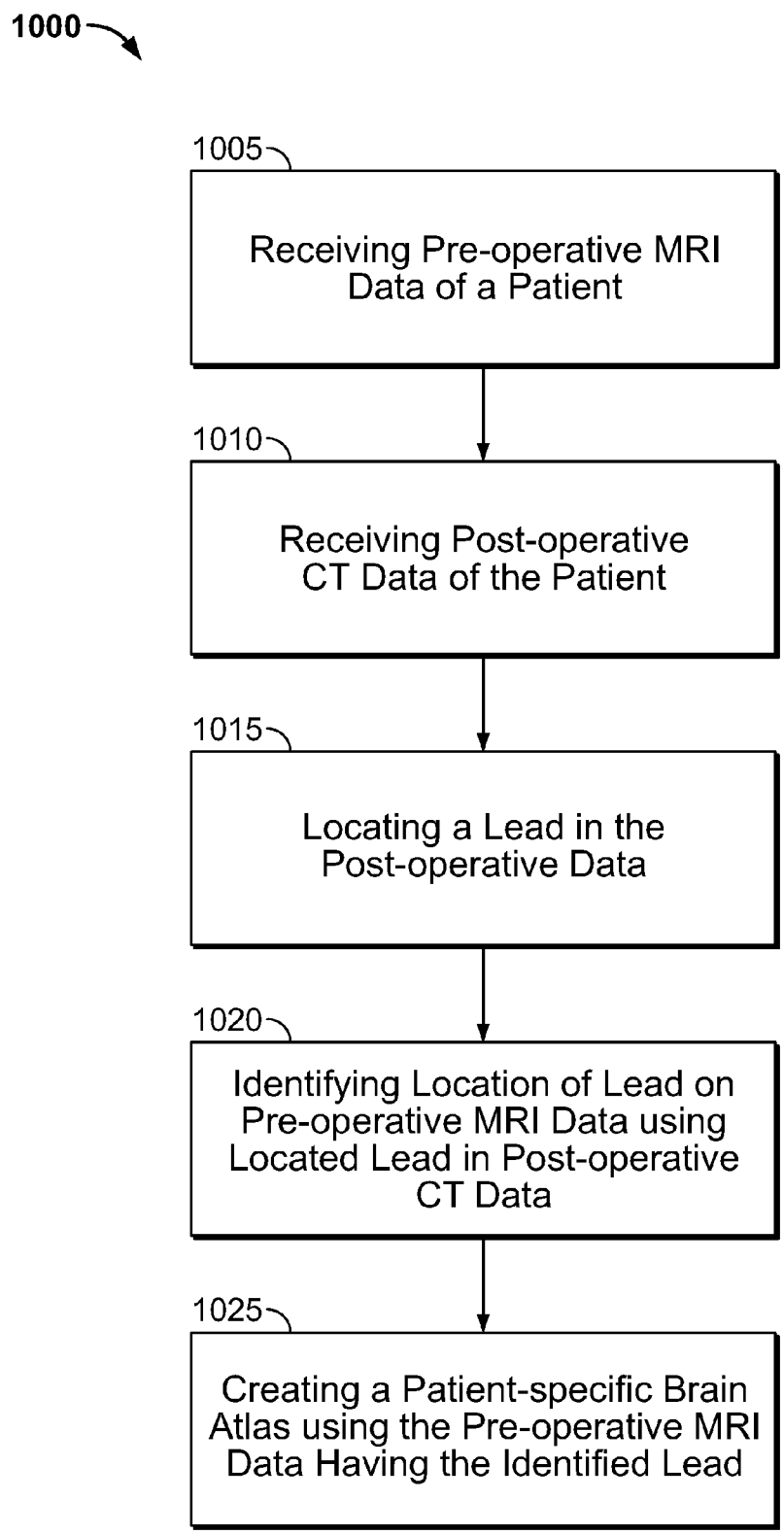
FIGS. 1a-1b illustrate generally examples of using retrospective data to generate and/or modify a patient atlas for use to tailor DBS parameters and/or monitor DBS therapy.

FIG. 1a illustrates generally an example of a method 1000 for using retrospective data to create or modify a patient specific brain atlas for use to tailor or otherwise alter or change one or more DBS parameters and/or for use to monitor or judge the efficacy or potential for improvement of an existing DBS or other therapy.

At step 1005, pre-operative magnetic resonance imaging (MRI) data of a patient is received. (Alternatively, a post-operative MRI image or another pre- or post-operative medical image may be used.) In an example, the pre-operative MRI data of the patient can include an MRI scan taken prior to implanting a lead or electrode in the patient's brain. In other examples, the pre-operative MRI data can include any stored or other MRI data in the patient's medical file or other storage location, or the MRI data can include other MRI data of the patient recorded at some time in the patient's past. In an example embodiment, it is not required for the image to have been taken in preparation for the implantation of the leadwire. (Similarly, in an instance in which a post-operative MRI or other medical image is used, it is not required for the post-operative medical image to have been taken in relation to the implanted leadwire.) Thus, in an example embodiment, it is not required for any new MRI or other medical image data to be obtained for this procedure or for these purposes. Instead, previously attained MRI or other medical imaging data may be used.

At step 1010, post-operative computed tomography (CT) data of a patient is received. In an example, the post-operative CT data of the patient can include a CT scan taken following implantation of a leadwire in the patient's brain. In other examples, the post-operative CT data can include any stored or other CT data in the patient's medical file or other storage location showing the implanted leadwire, or the CT data can include other CT data of the patient recorded at some time in the patient's past, following implantation of the leadwire. Thus, in example embodiments of the present invention, obtaining any new CT data for this procedure or for these purposes is not required. Instead, previously attained CT data may be used.

At step 1015, a leadwire is located, e.g., axially and/or rotationally, automatically or manually in the post-operative CT data. Once the leadwire is located, the implanted location of the lead or electrode can be identified or recorded.

At step 1020, the location of the leadwire can be identified on the pre-operative MRI data, or other MRI data, using the located leadwire in the post-operative CT data, or other CT data. Alternatively, the post-operative or other CT data can be correlated, registered, co-registered, or otherwise morphed, changed, or altered, e.g., to the same or similar view, plane, or other orientation as the MRI data, to identify the location or placement of the identified lead or electrode on the pre-operative or other MRI data.

At step 1025, a patient-specific brain atlas is created using the pre-operative or other MRI data having the identified lead.

Alternatively, the patient-specific brain atlas can be created using the pre-operative or other MRI data, and the lead location can be identified or placed on the patient-specific brain atlas using the location identified on the pre-operative or other MRI data.

Figure 1B:
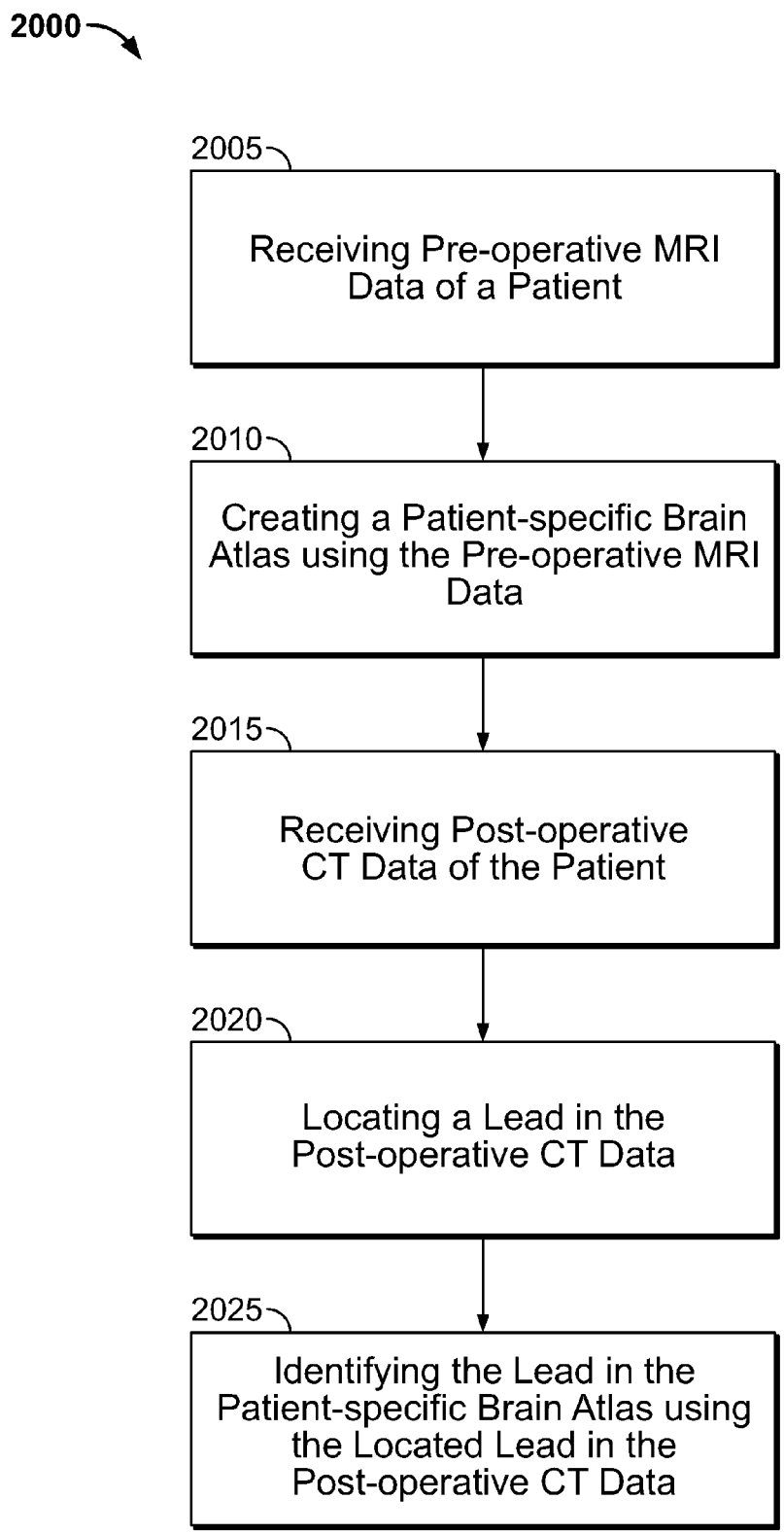

FIG. 1b illustrates generally an example of an alternative method 2000 for using retrospective data to create or modify a patient specific brain atlas for use to tailor or otherwise alter or change one or more DBS parameters and/or for use to monitor or judge the efficacy or potential for improvement of an existing DBS or other therapy.

At step 2005, pre-operative (or post-operative) MRI data of a patient is received.

At step 2010, a patient-specific brain atlas is created using the pre-operative MRI data.

In other examples, the patient-specific brain atlas can be created using other MRI data or other medical images.

At step 2015, post-operative CT data of the patient is received.

At step 2020, a leadwire is located in the post-operative CT data.

At step 2025, the leadwire is identified in the patient-specific brain atlas using the located leadwire in the post-operative CT data.

In an alternative example embodiment, the leadwire may be located in an MRI image without use of CT data.

Locating Directional Leadwire

In an example embodiment of the present invention, a directional leadwire can be located in a biological medium using one or more mechanical features or electrical features to locate the leadwire in a medical image, e.g., using software. The leadwire may include features as those described in U.S. patent application Ser. No. 12/029,141, filed Feb. 11, 2008, the entire disclosure of which is herein incorporated by reference in its entirety. In an example, the medical image can include at least one of a fluoroscopy, a post-op MRI, and a post-op CT. In other examples, other imaging modalities may be used.

Generally, a directional leadwire can be located both axially and rotationally. In an example, the leadwire can include a directional electrode and/or a locating feature on one side of the leadwire that is visible under CT or MRI. A directional electrode is an electrode that extends less than 360° about the body of the leadwire. If a post-op CT is used, the leadwire can be located relative to one or more targeted brain structures by merging the post-op CT with the pre-op MRI, or vice versa.

In an example, the leadwire can be automatically located in a medical image. To determine the location of these electrodes, post-op images may be segmented using one or more image segmentation algorithms, possibly including a histogram-based and edge-detection method as a coarse first pass to identify regions of interest in the CT volumes and template matching and clustering techniques to segment the electrode from other high intensity regions.

In addition, a locating feature may be incorporated into the leadwire to assist in discernment of its rotational location.

In an example, if MRI is used, a post-op MRI can be taken and the same process can be used without merging the post-op CT. In this example, the post-op MRI can be sufficient to locate the leadwire relative to the brain structures, e.g., by automatically locating the leadwire in the post-op MRI by identifying the artifact that is created during imaging.

Figure 24A:
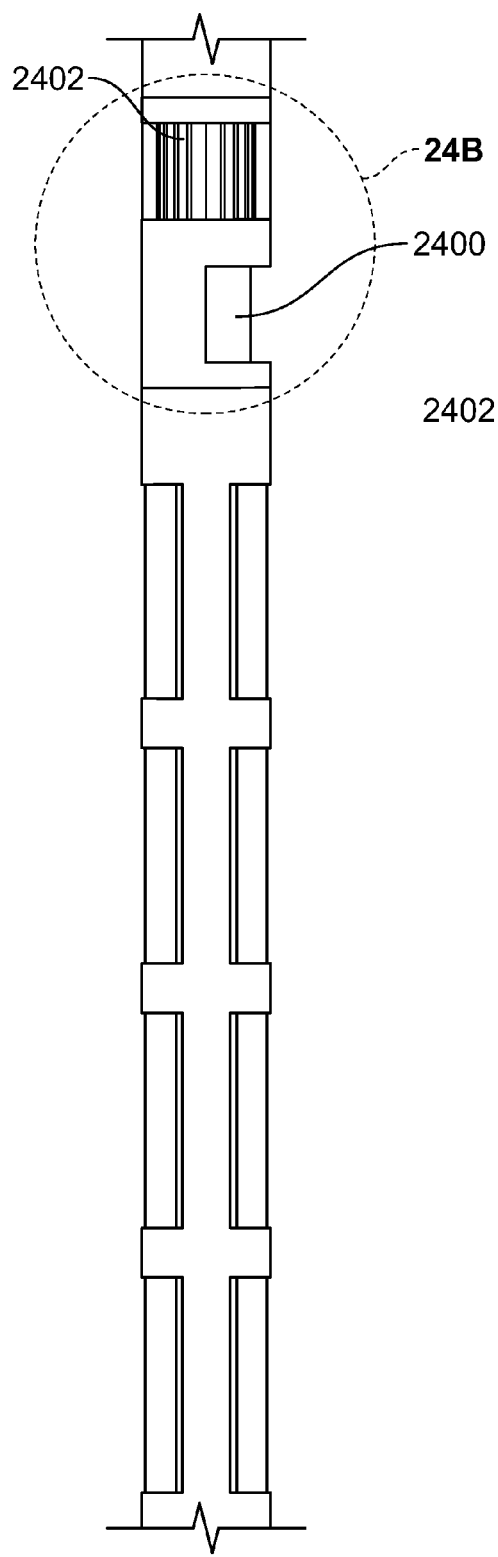
FIGS. 24A-B illustrate a 2 window concept for directional leadwire location, according to an example embodiment of the present invention.
Figure 24B:
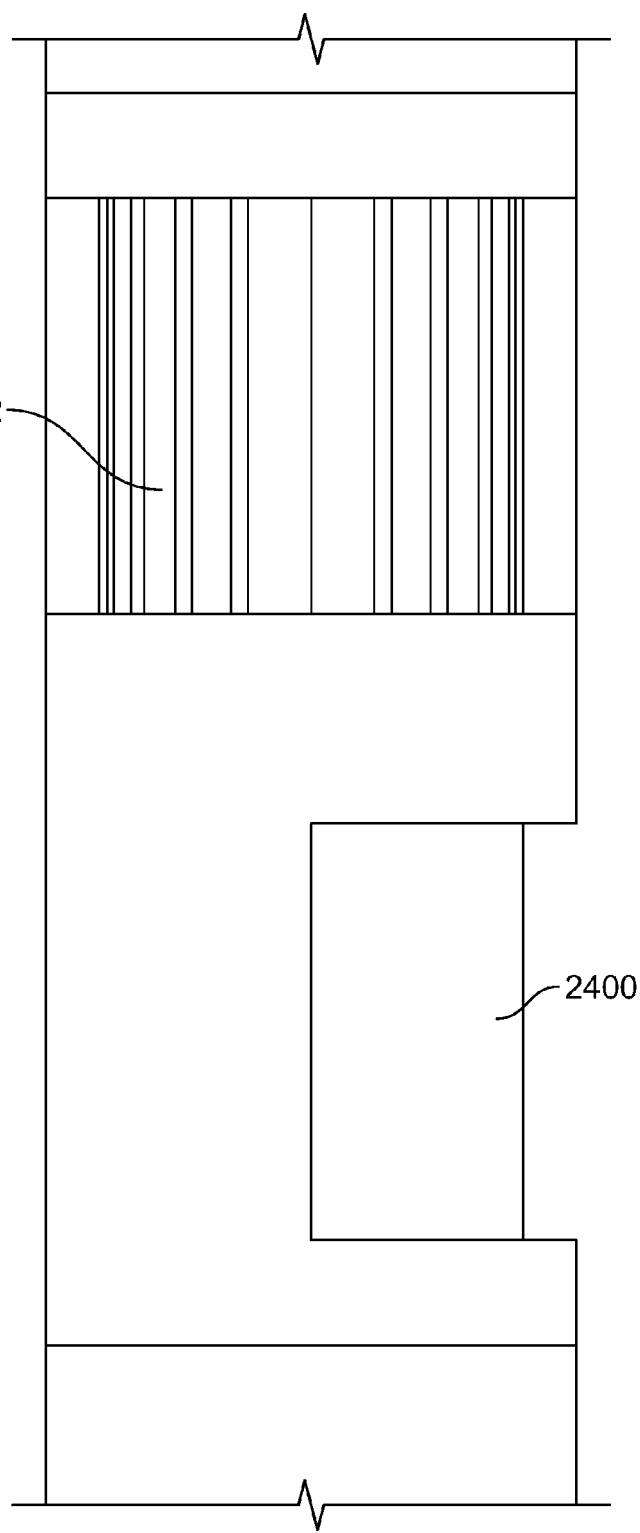

An example embodiment of the present invention may include a two window concept for directional leadwire locating features as shown in FIGS. 24A-B, for example, where bands include recessed portions.

Another example embodiment may include a two triangle concept for directional lead locating features as shown in FIGS. 25A-B. In other example embodiments, other shapes may be used. For example, other shapes may be used. For example, the shapes may include components having a particular orientation, such that the orientation of the shapes of the two markers may differ. According to these example embodiments, the markers may be shapes that protrude from a band, rather than windows in one or more bands.

The angle at which these features are viewed under fluoro, CT, and/or MRI can tell the user the direction in which each electrode set is pointing.

In the embodiment providing the two triangle (or other shape, e.g., including a protrusion) concept, the two triangles (or other shape) may be identically shaped. This way, with rotation of the leadwire about the longitudinal axis of the leadwire, the user can tell the direction of the electrodes based on what is seen on the fluoroscopy image.

FIGS. 24A-B and 25A-B are indicative of potential radiopaque directional marker bands that could be designed into a leadwire containing directional electrodes. The two designs work in essentially the same manner. When a leadwire with directional electrodes is implanted in a patient, a physician can take, e.g., a fluoroscopy image of the patient. Depending on the image the physician sees in the fluoroscopy image, the physician can tell in which direction the electrodes are pointing due to the asymmetry of the marker band. This helps when programming the patient.

For example, in FIGS. 24A and 24B, the leadwire may include two windows 2400 and 2402, each extending 180°, one on top of the other. The windows may be shifted relative to each other by a number of degrees, e.g., 30°, 45°, or 90°. In an example embodiment, they may be advantageously offset by 90° as shown in FIGS. 24A and 24B. Similarly, in FIGS. 25A and 25B, the leadwire may include two triangular shapes 2500 and 2502, each extending 180°, one on top of the other. The shapes may be shifted relative to each other by a number of degrees, e.g., 30°, 45°, or 90°. In an example embodiment, they may be advantageously offset by 90° as shown in FIGS. 25A and 25B. Other shapes may be similarly used.

Figure 26:
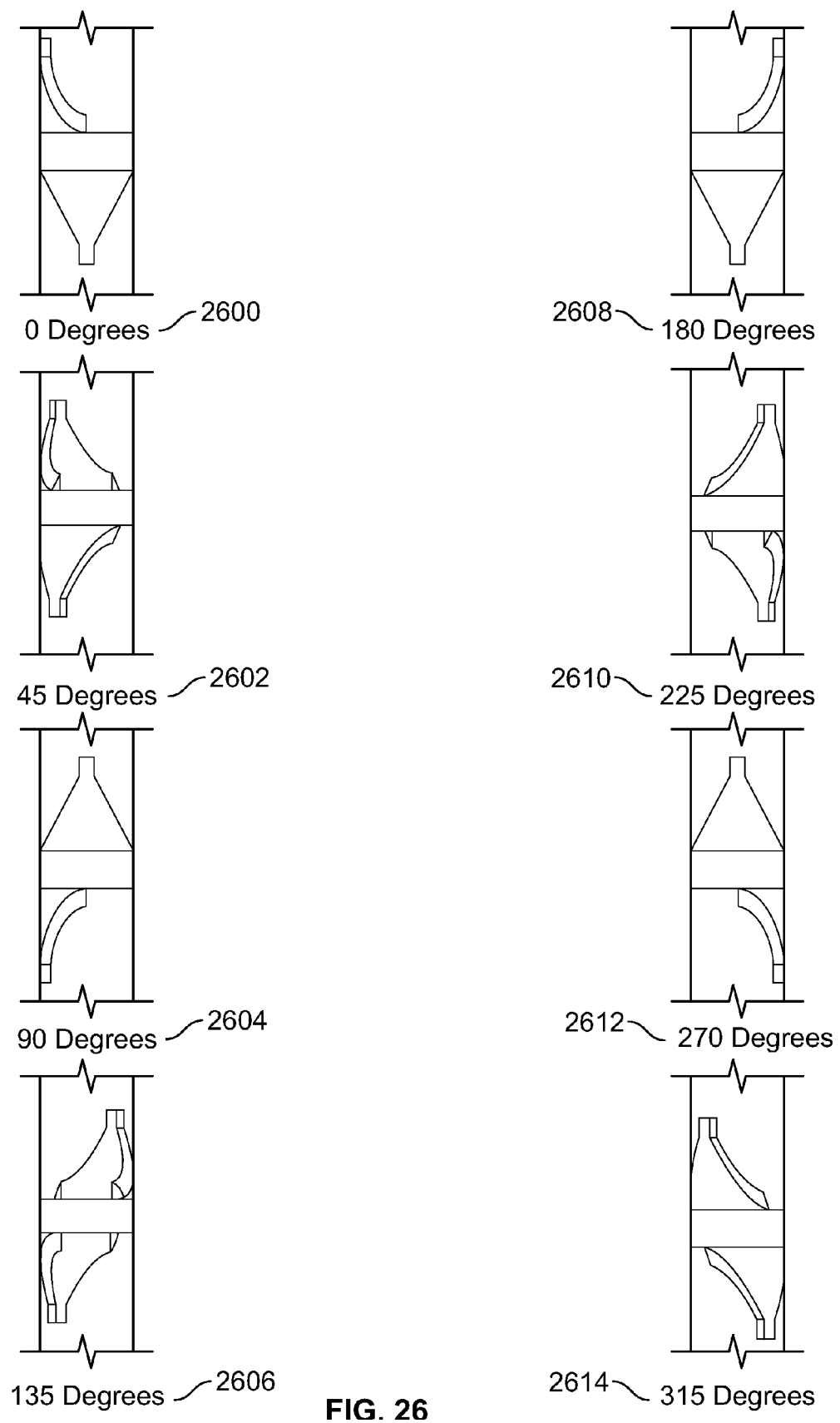
FIG. 26 shows an image set that can be displayed in the interface screen, according to an example embodiment of the present invention.

FIG. 26 shows an image set that can be displayed in the interface screen according to an example embodiment of the present invention. For example, views for 0° 2600, 45° 2602, 90° 2604, 135° 2606, 180° 2608, 225° 2610, 270° 2612, and 315° 2614 may be displayed. In other example embodiments, differences in the rotational position of the leadwire in the displayed views may be by a different number of degrees. As shown in FIG. 26, depending on the rotational position of the leadwire, the two markers would be seen at different locations, and in some positions, one or both of the markers would not be seen at all (though a shadow may be seen as shown, e.g., at 2602-2610, depending on the imaging modality). The physician would select, via the user interface, which pictures most closely relate to the image the physician is viewing in a fluoro machine, CT, or MRI. The physician may also select the direction in which the fluoro image was taken (AP, Lateral, or oblique angle). The programming software would then automatically locate the leadwire rotationally in the 3-D viewer allowing for more knowledge of the leadwire directionally in the patient's anatomy and thus easier programming of the patient.

In an example embodiment, the system and method provides for the user to match the image obtained via fluoroscopy to an image displayed on the user interface screen (these could be displayed in any number of increments, e.g., every 45° as shown in FIG. 26). This would allow the software to properly align the lead rotationally in the 3-D display.

Example Model Output

Figure 3A:
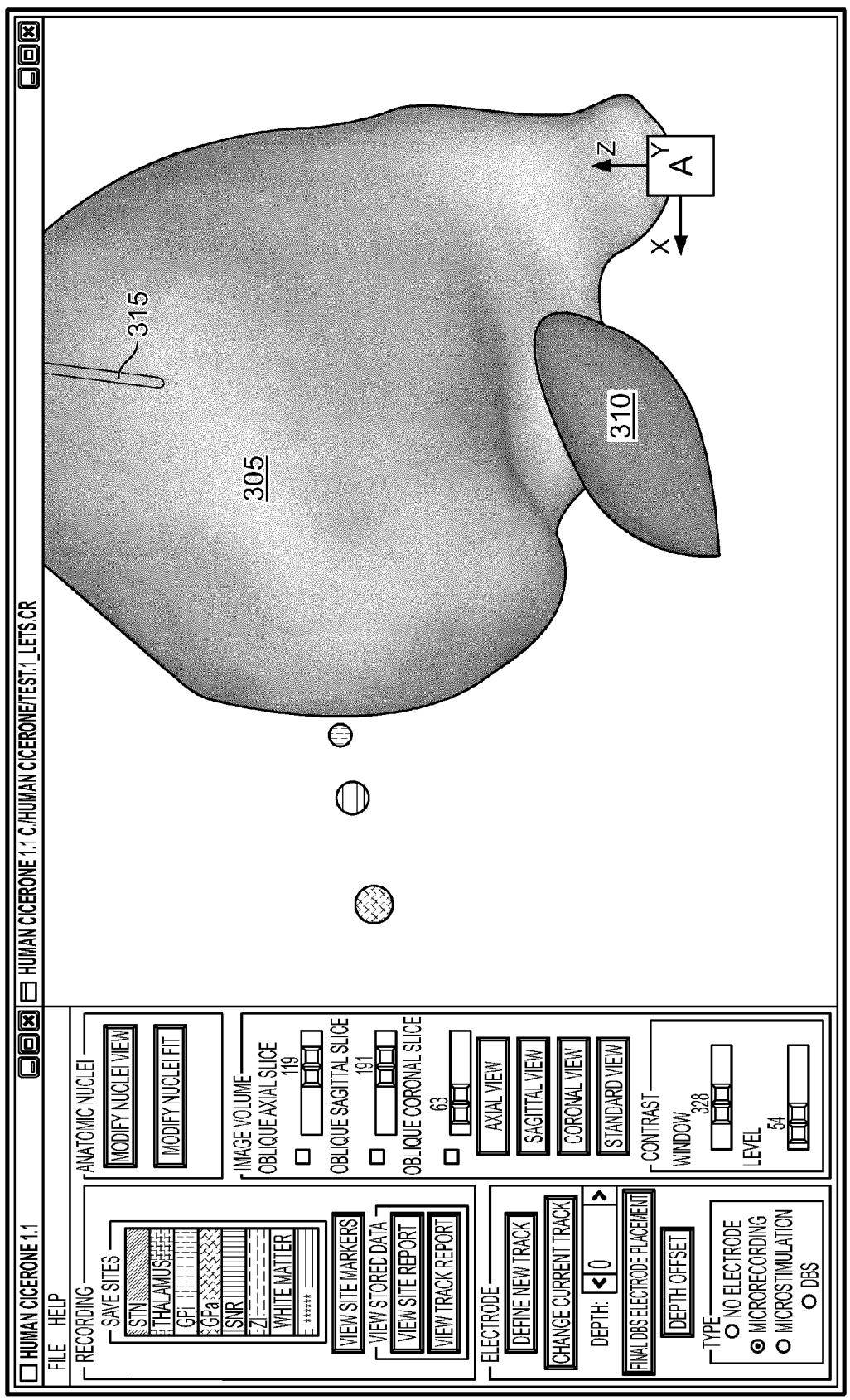
FIGS. 3a-3j illustrate generally examples of clinician programmer output.

FIGS. 3a-3j illustrate generally examples of output of the clinician programmer system according to example embodiments of the present invention. FIG. 3a illustrates generally an example of output including a 3-D view of one or more substructures of a patient's brain, including a thalamus 305 and a subthalamus nucleus (STN) 310. In the example of FIG. 3a, an electrode leadwire 315 is shown in the thalamus 305. In certain examples, the electrode leadwire 315 can include a microelectrode configured to record electrical information indicative of a location of the brain. In addition or alternatively, the electrode leadwire 315 can include one or more stimulation electrodes.

In an example embodiment of the present invention, the system is configured to display one or more coronal, sagittal, or axial slices of the patient's brain, or of a representation of the patient's brain (e.g., a model, a stretched or deformed brain atlas, or other representation). In other examples, other structures or substructures of the patient's brain can be shown or represented using the clinician programmer system.

Figure 3B:
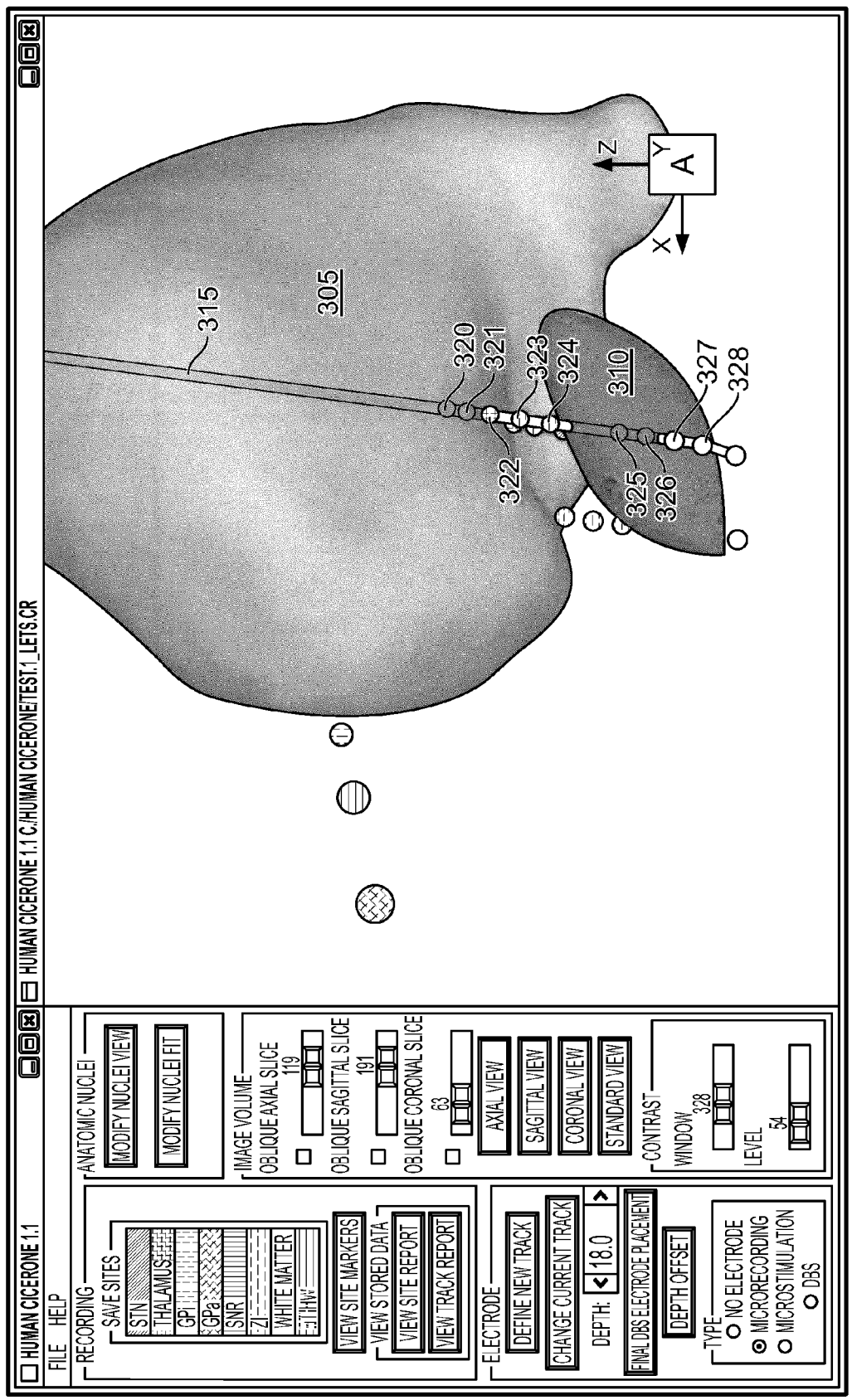
Figure 3C:
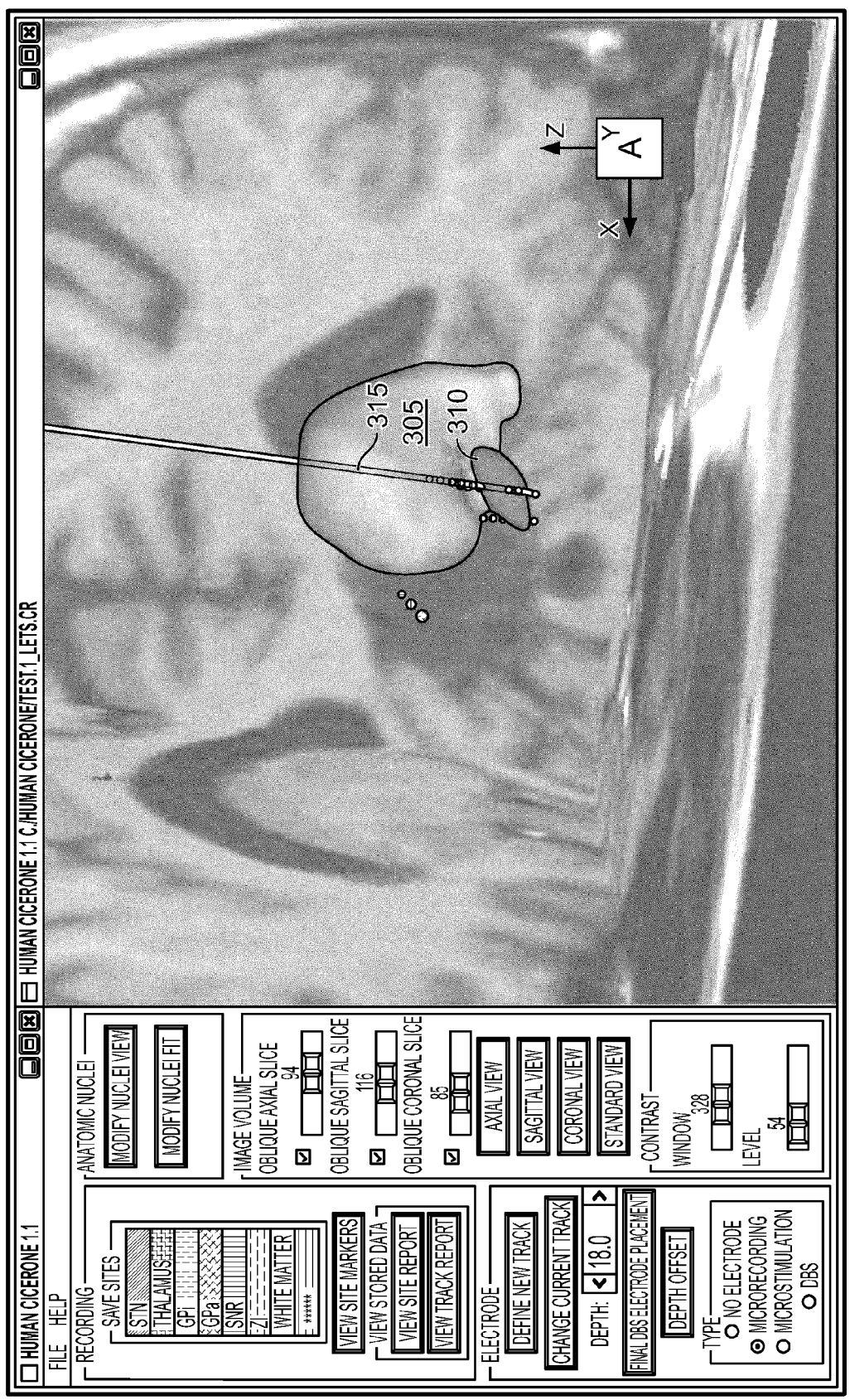

FIGS. 3b-3c illustrate generally an example of clinician programmer system output including a 3-D view of one or more substructures of a patient's brain, including a thalamus 305 and a STN 310. In the example of FIG. 3b, an electrode leadwire 315 may be used to determine one or more locations of one or more substructure. For example, when the electrode leadwire 315 (or at least one contact on the electrode leadwire 315) is in the thalamus 305, the electrode leadwire 315 can receive information indicative of the thalamus 305. As the electrode leadwire 315 is progressed into the brain, information can be received, e.g., at one or more specific or random intervals. In the example of FIG. 3b, information can be received at different locations, e.g., location 320-329, etc. The information received at location 320 is indicative of the thalamus 305, and is accordingly marked as such (e.g., visually, with a yellow color). Using this information, one or more model, atlas, or other representation can be stretched, deformed, or otherwise altered according to the information.

In certain examples, more than one electrode leadwire can be used, or the electrode leadwire 315 can be inserted in more than one location to receive information indicative of the location of a patient's structure or substructure.

FIG. 3c illustrates generally an example of clinician programmer system output including a 3-D view of one or more substructures of a patient's brain, including a thalamus 305 and a STN 310, similar to that shown in FIG. 3b, although shown in relation to the overall structure of the patient's brain.

Intra- and Post-Operative Steps

Figure 7:
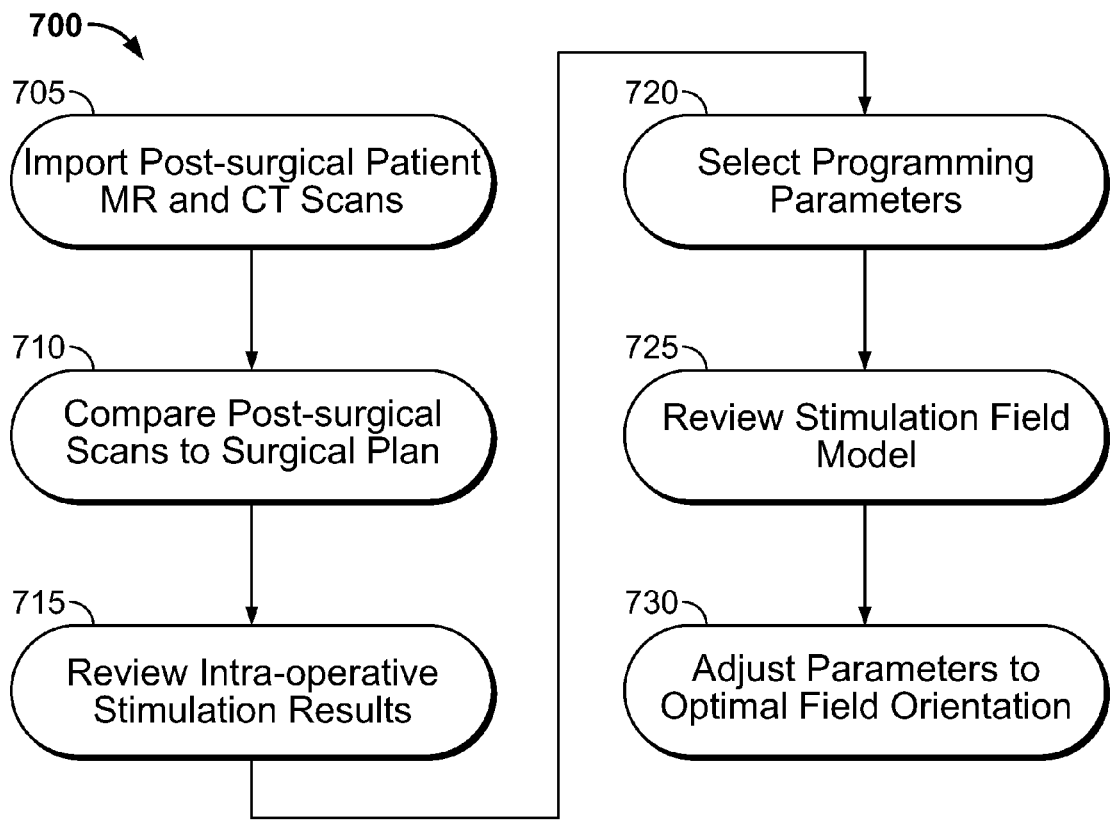
FIG. 7 illustrates generally an example of a method including adjusting parameters to optimal field orientation.

FIG. 7 illustrates generally an example of a method 700 including importing, e.g., post-surgical patient MR and CT scans, comparing post-surgical scans to a surgical plan, reviewing intra-operative stimulation results, selecting programming parameters, reviewing stimulation field models, and adjusting parameters to optional field orientation.

At 705, post-surgical patient MR and CT scans or one or more other medical images are imported.

At 710, post-surgical scans are compared to the surgical plan. In an example, the post-surgical scans are compared to the surgical plan to verify correct placement, direction, or location of the leadwire or other component. For example, if there is a difference, the leadwire may be moved.

Returning to FIG. 6, at step 620, a stimulation is applied and the location of the electrodes relative to the brain structures is confirmed axially and rotationally, e.g., based on one or more medical images or other sensor or observed data.

For example, referring again to FIG. 7, the confirmation may include a review, at step 715, of intra-operative stimulation results. That is, trial stimulations may be performed prior to closing of the patient's head to determine whether any benefits and/or side effects result from the stimulations with the leadwire at its present location. For example, depending on the results, the leadwire may be left in its present location, the leadwire may be removed, or the leadwire's location may be changed.

Referring again to FIG. 6, at step 625, results from stimulation and optimal electrode settings are recorded and/or stored, e.g., using the clinician programmer system.

For example, returning to FIG. 7, after the patient's head is closed, program parameters may be selected at step 720. In an example, the program parameters or other therapy parameters are selected by the clinician or other user. In an example, the clinician programmer system can suggest optimal program parameters, e.g., parameters that are predicted to result in an estimated VOA that closely corresponds to a target VOA manually input as described above or automatically determined, for example, based on a therapeutic goal.

In an example embodiment, the clinician programmer system, using a 3-D model, atlas, or other representation of a patient's brain, can estimate a VOA as described in detail below and display the estimated VOA on the 3-D model or other representation.

Figure 3D:
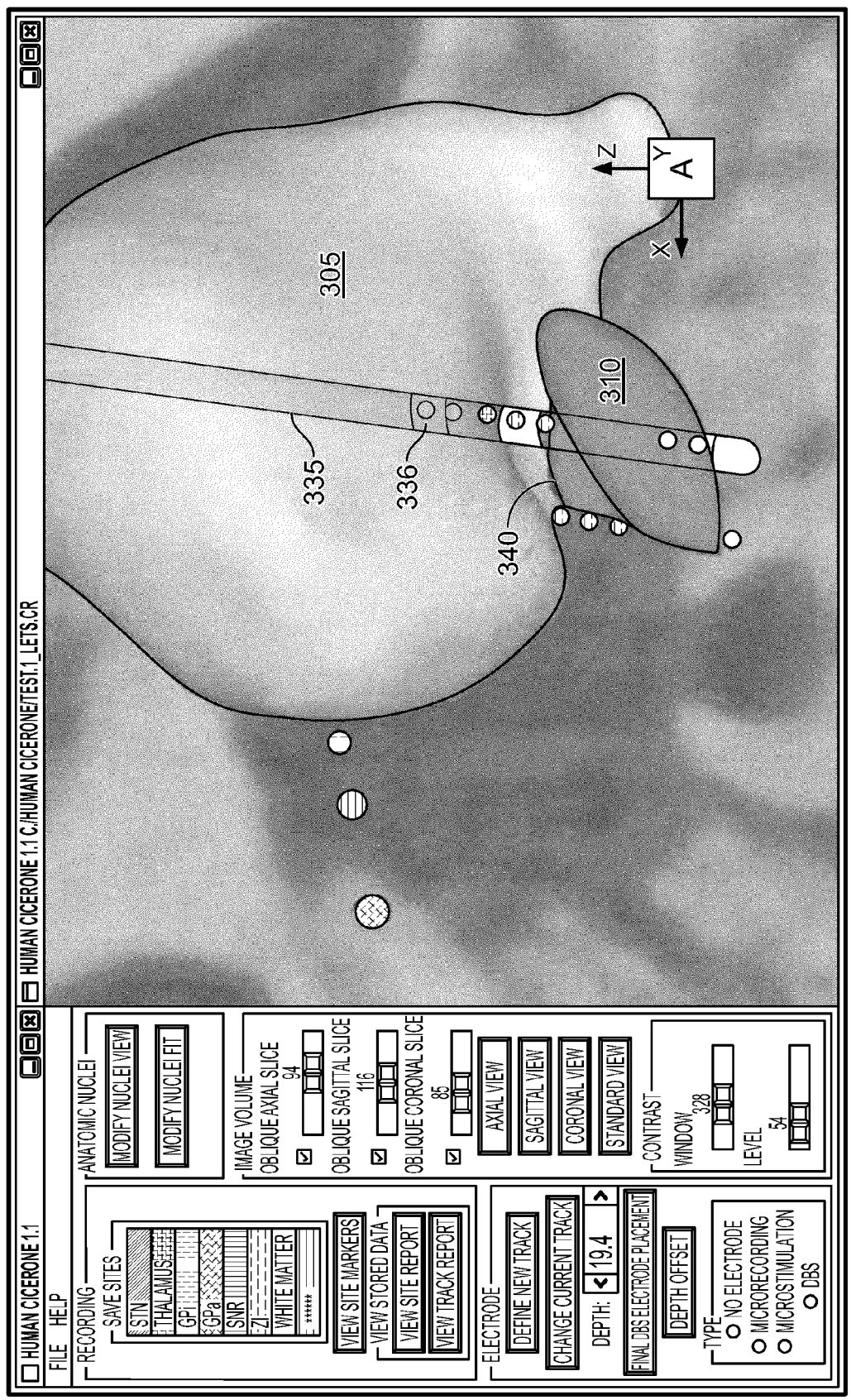

FIG. 3d illustrates generally an example of clinician programmer system output including a 3-D view of one or more substructures of a patient's brain, a stimulation leadwire 335, and a VOA 340. In an example embodiment of the present invention, the stimulation leadwire 335 includes one or more electrical contacts or electrodes (e.g., electrode 336, etc.), configured to selectively deliver a stimulation energy to at least a portion of the brain.

At 725, the VOA estimated for the selected program parameters is reviewed.

At 730, based on the review, stimulation parameters are adjusted to optimal stimulation field orientation. In an example, the parameters can be adjusted to account for variation between the surgical plan and the actual leadwire or other component placement, direction, or location.

In example embodiments of the present invention, results of stimulations can be uploaded, stored, or otherwise used to create or update a database of computed therapy parameters, e.g., to determine predictive algorithms or other relationships between different varying therapy parameters as described in more detail below.

Parameter and VOA Configuration

In an example embodiment of the present invention, the clinician programmer system is configured to calculate, define, establish, or otherwise set or alter one or more therapy parameters using the created patient-specific brain atlas or other model or representation of the patient's brain including the implanted lead location.

In an example embodiment of the present invention, once the rendition of the stimulation electrode leadwire implanted in the patient's brain and the rendition of the local anatomic structure have been created, e.g., once a model of the patient's brain had been created, adjusted, or otherwise established, programming of the energy delivery can begin. In certain examples, the desired stimulation parameters (e.g., stimulation pulse amplitude, pulse width, frequency, etc.) can be entered into the clinician programmer system. The amplitude can range, e.g., between 0-20 mA. Pulse width can range, e.g., between 10-1000 µsecond per phase, and frequency can range, e.g., between 1-1200 Hz. Other ranges may also be used. In an example embodiment, once the stimulation parameters have been entered, the clinician programmer system is configured to predict a VOA. In an example embodiment of the present invention, the clinician programmer system is configured to graphically show the VOA with respect to the implanted stimulation electrode leadwire and the patient's brain. In an example embodiment of the present invention, the system is configured to predict one or more potential side effects based on the predicted VOA interacting with adjacent anatomical structures. The system is configured to display these side effects to a user, such as graphically or textually using the viewer/navigator or other display.

In an example embodiment of the present invention, once a model of the patient's brain has been created, adjusted, or otherwise established, the system is configured to receive input of a desired VOA (e.g., a desired VOA created, drawn, or otherwise input by a user). For example, the clinician programmer system may display a 3-D rendering of an anatomical substructure of the patient's brain and allow a clinician or other user to input, e.g., graphically, a desired ESF or VOA. For example, the clinician programmer system may include a user-interface, such as a mouse, a stylus, or other input device, and may be configured to receive information from the user-interface to create the desired or target VOA.

Alternatively, the system may automatically determine a suggested VOA using information about the patient. For example, the clinician or other user can input a desired therapy outcome, or other information, such as patient condition, indications, symptoms, or other information for use by the system to determine the VOA.

In an example, selection of the VOA may be based on analysis of prior VOAs with regard to anatomical location and comparison to outcome results (progressively on the software, off-line on another computer, etc.) or through anatomical landmarking where a target volume is determined by the expected anatomical and physiological response. For example, based on benefits and/or side effects resulting from previous stimulations using parameters corresponding to certain estimated VOAs, a target region for stimulation may be formed, e.g., for a specific single therapy or for a total patient benefit for a desired combination of therapies.

In an alternative example embodiment, selection of the VOA may be performed without reference to anatomical structures. Instead, prior VOAs may be analyzed solely with respect to the leadwire and based on patient clinical data to determine benefits and side effects associated with those VOAs as defined relative to the leadwire. Accordingly, a VOA may be selected relative to the leadwire, without regard to the particular anatomical structures with which it overlaps.

In an example, once the desired or target VOA has been input, received, or created (automatically or via user input), it can be displayed to the clinician or other user using the clinician programmer or other display device, e.g., in order to validate the created desired or target VOA.

In certain examples, the desired VOA is created in 2-dimensions (2-D) on one or more slice or other 2-D representation of the patient's brain or substructures of the patient's brain (e.g. a plane orthogonal to the lead), or the desired VOA is created in 3-D on a representation (3-D or other) of the patient's brain or substructures of the patient's brain.

In an example embodiment of the present invention, once the desired VOA has been received, created, or validated, the system is configured to determine (e.g., using an algorithm and based on a given leadwire location relative to the desired VOA and relative to various anatomical structures) optimal programming parameters to obtain a VOA as close as possible to the desired VOA (e.g., with minimal side effects). For example, the system may analyze different therapy parameters, such as electrode or leadwire location, configuration, shape, etc., or stimulation settings or parameters, in order to produce the desired or target VOA. In an example, the clinician programmer system is configured to compute optimal therapy parameters using the 3-D rendering, and is configured to display the calculated optimal electrode configuration or the calculated optimal resulting VOA from the calculated optimal therapy parameters using a display device. In an example, the calculated optimal VOA can be compared to the desired or target VOA.

In an example embodiment, for a desired or target VOA, the clinician programmer system is configured to display, for selection by a clinician or other user, one or more calculated therapy parameter options corresponding to respective VOAs determined to be close to the target VOA. In this regard, it is noted that the exact target VOA may not be obtainable. In an example, the desired or target VOA can be compared against the VOA computed for a particular parameter set. For example, for a suggested parameter set, the system may display the estimated VOA corresponding to the parameter set overlaid on the target VOA.

Alternatively, the system may be configured to automatically set the determined optimal parameters.

In an example embodiment, the clinician programmer system is configured to compute a score for a VOA computed for a parameter set in relation to the desired or target VOA. In certain examples, the scoring can be based on the amount of the desired or target VOA encompassed by the computed VOA, the amount that the computed VOA exceeds the desired or target VOA, the predicted or past side effects or efficacy of at least a portion of the computed VOA in the patient or other patients, etc., or a combination of one or more of the scoring options shown above or other scoring options.

In an example embodiment of the present invention, a secondary prediction of outcome, such as positron emission tomography (PET) scan, can be used to determine optimal therapy parameters. In an example, these secondary predictions can be performed following or in conjunction with test stimulations, entered into a database in relation to the respective therapy parameters, and be included as part of the scoring factor for possible VOA calculations.

Prediction Algorithms

In an example embodiment, the system is configured to compute a score for one or more possible VOAs (e.g., a score can be computed for every possible VOA, such as by computing a score for each possible variation in each therapy parameter) in relation to the desired or target VOA. However, computing a VOA for each variation in each therapy parameter can take a large amount of time and processing power. In order to alleviate these and other issues, embodiments of the present invention provide a predictive algorithm for computing optimal parameters for a desired or target VOA.

In an example embodiment of the present invention, the clinician programmer system is configured to compute an estimated VOA for each variation of separate therapy parameters (e.g., for each stimulation parameter variation; such as a range of stimulation amplitude, frequency, pulse-width, duty cycle, etc.; a change in leadwire location or electrode configuration; and/or other therapy parameter).

In an example embodiment, one or more computed and/or actual VOAs from the patient or other patients are recorded or stored, e.g., in relation to leadwire placement, electrode location, and/or parameter settings, as a library of computed and/ or actual VOAs. Thus, once a leadwire has been implanted, the possible VOA at that leadwire location, electrode selection, and/or parameter setting(s) can be predicted or shown using the library of recorded or stored computed VOAs from the same or similar leadwire location, electrode selection, and/or parameter setting(s). As such, a VOA can be predicted using the therapy parameters from the previously computed or actual VOAs.

For example, using the library of computed VOA, a look-up table is created. This look-up table may be used to pull-up a VOA based on user selected therapy parameters. Also, the look-up table may be used to determine therapy parameters. Further, the library of computed VOA may be used to develop one or more general relationships for estimating a range of VOAs using one or more computed VOAs.

For example, for a given set of therapy parameters, a set of computed VOAs can be created for the complete range of varying pulse width (e.g., 100 computations, from a duration of 1% of the period, each computation increasing by 1% to a duration of 100% of the period). In an example, a relationship can be developed illustrating the effect to the computed VOA for each variance. In an example, the relationship can be developed using information from one or more patients, models, etc. In an example, the developed relationship can be used as a predictive algorithm. Thus, a database can be computed using one or more relationships or predictive algorithms to determine an optimal set of therapy parameters for a desired or target VOA.

In an example, a predictive algorithm can be created for varying therapy parameters, such as electrode or leadwire location, configuration, shape, etc., or stimulation settings or parameters. For example, an equation relating various parameters to predicted VOAs may be generated as described in more detail below.

In an example embodiment of the present invention, the database of developed relationships or predictive algorithms are updated with every actual computation, and can be used in order to compute optimal therapy parameters for a desired or target VOA without separately computing every varying possible VOA.

In an example, for a given target VOA (e.g., input by a user), a small number of actual computations (e.g., one, two, or more computed VOA using varying test therapy parameters) can be performed, and, using the database of predictive algorithms, be correlated or best fit to previous computations to find the estimated optimal therapy parameters.

VOA Estimation and Equation Generation for Monopolar VOA Estimation

In an example embodiment of the present invention, the system may calculate a VOA for a monopolar electrode configuration, where the current source is from one or more contacts on the DBS leadwire and the ground is at a casing of an IPG located some distance from the DBS leadwire. In an example embodiment, for the calculation of the VOA for a monopolar electrode, the system and method may model an area of a patient, e.g., an area of the brain of the patient; model voltages at various points within the patient model; model axons within the patient model; model a waveform for a given set of DBS parameters; determine the voltage at various points along the model axons due to the axon's location relative to the electrodes; determine for the modeled waveform the injected current amplitude required for axon activation at the respective axons' modeled voltages; determine which axons of the model will be activated based on whether the amplitude meets the required thresholds of the respective axons; and generate a representation of an area formed by the axons that the system and method determined will be activated. In this regard, in an example embodiment of the present invention, the threshold current amplitude value required at an axon is calculated based on a second order derivative of the voltage, so that a rate of change at a point in space determines whether a neuron is activated. In other example embodiments, other methods may be used to determine the required threshold current amplitude values.

In an example embodiment of the present invention, for the calculation of the VOA for a monopolar electrode, the system and method may initially calculate a plurality of VOAs for various sets of DBS parameters as in the previous paragraph. Based on the data obtained from the generation of the VOAs for the sets of DBS parameters, the system and method may determine a function whose input are the DBS parameters and whose output is the necessary voltage values required for firing of an axon at the input DBS parameters. Subsequently, the system and method may, for a further set of DBS parameters, model the voltages and axons in the patient model and determine the isosurface, i.e., the boundary surface of axons predicted to be activated, and, thus, the VOA, based on the determined function.

Figure 13A:
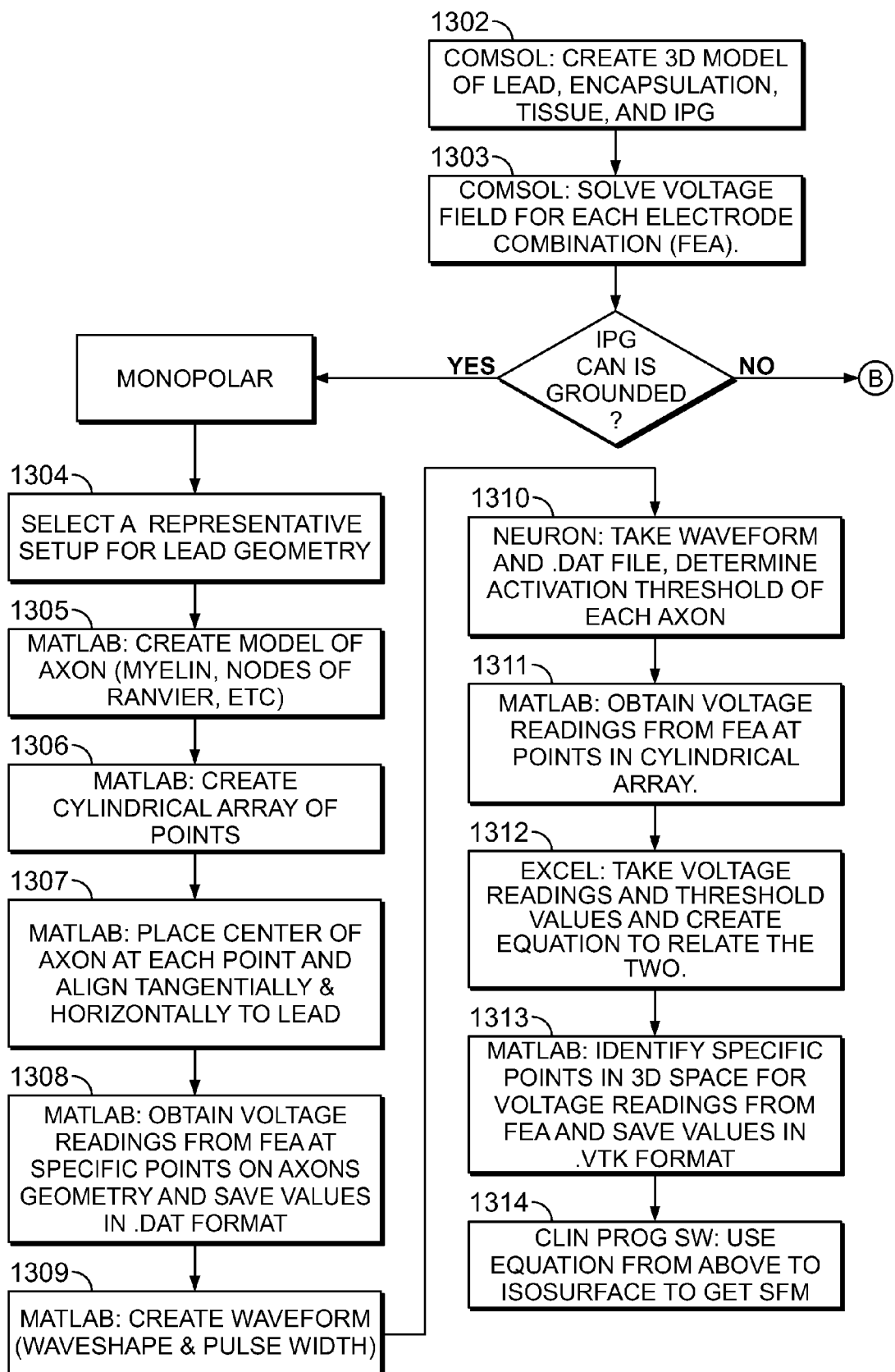
FIGS. 13A-13B show a flowchart that illustrates methods of generating VOAs in monopolar and bipolar cases, according to example embodiments of the present invention.
Figure 13B:
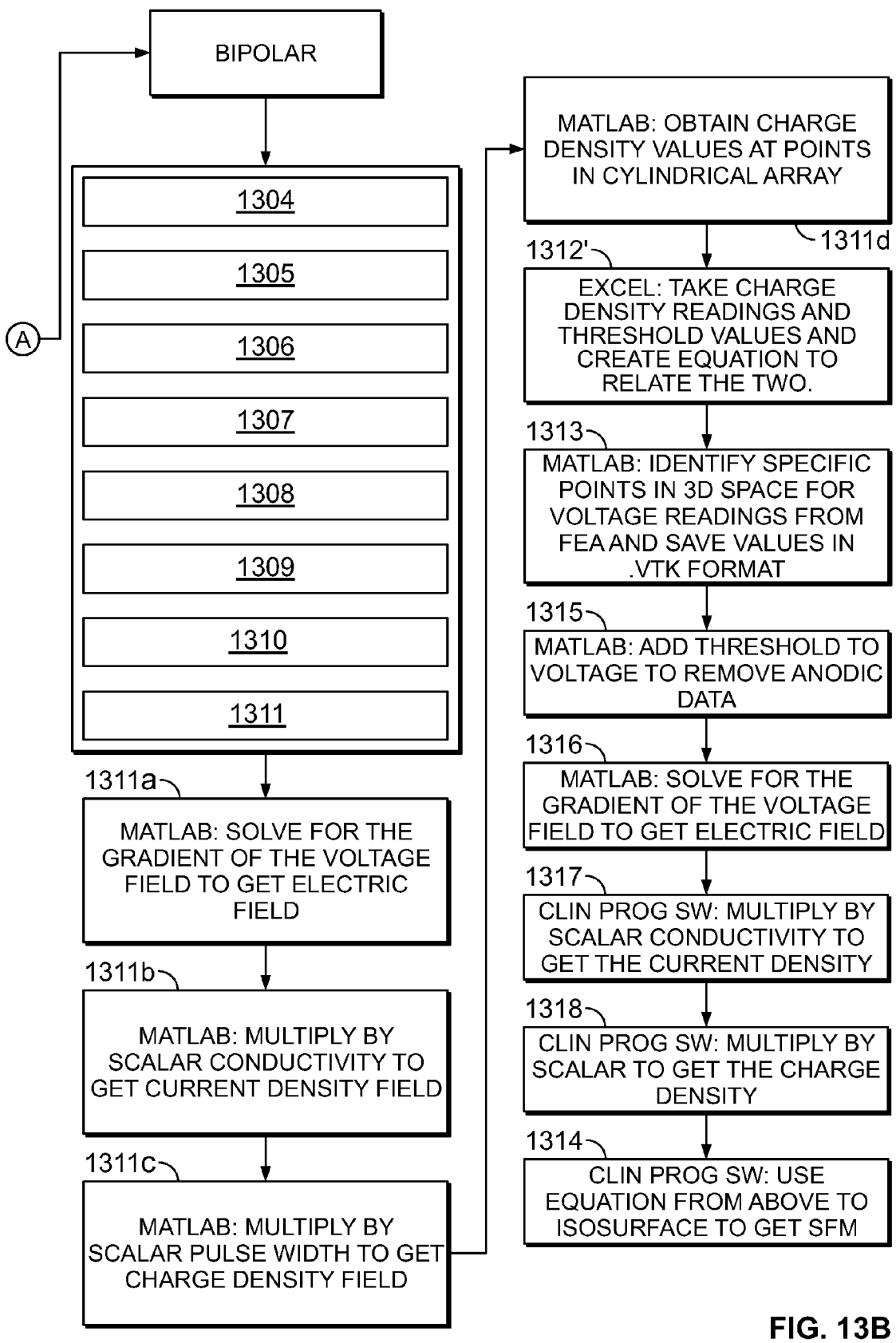

FIGS. 13A-13B show a flowchart that includes an illustration of an example method for calculation of a VOA for a monopolar electrode (see FIG. 13A). At step 1302, a Finite Element Analysis (FEA) program, e.g., Comsol, may be used to create a 3-D model of the stimulation electrode leadwire, an encapsulation layer that defines an area in which scar tissue generally forms after insertion of the electrode leadwire, tissue, and the IPG. At step 1303, the FEA program may be used to solve a voltage field for the given electrode contact combination. In this regard, a number of electrode contact combinations may be implemented independently, and for each combination, the FEA program may solve a respective voltage field. For example, a different number of electrode contacts may be activated in different setups.

The FEA program may set up a large series of differential equations defining the voltage in the region surrounding the electrode. The setup may assume a 500 μm encapsulation layer surrounding the electrode. The conductivity of this layer is changed to simulate brain tissue with higher or lower impedance. In this regard, the impedance of the encapsulation layer is different from patient to patient and session to session because it is based on the immune reaction of the body. The encapsulation layer is a result of the body's natural tendency to form scarring around the foreign body (the lead in this case) and differs from person to person. Based on clinical studies, the impedance of this layer has been determined to vary such that it is, in an example embodiment of the present invention, variably modeled as low, medium, and high. The system impedance can be read in real-time and the model used to determine the voltages can be adjusted accordingly. In an alternative example embodiment, calculations are obtained for conductivity related to all three impedance values, i.e., low, medium, and high.

At step 1304, one of the electrode contact combinations is selected as representative of the leadwire geometry. An example leadwire geometry may that of a leadwire that has: a length of 10-50 cm; a straight shape; a body diameter of 1.27 mm; an in-line connector; and four electrodes of cylindrical shape that are each 1.5 mm in length and that are spaced from each other by 0.5-1.5 mm. That is, although voltage fields for a number of electrode contact combinations may be initially determined for an electrode geometry, in an example embodiment of the present invention, only one voltage field is fed to a neuron simulation program for an initial threshold determination as described below. Subsequently, an equation may be used for finding the thresholds for the other voltage fields of other electrode contact combinations of the electrode geometry, as described below.

The voltage field calculated for the selected electrode contact combination may be provided to a matrix solver, e.g., Matlab. At step 1305, the matrix solver may create an axon model, indicating points along its length which correspond to myelin, nodes of Ranvier, etc. At step 1306, the matrix solver may create a cylindrical array of points. At step 1307, the matrix solver may, for each point of the array of points, place an instance of the modeled axon with its center at the point of the array. The resulting array of axons may be placed tangentially and horizontally to the modeled lead. At step 1308, the matrix solver may save in a .dat format the voltage values of the FEA obtained for the selected electrode contact combination at the points along the axons arranged about the lead.

At step 1309, the matrix solver may create a waveform for a pulse of the DBS electrode. The waveform may have features including a wave-shape (e.g., square, sine, or triangle) and a pulse width. For example, the various pulse width values may be selected at predefined increments. The waveform may be dependent on currently set parameters. The waveform may vary depending on the specific IPG used. Exemplary wave shapes which can be applied include triangle, sine, square, Gaussian, etc., different ones resulting in different VOAs. In an example embodiment, the overall shape may be first selected, and then the shape can be modified to change the pulse width, amplitude, etc. Difference equations may be determined for difference wave-shapes. For each wave-shape, the pulse width may be varied for the various waveforms.

At step 1310, a program that simulates neurons, including ion channels, membrane properties, and other relevant properties to depict neural responses, e.g., Neuron, a non-proprietary program developed by Duke University and Yale University, determines an activation threshold of each of the modeled axons and associated voltages of the .dat file based on the waveform created by the matrix solver. For example, the system and method may determine a required amplitude for activation of an axon given the voltage values determined along its length, by varying the waveform amplitude to determine the threshold at which each axon fires.

In an example embodiment of the present invention, the threshold values for a given set of electrode parameters may be compared to the voltage values at the locations of the modeled axons in the generated anatomical patient map to determine the cutoff boundary for axon activation. The system and method may visually indicate in a displayed anatomical map the region including the axons that will fire given the input parameters. That is, the determinations may be applied to a structured grid surrounding the lead, so that they are arranged relative to the lead, and the grid may be applied to the patient map.

In an example embodiment of the present invention, the system and method, e.g., via Matlab, may plot the threshold values determined by the neuron simulator at the centers of the modeled axons. At step 1311, the system and method may again take the voltage values at these same points in space at the center of the axons. For determining an equation, the system and method may use the current amplitude threshold values obtained in repeated performance of the above described steps, the different instances of their performance using different pulse width waveforms to simulate stimulation of the neurons, the reactions to the different pulse widths being recorded. Thus, different threshold values may be determined for different waveforms. At step 1312, a curve fitting program, e.g., Excel, may compare the plotted threshold values recorded for the various simulated waveforms to the voltage values at the plotted locations in the modeled axons and determine an equation which relates the two. In this regard, the voltages may be used as representative of how the field falls off relative to the source. For example, an equation of Volt=$(C_1^2*PW+C_2*PW+C_3)*Amp^{(C_4^2*PW+C_5*PW+C_6)}$ may be determined, where Volt corresponds to the voltage threshold, Amp corresponds to the desired current or voltage amplitude being sent through the electrode, PW is the pulse width of the waveform, and $C_{1-6}$ are coefficients to fit the given leadwire type and/or wave-shape. Thus, between various determined equations, the coefficients $C_{1-6}$ may vary. The above-described process is repeated at least three times, each time with a different impedance level. The coefficient values vary depending on impedance. The variables determined for the curve fitting performed for each of the impedance levels are then further fit to produce an overall function with voltage values on one side and amplitude, pulse width, and impedance on the other side.

Subsequently, for various electrode settings of amplitude, pulse width, and impedance, the voltage at which an axon fires may be determined directly from the determined function. At step 1313, the system and method, e.g., via Matlab, may record the voltage readings at specific points from FEA and save values in a new format. The clinician programmer system may, at step 1314, apply the calculated function of voltage vs. amplitude/pulse width/impedance to the voltage values of the .vtk file to obtain an isosurface of the cutoff boundary for axon activation, the area within the boundary being an activated region. Accordingly, while only a single representative electrode contact combination was selected for determining the threshold values, the threshold values for the other combinations (of the same electrode geometry) may be determined based on the calculated function.

VOA Estimation and Equation Generation for Bipolar VOA Estimation

In an example embodiment of the preset invention, the system may calculate a VOA for a biopolar electrode configuration, where the current source is from one or more contacts on the DBS leadwire and ground is at another one or more contacts of the DBS leadwire. In an example embodiment, for the calculation of the VOA for a bipolar electrode, the system and method may initially calculate a plurality of VOAs for various sets of DBS parameters for a monopolar electrode. However, instead of pairing wave amplitude thresholds against voltages, as described above, the system and method may obtain an electric field based on the gradient of the modeled voltage field, multiply the electric field by a scalar, representing tissue conductivity, to obtain a current density field, multiply the current density field by a scalar, representing pulse width, to obtain a charge density field, and then pair the amplitude thresholds against the charge density values. A function may then be obtained as described above, except that the function's output is the necessary charge density value required for firing of an axon at the input DBS parameters. The system and method may then, in the bipolar case, scale down or remove anodic values and obtain a charge density field as in the monopolar case. The system and method may determine for each modeled axon whether it will fire by input of the corresponding charge density values into the determined function, thereby obtaining an isosurface and VOA.

The flowchart of FIGS. 13A-13B also illustrates an example method for calculation of an SFM for a bipolar electrode (see FIG. 13B). The process may begin with performing a modified version of steps 1302-1313 for a representative monopolar geometry and electrode contact combination. The modified version may include, steps 1311a-1311d and 1312'. At step 1311a, the system and method, e.g., via Matlab, may determine an electric field based on the determined voltage field. At step 1311b, the system and method, e.g., via Matlab, may multiply the electric field values by a scalar (e.g., representative of tissue conductivity) to obtain a current density field. At step 1311c, the system and method, e.g., via Matlab, may multiply the current density field by a scalar (e.g., representative of the pulse width of the presently considered waveform) to obtain a charge density field. At step 1311d, the system and method, e.g., via Matlab, may map the charge density values at points in the cylindrical array of points of step 1306.

At step 1312', a curve fitting function may be used as described above to obtain an equation. This equation may differ from the equation described above with respect to 1312 in the monopolar case, in that this equation may solve for charge density values rather than voltage values. (It is noted that this equation may also be usable for solving for a VOA in the case of a monopolar electrode configuration.) At step 1313, the system and method, e.g., via Matlab, may record voltage readings at specific points in 3-D space from FEA and save the values, e.g., in a new format.

After a voltage field is obtained for the bipolar geometry, e.g., as described with respect to the monopolar geometry (this step is not shown), the system and method, e.g., via Matlab, may, at step 1315, threshold the voltage values obtained for the bipolar geometry to scale down or remove anodic data. At step 1316, the system and method, e.g., via Matlab, may solve for a corresponding electric field by taking the spatial gradient. At steps 1317-1318, the clinician programmer system may obtain charge densities as described above with respect to steps 1311b-1311c. At step, 1314, the clinician programmer system may use the charge density function to obtain a charge density threshold value (also referred to as an isosurfacing value) and apply the threshold value to the charge density values of the bipolar geometry, thereby creating an isosurface at the threshold level. In this instance, the step 1314 may be applied to the charge density field rather than the voltage field.

Thus, VOAs are created in distinct ways for the monopolar and bipolar cases in example embodiments of the present invention. The monopolar method provides for estimating the results from an array of model neurons in a voltage field. Due to the large voltage gradient, this method may be difficult to implement in the bipolar case. Instead, in the bipolar method, the voltage data is transformed into a charge density vector field and then has a threshold set.

Details Regarding the Monopolar and/or Bipolar Configurations

In either case, creating VOAs may start in Comsol or another FEA program. First, a three dimensional model is created, including the leadwire, an encapsulation layer surrounding the lead, brain tissue, and the IPG. The conductivity of the encapsulation layer is changed to simulate brain tissue with higher or lower impedance and the combination of contacts which are to be active is chosen. The differential equations inferred by these geometric properties yields a description of the voltage field emitted into the simulated brain tissue. This FEA voltage field is output from the program and used several times later on.

Figure 14:
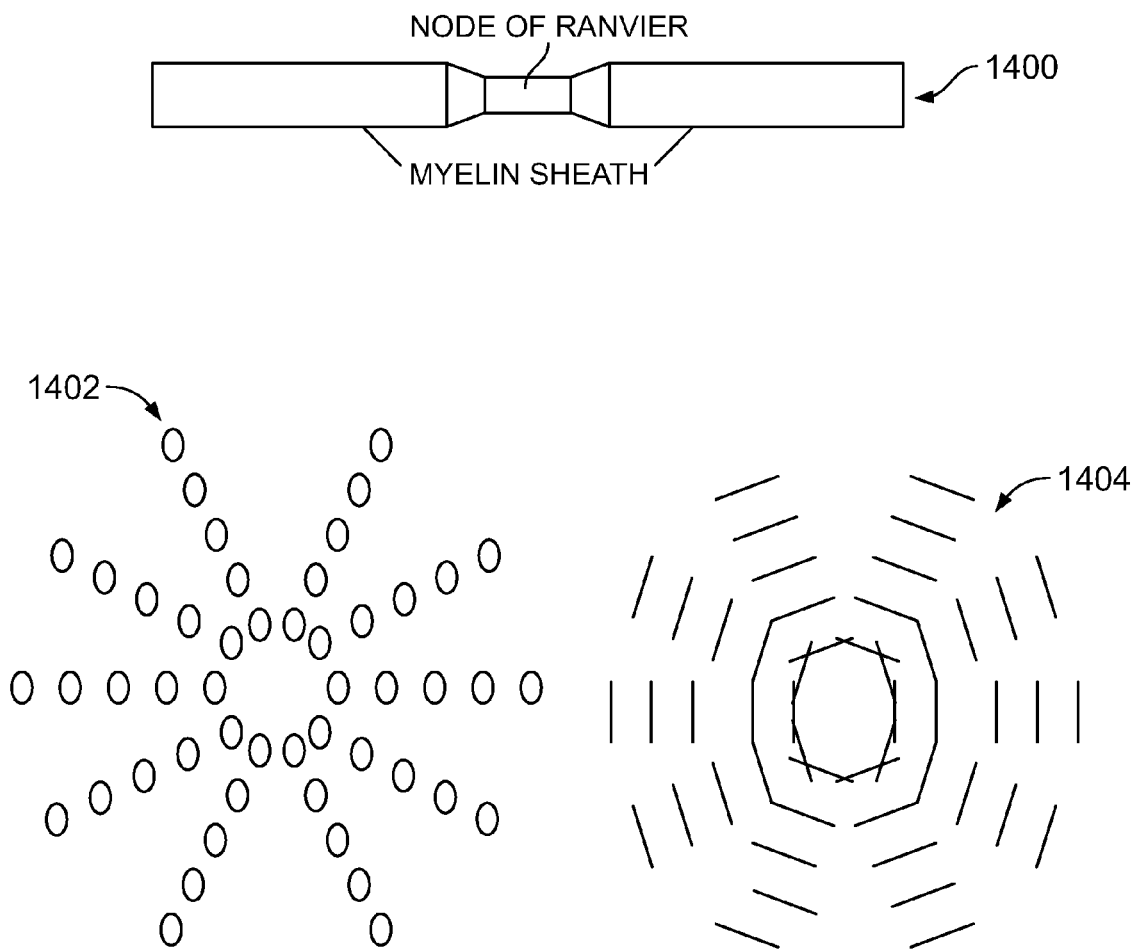
FIG. 14 illustrates models of an axon, an array of points, and application of the model axon to the array of points, according to an example embodiment of the present invention.

The next step in a monopolar scenario is to set up an arrangement of model axons. Their location is defined, for example, in Matlab. First, the spatial separation of important locations (e.g., the nodes of Ranvier, myelin sheath, etc.) is defined for a single axon. Second, a cylindrical array of points is spatially defined. Then, these two are combined so that the points in space are set as the center of each axon, which are then aligned horizontally and tangentially to the lead. FIG. 14 shows an example model axon 1400, cylindrical array of points in space 1402, and application of the model axon to the array 1404. This gives a set of points in space at which the voltage values are relevant. The system and method, e.g., via Matlab, then obtains these values and saves them as a .dat file. In addition to this, Matlab may be used to create a waveform for the run with a given wave shape and pulse width.

Next, Neuron, for example, takes into account the waveform and the .dat file and determines the stimulation amplitude at which each axon will fire. Each of these thresholds is plotted at the center of the axon, thus giving a value to each of the points on the cylindrical array. However, since a single run can take more than six hours, in an example embodiment, this is not done for every possible combination of electrodes, sources, etc. Instead, the original voltage field is isosurfaced at a level determined by a single selected representative electrode contact combination.

In order to generate the equation relating the voltage fields to the Neuron thresholds, voltage values need to be taken which correspond spatially to the thresholds. Matlab, for example, is again used, this time to find voltage values at the points defined by the above cylindrical array. Each of these data points is paired with the threshold data from the same point in space. Curve fitting in Excel can be used to obtain an overall equation to relate these pairs. This process is repeated for a range of pulse widths (changed in the waveform) and tissue impedances (changed in Comsol).

The clinician programmer system will read this data from a library of these voltage fields. Each combination is obtained by having voltage read at given points in space from the FEA and the resulting set of data saved in a .vtk file. The clinician programmer system then inputs the impedance, pulse width, and current amplitude into the equation and uses the resultant voltage value to isosurface the chosen voltage field and produce a VOA. All of the area within this isosurface is thus said to be activated as the VOA.

Figure 15:
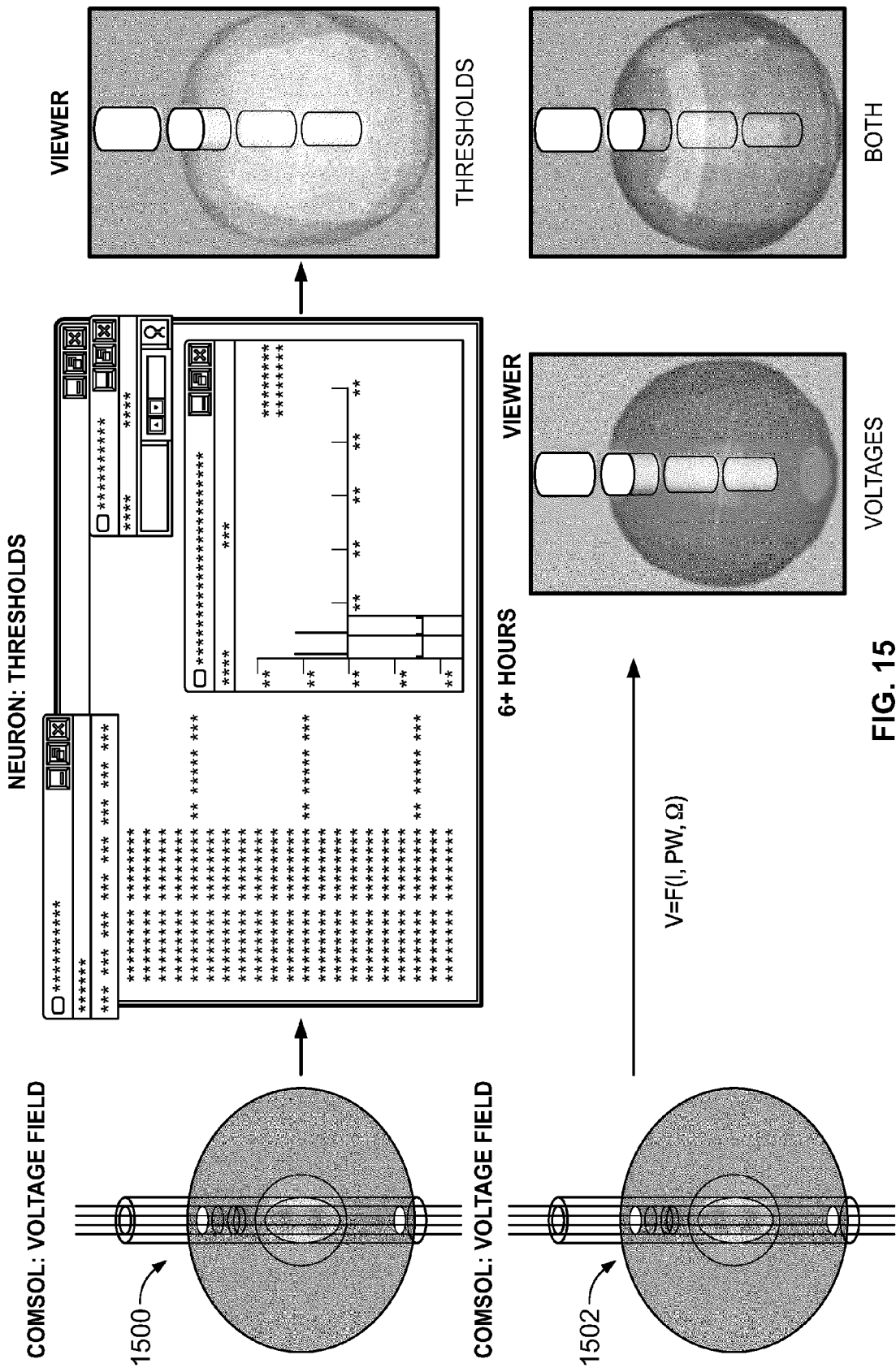
FIG. 15 illustrates passes in which SFMs are generated for the monopolar case, according to an example embodiment of the present invention.

FIG. 15 illustrates the two passes for generating VOAs. In a first pass 1500, Neuron, for example, is used to directly obtain threshold values for a selected representative electrode contact combination, which is then used to obtain a function which is used in subsequent passes 1502 to obtain the VOAs for other amplitude, pulse width, and impedance settings.

Further, the same equation can be used for voltage fields of various electrode contact combinations using the same leadwire.

In the bipolar case, the next step is to obtain the voltage values at the points along the same cylindrical array using, e.g., Matlab. This must be done with a selected representative monopolar electrode contact combination in order to get another equation. A script is run which calculates the second spatial derivative, which gives the gradient of this field, producing the electric field. The electric field is then multiplied by the tissue conductivity to obtain the current density and then the pulse width to get the charge density. The charge density values are then recorded at the same spatial points and again, Excel, for example, is used to compare them to the activation thresholds obtained from, e.g., Neuron in the previous step of the monopolar case. This results in an equation which takes as input the amplitude, pulse width and impedance and gives the correct current density value.

Once this equation has been identified, a library of current density fields may be created for various additional electrode contact combinations. For each of the additional electrode combinations, the voltage field is again saved from the FEA and the gradient obtained in Matlab. This is multiplied by the conductivity, which is the same in every case, and these current densities are saved. The clinician programmer system then opens the correct library entry, multiplies it by the desired pulse width and uses the equation to determine the isosurface value and create the VOA.

Figure 16:
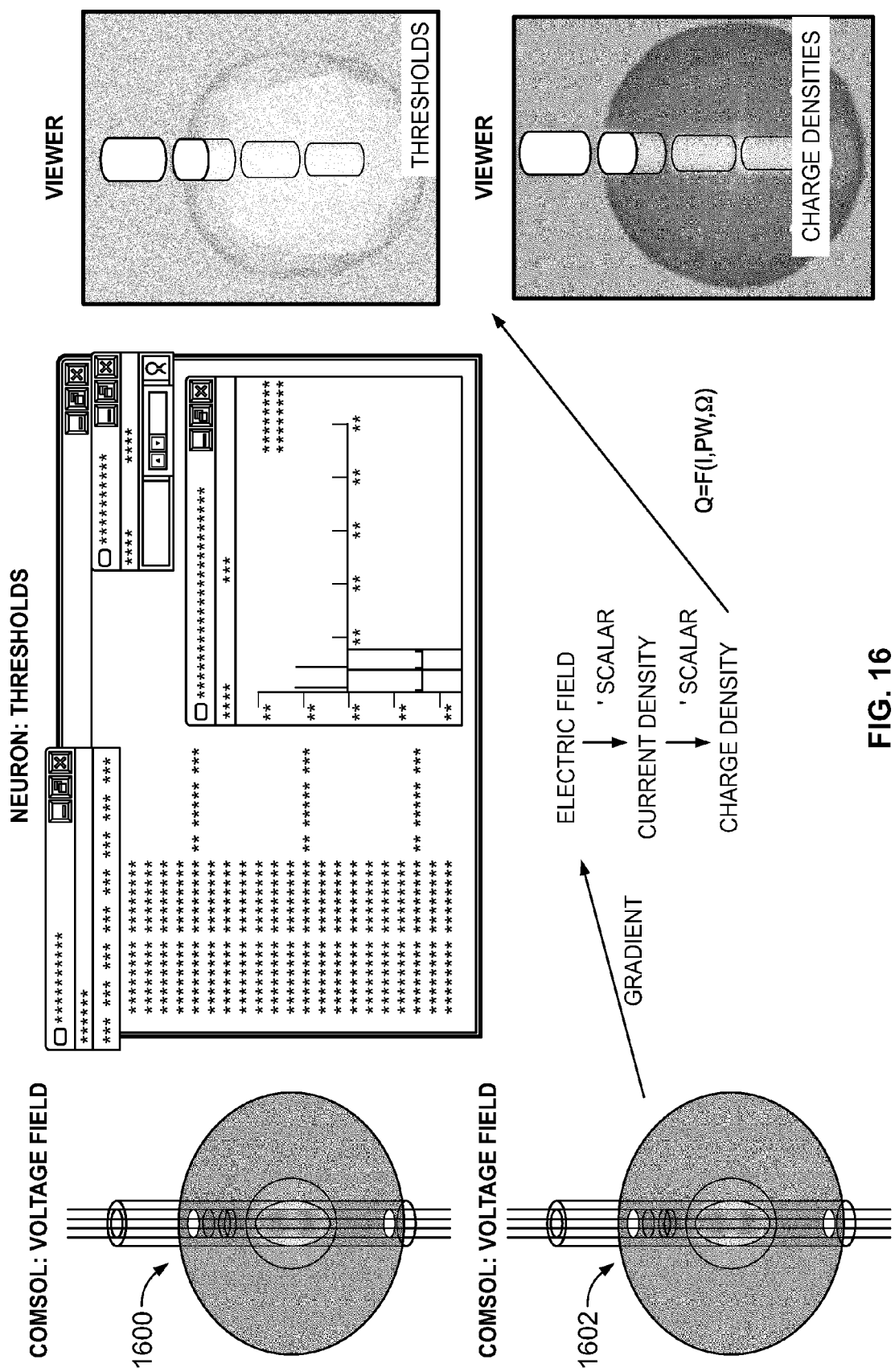
FIG. 16 illustrates passes via which SFMs are generated for the bipolar case, according to an example embodiment of the present invention.

FIG. 16 illustrates the described method for generating VOAs in the bipolar case, which method includes a first pass 1600 using Neuron to obtain thresholds for a representative monopolar case and subsequent passes 1602 using an equation to obtain the thresholds for the bipolar case.

Highlighting of Overlapping Areas Between VOA and Structures

Figure 3E:
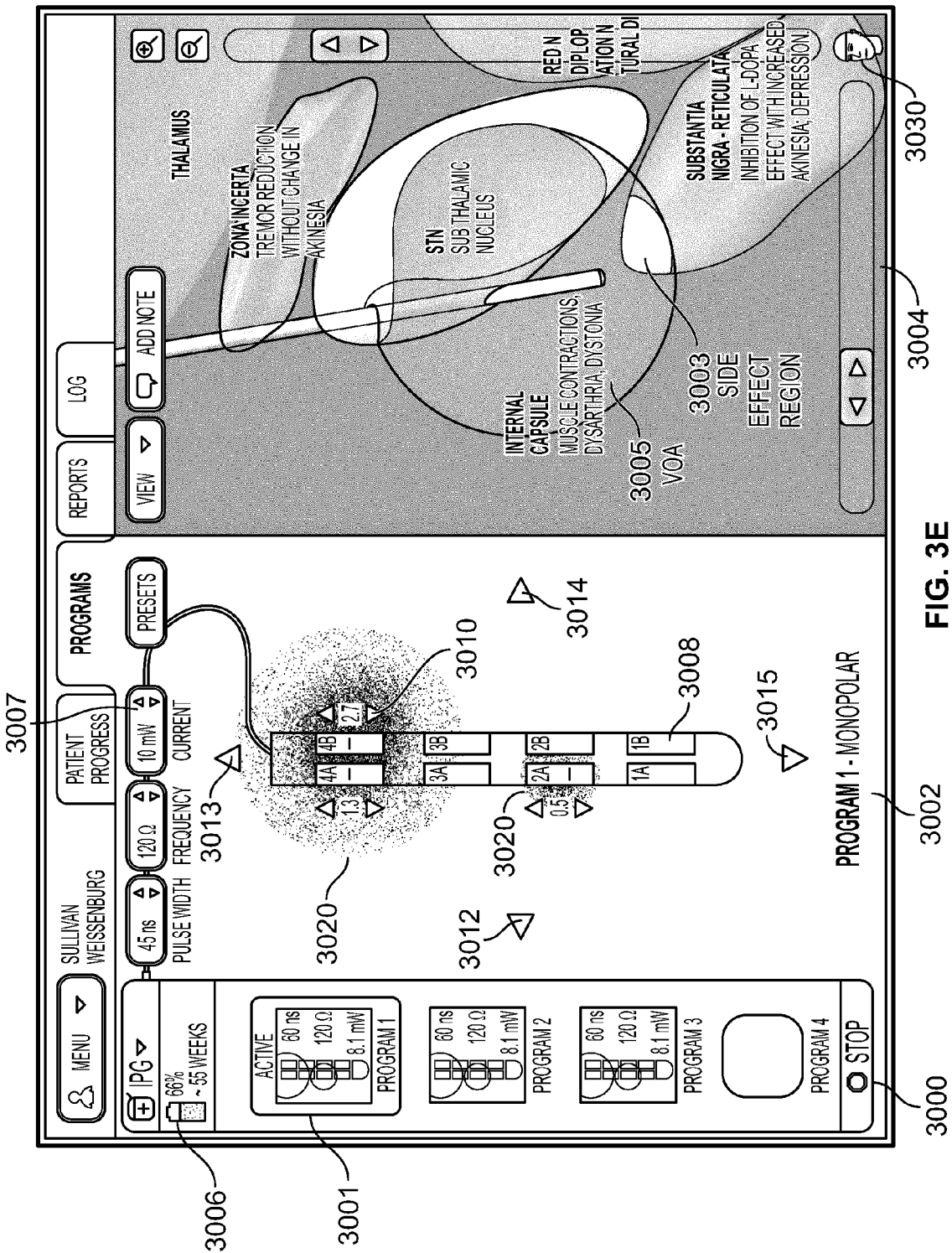
Figure 3F:
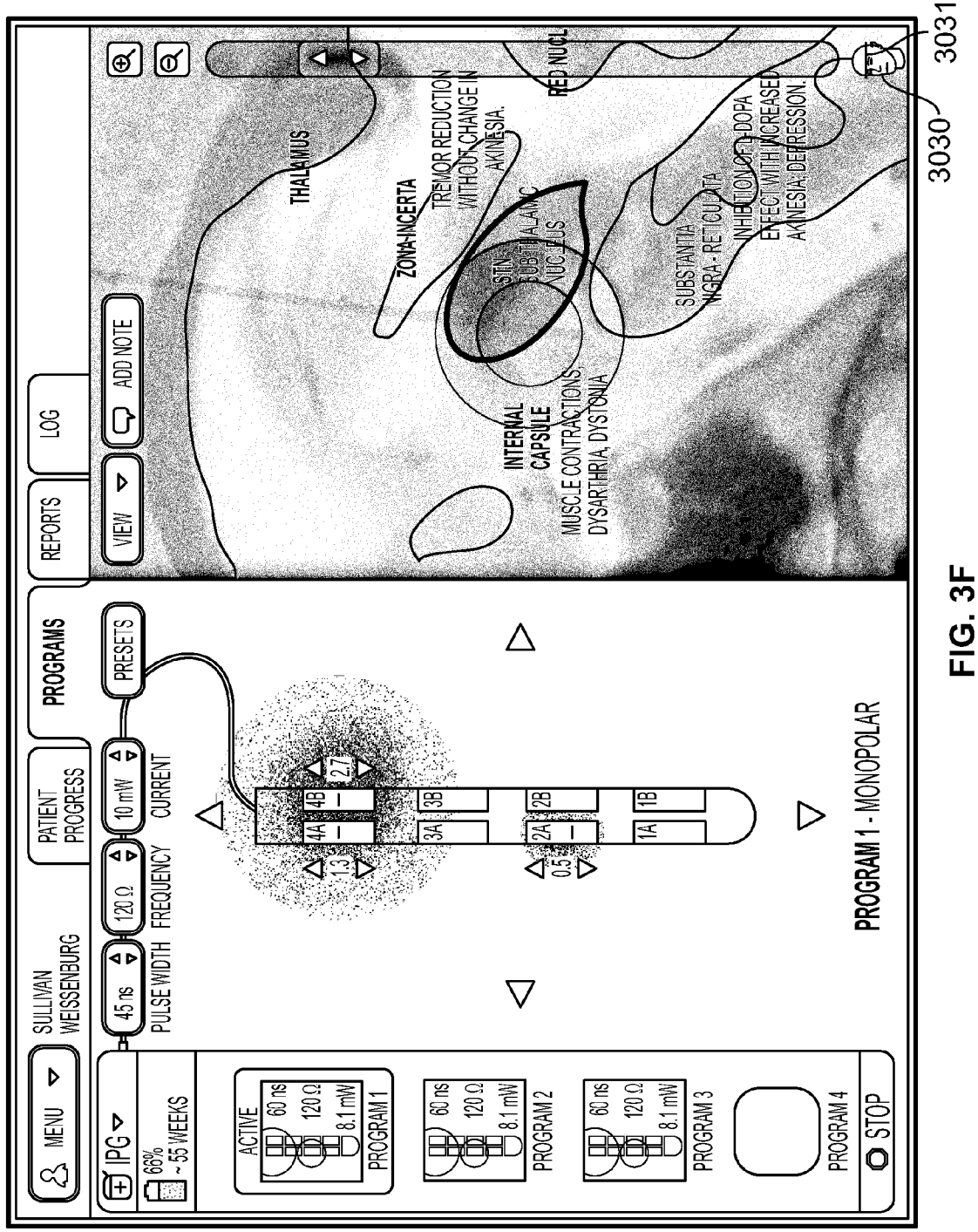

The right window, partition, or frame of FIGS. 3e-3f illustrates generally an example of a display which may include a two or three dimensional rendering. In an example, this window, partition, or frame can be configured to display a number of different images (e.g., a Computer Tomography (CT) Scan; a Magnetic Resonance Imaging (MRI); or a Diffusion Tensor Imaging (DTI)); a two or three dimensional anatomical atlas, such as the Schaltenbrand-Wahren Atlas, the Morel Atlas, etc.; a two or three dimensional representation of an implantable lead; and/or a two or three dimensional image of the VOA, etc.).

In certain examples, an anatomical structure or substructure is labeled with the name of the structure, benefits of stimulating the structure, and/or side effects of stimulating the structure. For example, the system may include a database of information regarding various anatomical structures and their associated benefit and/or side effect. The system may determine with which of those structures a VOA interacts and label or otherwise identify the structures according to their associated benefits and/or side effects as determined by access to the database. In an example embodiment, the database may be updated based on user-entered information, e.g., side effect scores entered in a notes feature (discussed in further detail below) in association with particular leadwire settings as shown in FIG. 3h.

In an example embodiment of the present invention, the system is configured to highlight where the VOA overlaps with different anatomical structures or substructures. In example embodiments, the system is configured to highlight or otherwise illustrate the different interactions by different colorings, different shading, hatching patterns, or with other identifying techniques.

In an example embodiment of the present invention, the system is configured to identify overlapping beneficial and/or adverse regions in a similar manner. For example, the system may store information regarding one or more benefits or side effects with respect to structures in an atlas or map, such that when those structures are stimulated, the stimulation may cause certain therapeutic benefits and/or side effects. This benefit/side effect atlas or map can be stored and shown in two or three dimensions. In certain examples, different benefits or side effects can be identified by a display using different color coded structures or substructures, different intensity patterns, different hatching patterns, via text on screen, etc., as shown in FIGS. 3e-3f, in which overlapping areas between a VOA and an anatomical structure or substructure are highlighted in different ways. Specifically, in FIG. 3e, for example, yellow is used to show a side effect region 3003 and dark red is used to show a benefit region.

Such information can be used by the clinician to determine whether an input or otherwise selected parameter set is optimal.

In an example embodiment, the modeling area perspective can be rotated, changed, zoomed, or otherwise altered using one or more inputs or selectors. In an example, the overall perspective of the view in the modeling area can be related back to the patient orientation model 3030 shown as a model of a patient head at the bottom right corner of FIG. 3e. In an example, the patient head or other similar input may be similarly used with respect to the various screenshots shown in FIGS. 3a-3j. In certain examples, the patient orientation model 3030 can be rotated by clicking and dragging, or the patient orientation model 3030 can solely reflect the changes made to the modeling view using other input mechanisms.

In an example embodiment, the system may provide for display of the model, VOA, and structure overlap in a 3-D view and/or in a 2-D view. For example, the particular views may be user-selectable. For example, the VOA may be displayed in a same cross-sectional view of, and overlaying, an MRI cross-section, as shown in FIG. 3f. Moreover, the model atlas structures may be similarly displayed in either a 3-D view or in a 2-D cross-sectional view of, and overlaying, an MRI cross-section and VOA. All such views may further include the overlap highlighting.

In an example embodiment, the system may provide a user interface for receiving user input to scroll between cross-sectional MRI and corresponding VOA and atlas structure views. For example, the patient orientation model 3030 may include a selectable slice bar 3031 which may be dragged axially and/or rotationally, in response to which the system may display a view corresponding to the section of the patient orientation model 3030 to which the slice bar 3031 has been dragged. Alternatively, a different user input may be provided for changing the cross-sectional view. According to this embodiment, the slice bar 3031 may be omitted or may be displayed to provide the user a visual context of the view being displayed.

In an example embodiment of the present invention, the system may be configured to additionally display sagittal, coronal, and axial views.

Notes Feature

In example embodiments of the present invention, a system and method may provide a notes feature which may be used as an aid for selecting an electrode parameter combination. Notes may be entered, which may include information regarding settings, benefits, and/or side effects of a stimulation, and/or other observations or information regarding a stimulation and/or patient.

While a VOA is displayed, a user may input data responsive to which the system creates a new note. The system may display an icon representative of the note in a location that visually indicates and corresponds to a VOA to which the note corresponds. The note may be displayed at the location even after the VOA is removed from display and even while a different VOA is displayed. Many notes, for example where each is associated with a different VOA, may be simultaneously displayed so that a user can quickly associate the various notes with their respective VOAs. In an example embodiment, the system may alternatively or additionally automatically generate a note, e.g., where a side effect and/or benefit associated with a stimulation is detected.

Figure 3G:
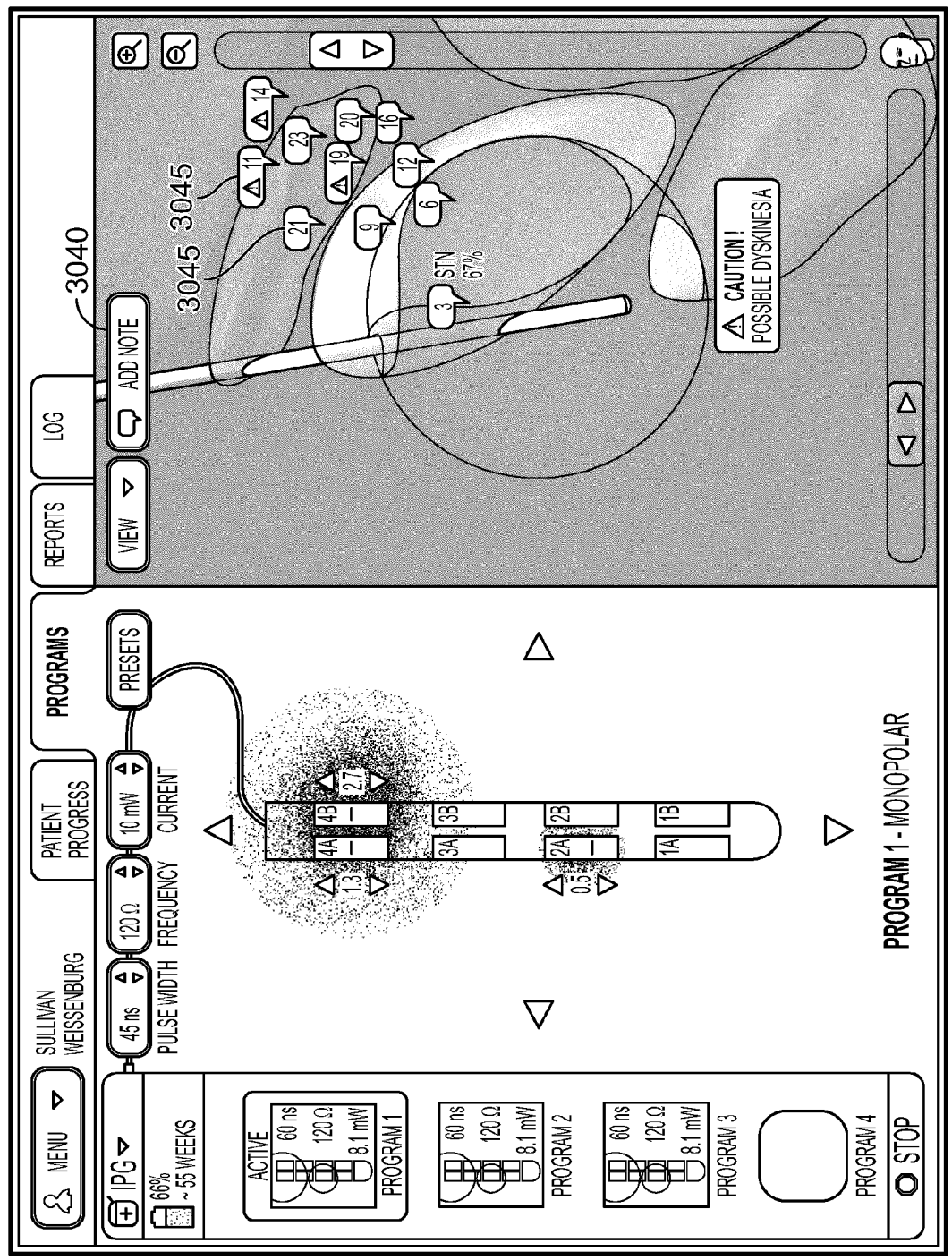
Figure 3H:
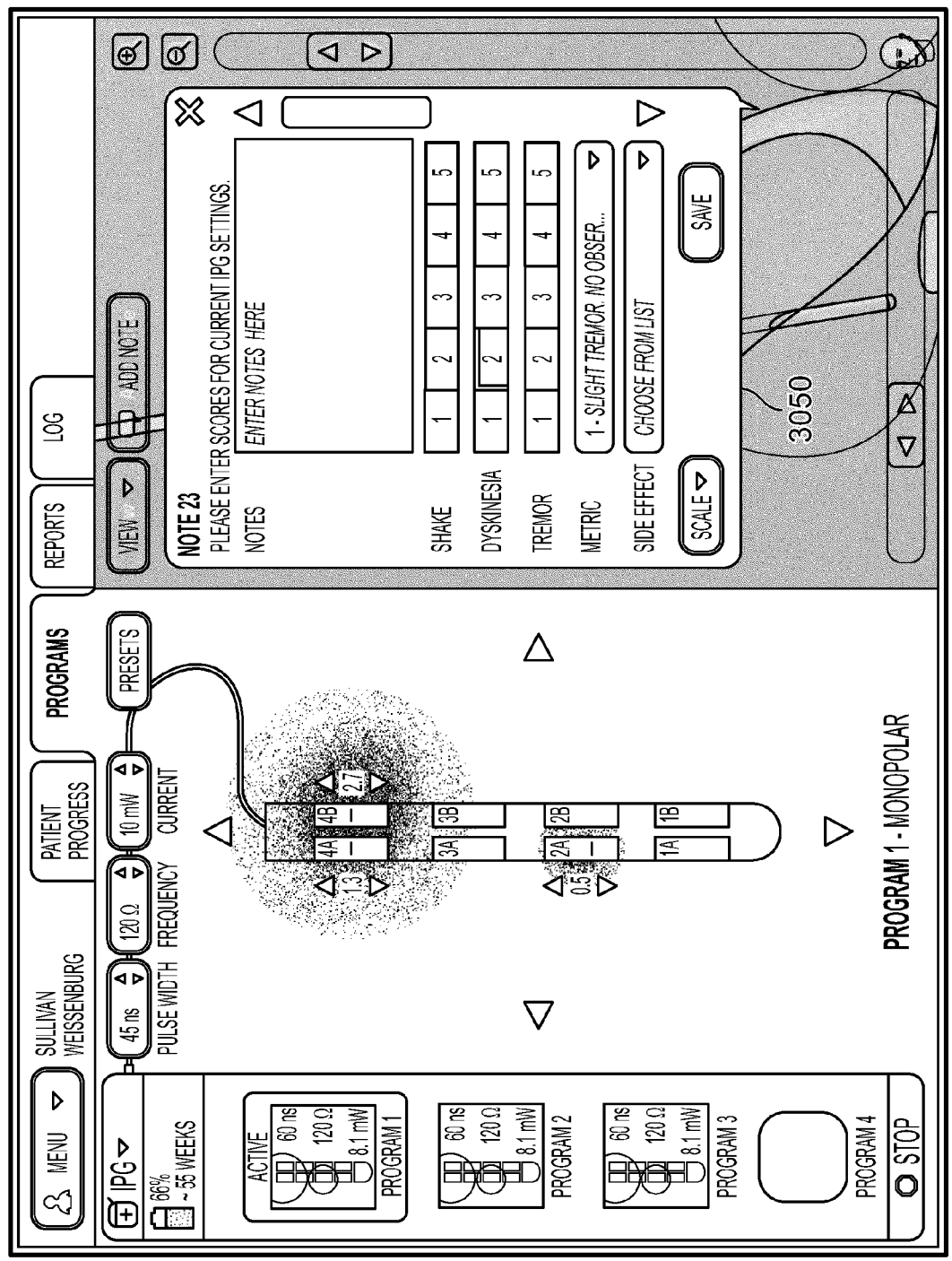

FIG. 3g is a screenshot according to an example embodiment of the present invention. The screenshot includes a right portion or frame in which a generated VOA is displayed in an anatomical patient map, such that the VOA is shown to overlap certain anatomical features. The screenshot includes an "Add Note" button 3040. A user may select the button 3040, for example, by operating an input device, such as a mouse to move a graphical pointer to a location overlying the button 3040, and by pressing a mechanical button, e.g., of the mouse, while the pointer is displayed in that position, or a touch screen. In response, a user-interactive note entry form 3050 may be displayed, e.g., as shown in FIG. 3h, via which a user may enter the substance, e.g., text, of the note. Upon saving of the note, the system and method may automatically append an icon 3045 representative of the note to the VOA map at a location corresponding to the VOA for which the note was created (the VOA displayed when the note was added). For example, a system and method may display the note icon 3045 at a location in the anatomical map which coincides with a point on the outer boundary of the VOA. In an example embodiment of the present invention, a plurality of notes may be input for a single VOA.

Figure 3I:
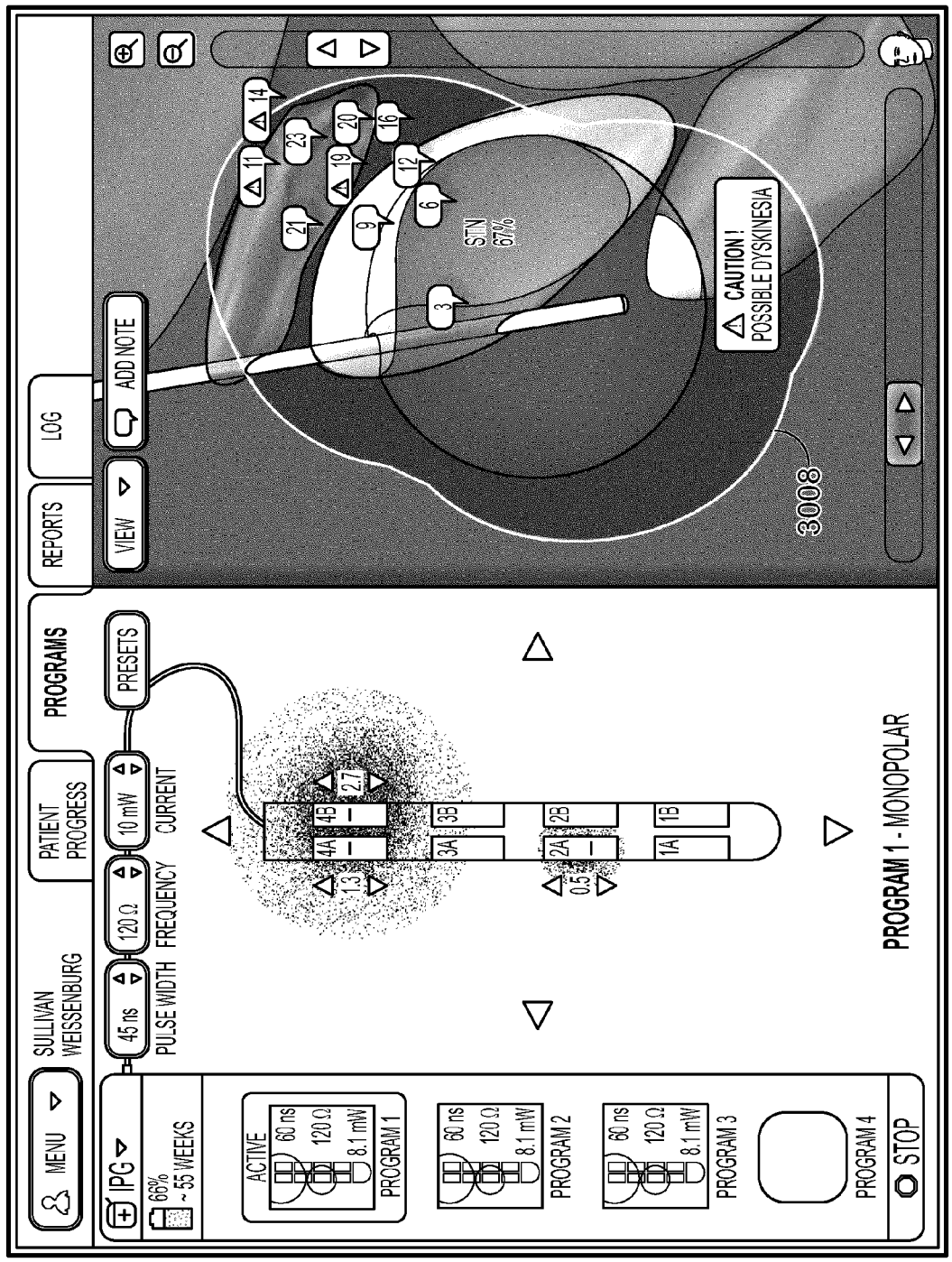

Over time, a plurality of notes may be appended for a plurality of VOAs. In a selected view, although only one VOA is displayed, e.g., the latest generated VOA, icons 3045 representative of notes associated with all of the previously generated VOAs (or a selected subset of the previously generated VOAs) may be simultaneously displayed, each icon at a location that coincides with a point on the outer boundary of the note's corresponding VOA, e.g., as shown in FIGS. 3h and 3i. A system and method may accordingly visually indicate the VOAs with which the various notes are associated. Further, note icons 3045 may be displayed in different colors to indicate whether the VOA to which the note icon corresponds is associated with a side effect or a benefit. For example, certain ones of the note icons 3045 in FIG. 3g are yellow to indicate that the respective note icon corresponds to a VOA associated with a side effect. Alternatively, other visual differences between the note icons, such as with respect to hatching, shading, transparency, shapes, etc., may be used.

Further, the note icons may be selectable, in response to which selection, the system and method may display the associated note. The user may accordingly, quickly view notes and visualize the VOAs with which they are associated, to obtain a quick VOA history. The VOA history may include VOAs of implemented electrode contact combinations and lead parameters and/or projected VOAs of test combinations and parameters which have not yet been implemented.

Flashlight Feature 2-D and 3-D

In an example embodiment of the present invention, a system includes a two or three dimensional flashlight feature.

In an example, a system is configured to display to a user, in a 2-D or a 3-D visualization, one or more areas of an atlas or other patient model or map (e.g., one or more areas of the MRI and/or CT images or other medical images) that have been stimulated by the VOA and/or for which stimulation has been simulated, for example, an explored region 3060 as shown in FIG. 3i. The display may be of a three-dimensional volume or a two-dimensional slice. Further, the system may provide for selection of predefined views, such as axial, coronal, and/or sagittal. The system may provide for scrolling through image slices in the various views.

For example, an explored region including one or more VOAs corresponding to prior actual or simulated stimulations may be shown. In an example embodiment, the explored region may be presented to distinguish it from the unexplored region using shading, color, or one or more other visual effects.

In an example embodiment, a number of VOAs to be represented may be selectable, e.g., the first five, the last five, those corresponding to a specific time period, and/or those corresponding to stimulations having one or more specified parameter values and/or ranges of such values.

In an example embodiment, the explored region can represent a session log, including one or more regions stimulated or simulated in a single or specified multiple sessions of stimulation. In other examples, the explored region can represent a patient history log, including one or more regions stimulated or simulated over a patient's history. In other examples, the explored region can represent a population log, including one or more regions stimulated for more than one patient, such as a patient population. In certain examples, the patients or stimulations included in the session log, the patient history log, or the population log can be selected, sorted, or otherwise indexed according to one or more of patient information (such as physiological status, disease state, age, sex, weight, or other patient information), stimulation information (such as stimulation parameter, electrode configuration, leadwire location, or other stimulation information), and/or other information.

This flashlight feature can allow the user to visually see those areas that have been stimulated (actually or via simulation) in order to aid in selection of electrode and parameter values to provide the best therapy possible for the patient. In an example, the flashlight feature can be configured to display relevant information, while not displaying irrelevant information, or otherwise distinguish relevant information from irrelevant information (e.g., using shading, color, etc.). For example, a user may indicate a particular desired therapy. The system may accordingly identify the areas of benefit for the selected therapy and not benefits for only other therapies. Similarly, the user may indicate certain kinds of side effects that are of concern. The system may accordingly identify only those side effects.

In an example embodiment of the present invention, the notes feature may be available in a display corresponding to the flashlight feature, as shown in FIG. 3i.

Flashlight Side Effect Feature

In an example embodiment of the present invention, the flashlight feature includes a side effect feature or algorithm for determining one or more parameters to quickly reduce parameter space or narrow a side effect profile (e.g., the given side effects for a given stimulation parameter set). That is, it gives a visual representation of stimulation on surrounding tissue.

In an example embodiment of the present invention, a system supports displaying to the user, in a 2-D or 3-D visualization, the areas of the atlas and/or areas of the MRI and CT images (or other medical image) that have previously caused one or more side effects (as determined by the user or other manual or automated process) for the patient. In an example, the area or areas causing a side effect can be displayed visually different from the other areas of the displayed image that are not associated with a side effect(s). In an example, if an area does not have an associated side effect, the "side effect" visual difference can be removed, allowing a user to determine one or more specific areas whose stimulation cause one or more side effects for this patient.

Figure 3J:
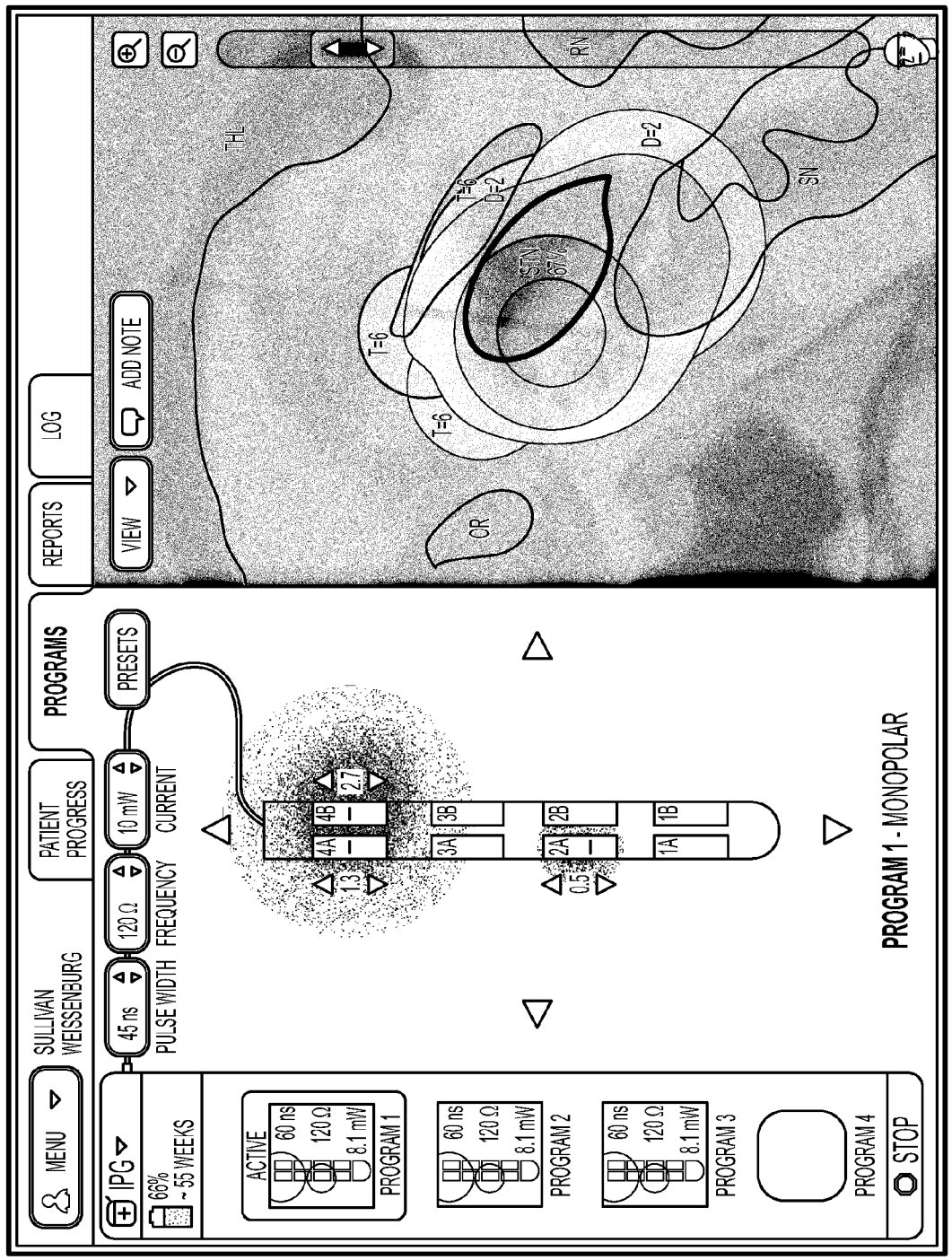

FIG. 3j illustrates generally an example of displaying prior stimulation areas in two or three dimensions as well as indicating (e.g., labeled via color, texture, size, etc.) those stimulation areas that have been associated with one or more side effects. In the example of FIG. 3j, the side effect areas are displayed in yellow outside of the currently represented VOA. The flashlight side effect feature may be on a VOA-basis, as shown in FIG. 3j, such that all areas that have been a part of a present or previous VOA that caused a side effect are highlighted as a side effect area, even if the side effect did not occur in that particular area, unless the area is also associated with at least one other VOA that has not caused any (or significant) side effect. This may be helpful to the user by indicating those areas which may be stimulated without causing a side effect. A user may thereby determine areas in which to avoid stimulation.

For example, if a first stimulation results in a side effect, then the entire corresponding VOA can be labeled, shaded, or otherwise identified using the side effect feature. If a second stimulation corresponding to a VOA overlapping with the first VOA at least in part does not include the side effect, then the area not having the side effect is not labeled, shaded, or otherwise identified as having the side effect. For example, the area not having the side effect, which in FIG. 3j is the demarcated area that is partly bounded by the partial circles labeled with T=6 and/or D=2, is, in an example, shown as gray areas, while the partial circles labeled with T=6 and/or D=2 are, in an example, shown as yellow areas. For example, if the stimulation not having the side effect is modeled after the stimulation having the side effect, the area corresponding to the first modeled stimulation field can be modified so that its shading is removed in that portion at which the second modeled VOA overlaps the first VOA. In various examples, the side effect area or structure can show a single side effect over multiple stimulations, or the side effect area can show multiple side effects over multiple stimulations. In an example, multiple side effects can be recorded for a single stimulation. In certain examples, as overlapping VOAs are recorded, separate or combined side effect areas can be created illustrating areas of stimulation corresponding to a specific or single side effect, or a combination of multiple side effects.

In other examples, a benefit area or structure, or a mold illustrating no noticeable effect can be created in a similar fashion. In an example, at least two of the benefit area, the side effect area, or the area illustrating no noticeable effect can be created or shown.

In an example, for any one or more of the molds, the side effects can be distinguished as having varying levels of effect or severity. In other examples, one or more structures can be identified in relation to a benefit or side effect, in conjunction with, or instead of its anatomical name. In an example, the label (e.g., a color, a shade, etc.) of a structure can be affected by a degree or severity of the benefit or side effect. In an example, the greater the benefit or the worse the side effect, the darker or lighter the color or shading.

In an example, the benefit mold, the side effect mold, or the mold illustrating no noticeable effect can include a patient specific mold, a population mold, or a mold of one or more stimulations from one or more patients.

Time Series VOA

In an example, a VOA is a representation of the volume of tissue that can be activated at a single point in time. In certain examples, the VOA can represent the predicted volume of tissue activated by a waveform with a specified maximum amplitude (e.g., the stimulation waveform). In an example, a biphasic square wave can be applied at a constant frequency. In an example, a therapy may include delivery of stimulation according to different parameters at different pulses. For example, a first frequency and/or electrode combination may be used for a first pulse, and a different frequency and/or electrode combination may be used for a second pulse. In another example, a pattern of varying frequencies that repeats over a certain number of pulses may be used. In another example, the frequency used may be sufficiently high as that an initial stimulation causes the cells to be in an absolute or relative refractory period during the subsequent stimulation and thus vary the VOA over time. Because a pulse generator can be capable of delivering different waveforms at different frequencies in a therapy, it can be difficult to pick a single point along the time series of stimulation at a specific time during the pattern that can be representative of the entire stimulation protocol for creation of a VOA.

In an example embodiment of the present invention, a Time Series VOA feature is provided that allows a user to cycle (automatically or manually) through a sequence of patterns to show the potential VOA at each different stimulation pulse. This can be particularly important when different amplitudes or pulse widths are used for pulses of different frequencies. The Time Series VOA may allow the user to cycle through the waveform and select different time points along the waveform. For each point, the VOA may be calculated based on the amplitude or total amount of charge delivered at that time. This can be shown in a variety of different ways, including a series that can be clipped or played where the VOAs are updated based on the timed pattern with respect to a timeline that a user can click or based on clicking or dragging across positions on the displayed pattern or waveform to show the VOA at any point within the pattern, etc. In an example, the VOAs can be played back as a movie. Alternatively, the user can select discrete points for display of the corresponding VOA. For example, selectable icons or other graphical components associated with the VOAs may be displayed, in response to whose selection, the system may display the corresponding VOA. Further, the components may be displayed according to the sequence in which the parameters corresponding to the VOAs are applied for the therapy. For example, they may be displayed along a timeline.

Another possible way to display this would be as a single volume which is the main volume of tissue stimulated. If this does not encompass a sufficient amount of information, it would also be possible to display the VOA as a gradient or with fuzzy boundaries.

When displaying VOAs for interleaved pulse widths, VOAs caused by different frequency parameter sets may be displayed in different colors so that the user can differentiate which areas are being affected by which parameters and be better able to change any regions which are unsatisfactory.

Programming Interface

Referring again to FIG. 3e, in an example embodiment of the present invention, a system may be configured to display a user-interactive interface including, e.g., three vertical sections. As shown in FIG. 3e, the far left section includes a program selection area 3000 having at least one program 3001 (an electrode leadwire parameter set, e.g., including a combination of amplitude, rate, pulse width, and electrode combination) to be selected, activated, and/or simulated. The middle section includes a directional programming area 3002 illustrating an example model of an implantable leadwire having one or more electrode contacts that can be selected, activated, or otherwise changed. In the example shown in FIG. 3e, the leadwire model includes eight electrodes 3008. The far right section includes a modeling area 3004 having an example of a 3-D model including an implantable leadwire and an estimated VOA 3005.

In an example embodiment, a unique mark may displayed in the leadwire models of areas 3002 and 304 to visually indicate how a model 2-D leadwire model in area 3002 rotationally corresponds to the model leadwire in area 3004. For example, the a mark, e.g., a square may be displayed at the top-right electrode shown in area 3002. The mark may also be shown at a location of the model leadwire shown in area 3004 that corresponds to the top-right electrode shown in area 3002.

In an example embodiment, in the program selection area 3000, for each selectable program 3001, there may be displayed a battery status area 3006, including the current available battery percentage of an IPG configured to deliver an electrical stimulation pulse, as well as an estimated remaining battery life of the IPG should the selectable program be activated.

In this example, the program selection area 3000 includes four selectable program spaces, three of which have been programmed. Program 1 is shown to be active. Programs 2 and 3 are programmed but not active. Program 4 has not been programmed and is not active. In an example, while Program 1 is active, Programs 2-4 can be programmed, reprogrammed, or otherwise altered or changed in a preview mode. During each program change, the program selection area 3000 can update the battery status or estimated remaining battery life for the selected or previewed program 3001.

In certain examples, Program 1 can be altered while it is active, with or without immediately changing the programming instructions to the device. In an example, Program 1 will continue unaltered, despite the changes to Program 1 in the programming window, until a STOP button or other selection to activate changes is selected. In alternative example embodiments, the changes to an active program can be delivered to the IPG as they are changed.

In an example embodiment, the middle directional programming area 3002 can be used to alter or change the settings of one or more electrodes on a leadwire for the program 3001 selected in the program selection area 3000. In an example, one or more electrodes can be selected to be a cathode or an anode, or multiple electrodes can be selected to be a combination of one or more cathodes or anodes. In the example of FIG. 3e, three of eight electrodes are selected as anodes in a monopolar configuration.

In an example embodiment, the interface is configured such that the current for the leadwire can be selected, such that the amplitudes of the respective electrodes are modified to obtain the selected current. The interface may be further configured such that after the current for the leadwire is selected, amplitudes of individual electrodes may be selected, in which case the system may update the value of the leadwire current accordingly. In the example of FIG. 3e, the current for the leadwire can be selected using a current selection button 3007 (shown as one of the toolbar buttons immediately below the illustrated selectable tabs).

In an example embodiment, the status of each electrode or current to be delivered to each electrode can be individually selectable. For example, selecting an electrode 3008 can change the electrode 3008 from off to active as an anode (e.g., in the bipolar arrangement), from active as an anode, to active as a cathode, from active as a cathode to off, etc., the order being exemplary. In an example, once active, either positive or negative, a stimulation current amplitude can be selected. In certain examples, the current to be delivered (e.g., negative for an anode, positive for a cathode) for an active electrode can be displayed alongside the electrode as shown in FIG. 3e, or can be altered or changed from its current value (e.g., using arrows 3010 or other means, such as being directly input).

In FIG. 3e, three electrodes 3008 are shown to be active. For each of the three electrodes 3008, its respective current is displayed adjacent the electrode 3008 sandwiched between up and down arrow buttons 3010 selectable for, respectively, increasing and decreasing the electrode's current. It is noted that the particular values in FIG. 3e may be imprecise. For example, as indicated above, the individual amplitudes of the electrodes 3008 may add up to the overall current value shown in the current selection button 3007.

In an example, the direction of the current field can be altered, such as by using arrows to direct adjacent or other electrodes (previously active or off) to assume at least a portion of the current of their neighboring electrode. For example, two directional input buttons displayed above and below the model leadwire may be used to shift the current field(s) upwards or downwards. In the example of FIG. 3e, four directional input buttons 3012-3015 are shown for shifting the current field(s) upwards, downwards, to the left, and/or to the right. If the location of the current is desired to be lower, the down arrow button 3015 at the bottom of the directional programming area 3002 can be selected, and at least one of the contact configuration and stimulation amplitude may be altered in such a way as to increase activation of tissue in the selected direction and decrease activation of tissue in the opposite direction. For example, with respect to FIG. 3e, both of the current fields 3020 may shift downwards in response to the selection of the button 3015. In other examples, if the down button 3015 is selected, all of the current from the previous configuration can be transferred entirely to adjacent electrodes 3008 in the selected direction. In other examples, the field can be stretched, expanded, or shrunk in a similar fashion. For example, additional or alternative, e.g., directional, controls may be provided for the stretching or shrinking in a particular direction.

In an example embodiment, if a program is active, each button or editable field can be a first color to reinforce that the changes being made are to an active stimulation program, such that they can be implemented as they are changed, or can be implemented after making the changes, calculating or simulating a predicted area of activation or stimulation field, and accepting the one or more changes. If a program is inactive, each button or editable field can be a second color to reinforce that the changes being made are to an inactive stimulation program.

In other examples, the directional programming area can include a 3-D rendering of a leadwire having one or more electrode contacts. Further, one or more other stimulation parameters, such as a pulse width, a frequency, etc., can be set, established, changed, or altered.

In an example embodiment, the modeling area, as further described above, can include at least one of a 3-D model and one or more medical images of a patient's anatomy, an overlaid leadwire model, and a VOA, e.g., corresponding to the parameters input in the directional programming area. As one or more of the stimulation parameters or electrode configurations of the selected program changes, the modeling area can graphically illustrate the estimated effects of such parameters or configurations.

In the example of FIG. 3e, a 3-D model illustrates an implanted leadwire in the sub thalamic nucleus (STN) of a patient. In an example, a VOA (illustrated in FIG. 3e as the circle shown around a portion of the leadwire) can be calculated for a given set of programming parameters (e.g., Program 1, Program 2, Program 3, etc.).

In an example embodiment of the present invention, the current fields and/or the VOAs may be shifted by a drag-and-drop function, e.g., performed via a mouse, stylus, touchscreen, or any other suitably appropriate device.

3-D Current Steering Using a Directional DBS Lead

Figure 17:
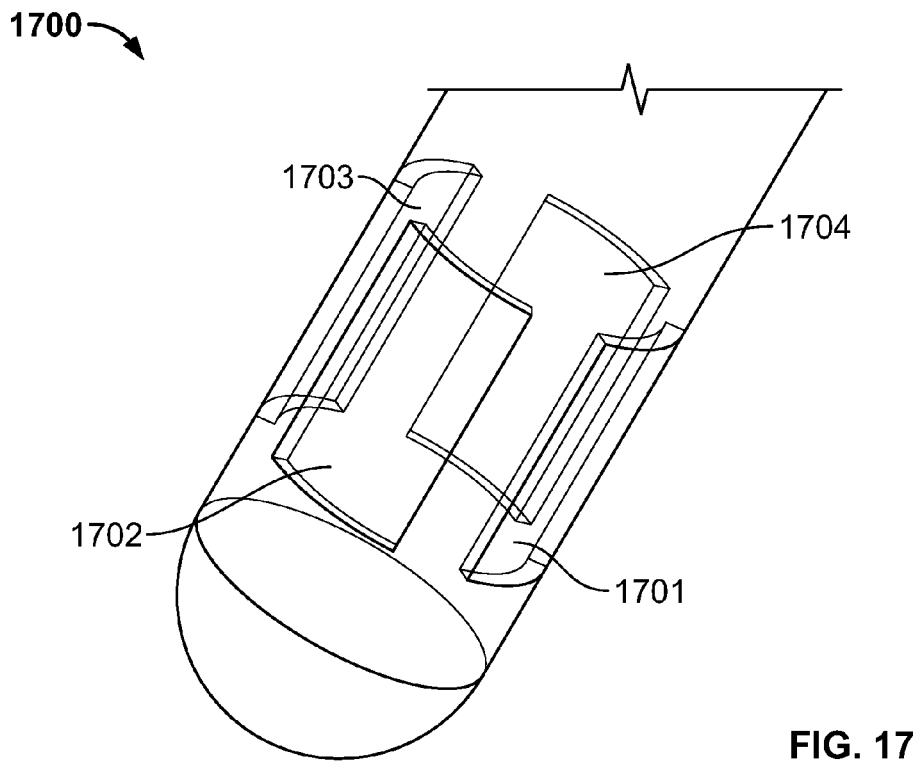
FIG. 17 is a diagram that illustrates a leadwire with electrode contacts located rotationally about the leadwire, according to an example embodiment of the present invention.
Figure 23:
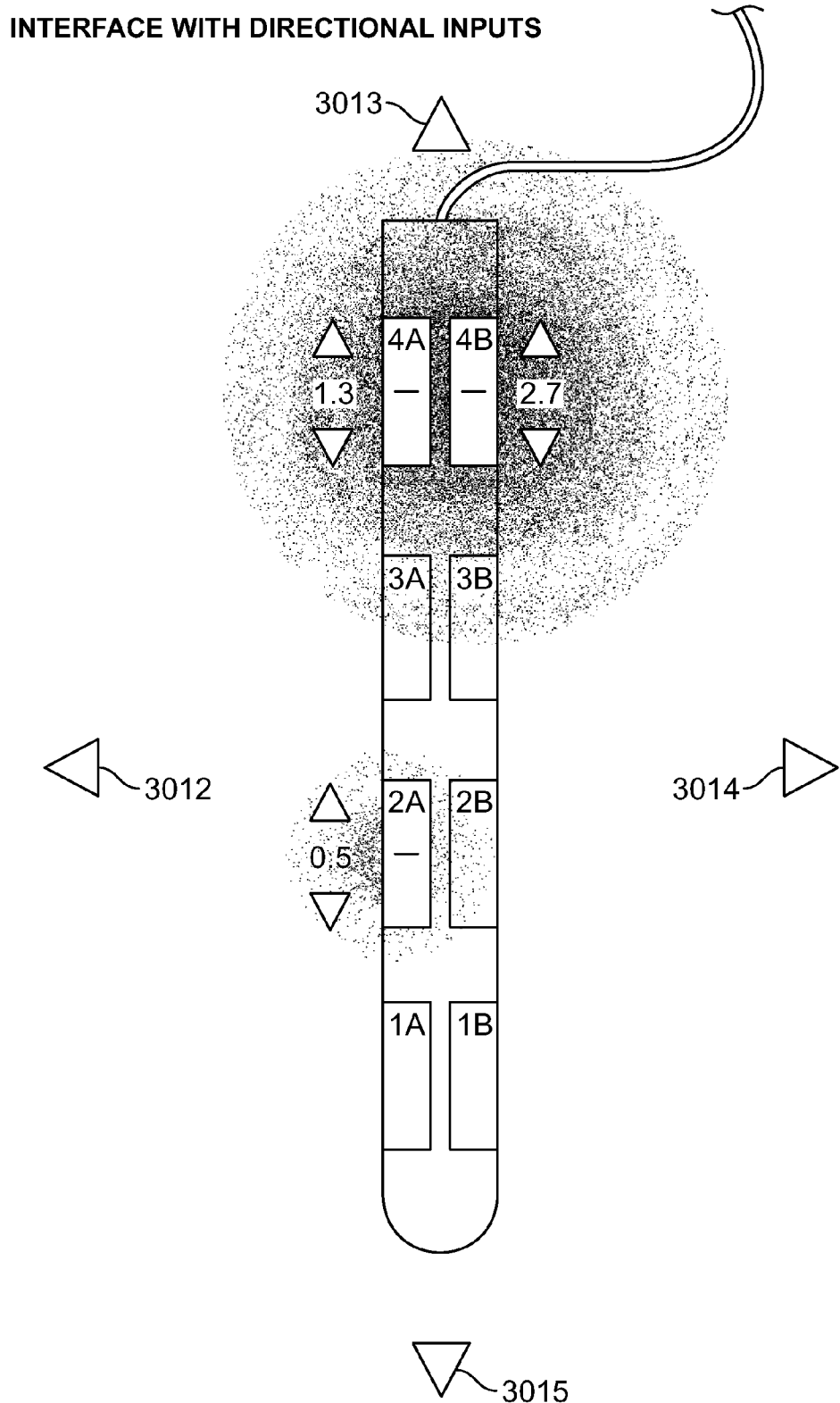
FIG. 23 illustrates an interface via which to control and view a stimulation field about electrodes, according to an example embodiment of the present invention.

In an example embodiment of the present invention, a directional stimulation leadwire has four electrode contacts located rotationally around the leadwire. FIG. 17 shows a leadwire and electrodes 1701-1704. The leadwire is attached to a generator that allows for independent current sources on each electrode contact individually. In the example embodiment, there are several ways the field can be manipulated. Looking in two dimensions, the field can be moved either up or down the leadwire in the Z direction by hitting directional up or down arrow buttons 3013 and 3015 as shown in FIG. 23, respectively, above and below the model leadwire. The field can be moved side to side in the X direction by hitting directional side to side buttons 3012 and 3014 as shown in FIG. 23. The field can also be moved rotationally around the leadwire by hitting a clockwise or counterclockwise directional button (not shown) and/or manipulating a rotational knob or wheel, and/or a joystick. In each case, there is an algorithm that controls the movement of the stimulation field by changing the amount of current delivered to a set of electrodes to either a different amount of current to some or each electrode or a different combination of electrodes. The view as shown in FIG. 23 can be rotated either gradually or by 90 degree (or some other number of degrees) increments in order to see all angles of the stimulation field, e.g., in the directional programming area 3002 and the modeling area 3004 as shown in FIG. 3e. Additionally, the view can be shown in conjunction with an overall orthogonal view or a cross-sectional view having a particular cross-section in the orthogonal direction, so all three dimensions can be seen simultaneously by looking at multiple 2-D views. Where a cross-sectional view is shown, in an example embodiment, the system may include a control, e.g., the selectable slice bar 3031, for selecting a particular cross-section.

Figure 18:
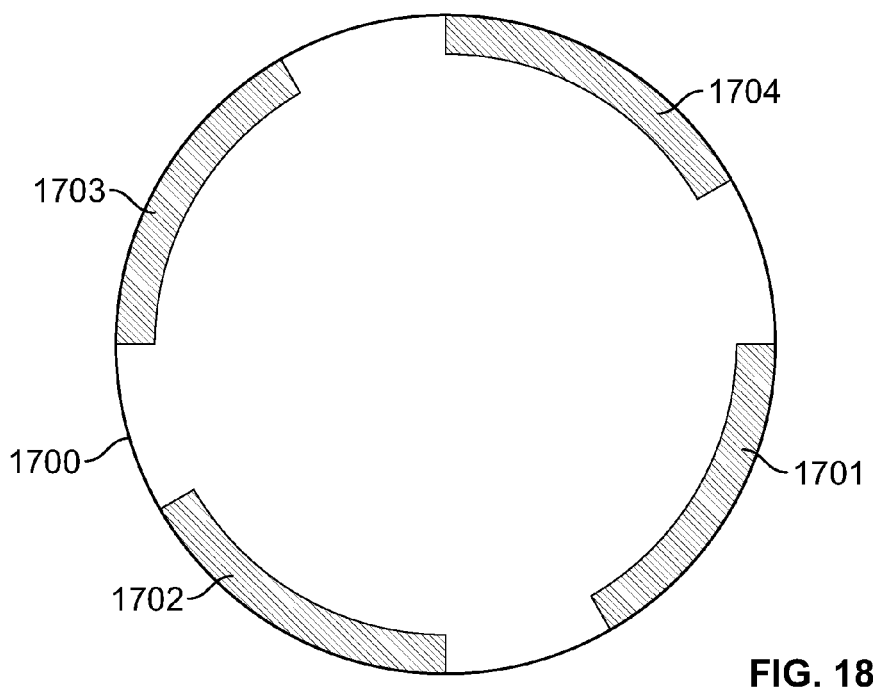
FIG. 18 is a diagram that illustrates a cross sectional view of the leadwire shown in FIG. 17, according to an example embodiment of the present invention.
Figure 19:
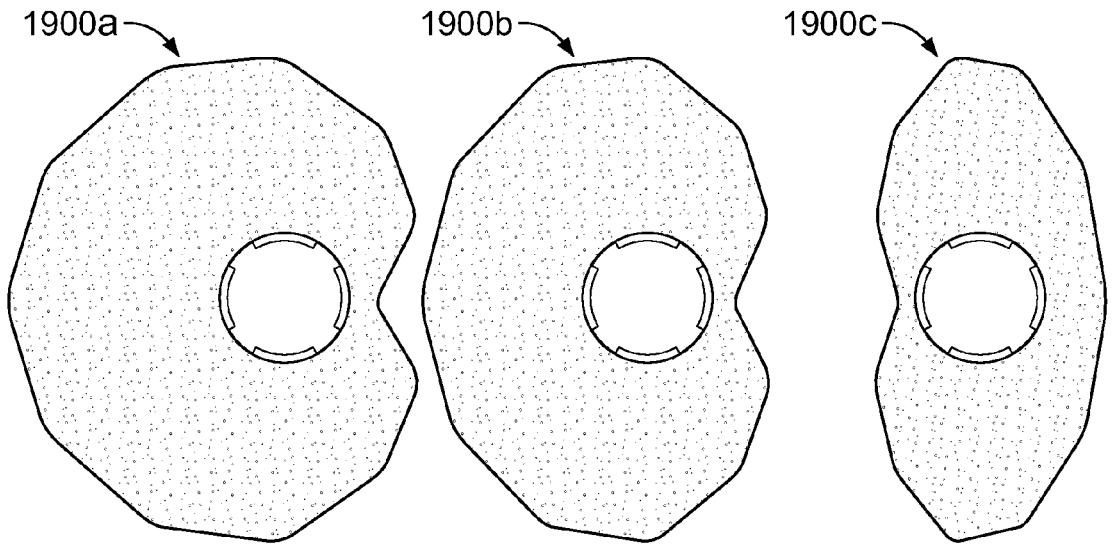
FIG. 19 shows a gradual and smooth adjustment of the field along the X axis, according to an example embodiment of the present invention.

With respect to the cross sectional view of the stimulation leadwire, as shown in FIG. 18, and the stimulation field, there are several ways of steering the stimulation field with a directional input. As shown in FIG. 19, an example embodiment of the present invention allows for a gradual and smooth adjustment of the current field from position 1900a to position 1900b, and then to position 1900c along the X axis. (This can be similarly done along the Y axis.)

Figure 20:
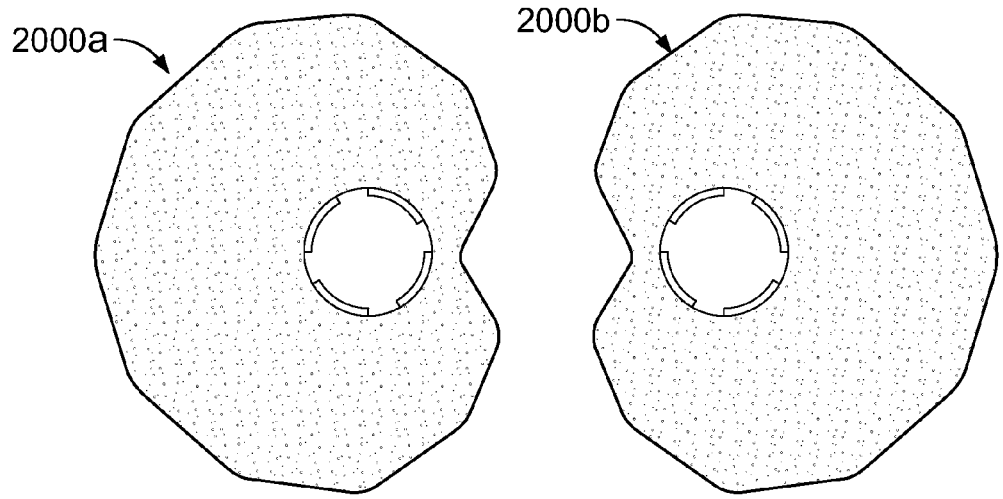
FIG. 20 shows an adjustment along the X axis by transposing the field about the Y axis, according to an example embodiment of the present invention.

As shown in FIG. 20, an example embodiment of the present invention allows for a quick adjustment along the X axis by transposing the current field about the Y axis from position 2000a to position 2000b. (In an example embodiment, this can be similarly done along the Y axis by transposing about the X axis.)

Figure 21:
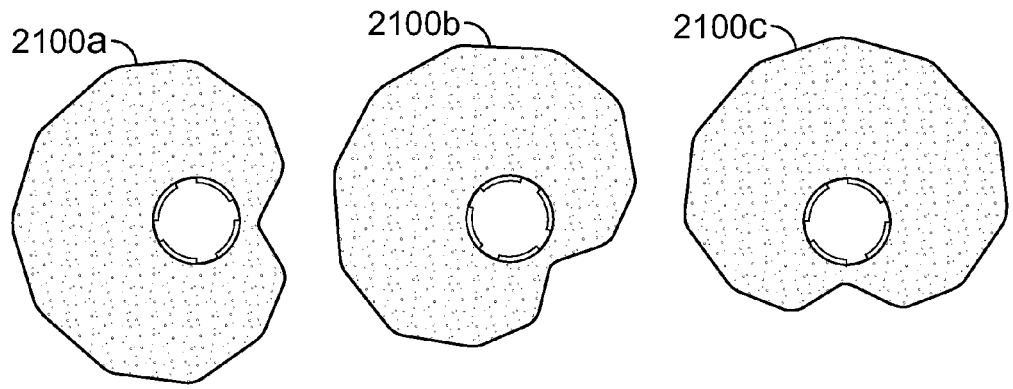
FIG. 21 shows a rotational adjustment of the field allowing for movement of the stimulation field in both the X and Y axes, according to an example embodiment of the present invention.

Similarly, as shown in FIG. 21, rotational input allows for movement of the current field rotationally about the Z axis from position 2100a to position 2100b, and then to position 2100c.

Figure 22:
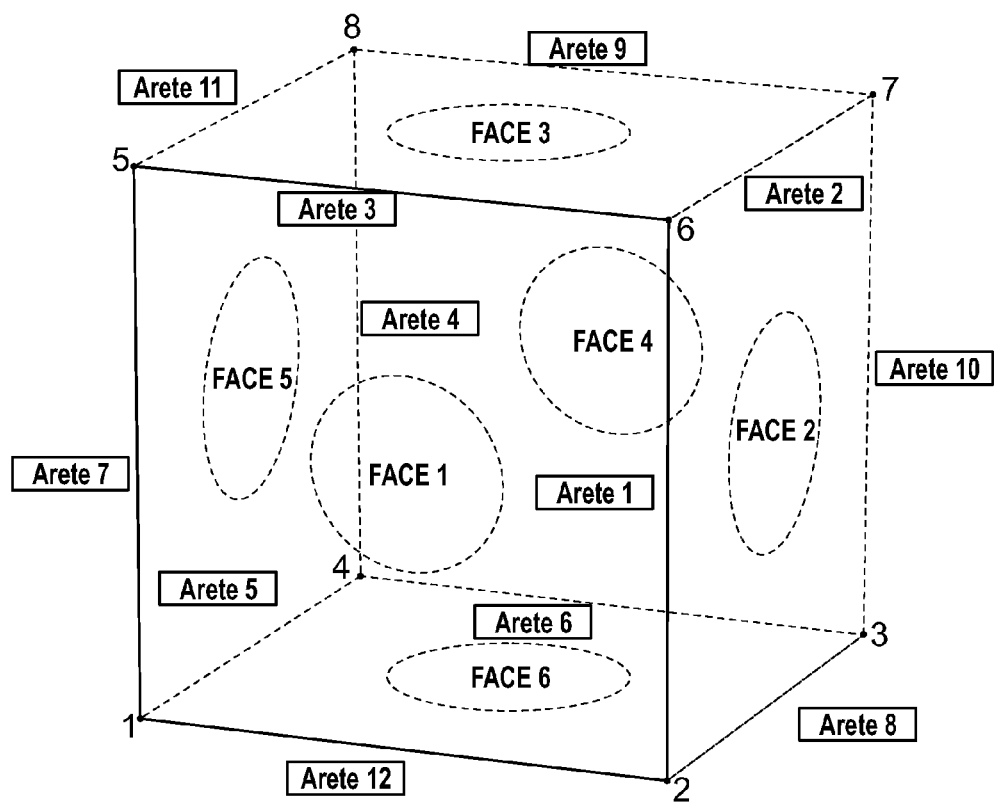
FIG. 22 shows 26 linear directional inputs for steering a field, according to an example embodiment of the present invention.

An example embodiment of the present invention provides for 26 basic linear directional inputs that can be used to steer a current field for a leadwire, as shown in FIG. 22. For example, the stimulation leadwire is in the center of the cube shown in FIG. 22. Each set of directional inputs can be displayed separately or in combination with another set. The first set of inputs is directed toward the vertices (8), another set of inputs is directed perpendicular to each face (6), and additionally another set of inputs is directed toward the midpoint of each side or arête (12). In addition, two rotational directional inputs can be used (clockwise and counterclockwise) for rotational movement as shown in FIG. 21.

While the above examples have been discussed in connection with an arrangement including four electrodes located rotationally around the leadwire, other embodiments may include an arrangement having other configurations such as, for example, three or five electrodes located around the leadwire.

Some electrode arrangements may include a split of the electrodes with four electrodes extending less than 360° about the circumference of the leadwire as shown in FIGS. 17 and 23. Others may instead include, e.g., one cylindrical electrode surrounding the leadwire. In an example embodiment of the present invention, a system and method includes an operation for controlling the multiple electrodes as shown in FIGS. 17 and 23 as though they were a single cylindrical electrode. When using this operation, the parameters for adjusting the electrodes may be uniformly applied to a group of electrodes surrounding the lead at the same coordinate in the Z direction.

In addition to a directional input for redistributing current from one set of electrodes to another, other methods can be used such as:
  rotating the 3-D view of the leadwire and brain structure so the intended direction of stimulation is to the left or right of the leadwire and manually select the location to which to move the current field;
  touching/selecting the structure or the structure name towards which the current field is desired to be directed, and then, e.g., the system automatically, increasing or decreasing the overall amplitude or intensity (this may include increasing the amplitude on more than one electrode simultaneously) in order to fill the intended stimulation target; and/or
  displaying a grid of nodes throughout the 3-D field that can be selected in order to steer the current field toward one of the nodes in 3 dimensions.

In an example embodiment of the present invention, the system may provide for receipt of user input for steering a displayed VOA, e.g., as displayed in the modeling area 3004, and responsively select the electrode parameters which result in the shifted VOA. The system may also responsively move the current field(s).

Thus, the steps detailed below represent one possible method for programming a leadwire in 3-D according to an example embodiment of the present invention (the sequence of some of the steps may be changed and various steps, e.g., the display of side effect volumes, may be omitted):
  1. acquire imaging data (MRI, CT, other);
  2. fuse imaging data (MRI and CT, other);
  3. register a 3-D atlas to patient data;
  4. display:
    a. a 3-D view of the atlas;
    b. a 3-D target VOA;
    c. 3-D side effect volumes;
    d. a 3-D view of the leadwire;
    e. a cross sectional view of the leadwire; and
    f. an initial model stimulation field;
  5. receive input, e.g., via selection of one or more of six linear directional inputs (left, right, up, down, and the two directions extending into and out of the screen and orthogonal to the other four directions) and/or one of two rotational inputs (clockwise, counterclockwise), for moving the displayed stimulation field until the stimulation field is located approximately at the target stimulation field; and
  6. increase/decrease the intensity in order to best fit the fill of the target stimulation volume.

Another method, according to an example embodiment of the present invention, is to:
  1. acquire imaging data (MRI, CT, other);
  2. fuse imaging data (MRI and CT, other);
  3. register a 3-D atlas to patient data;
  4. display:
    a. a 3-D view of the atlas;
    b. a 3-D target VOA;
    c. 3-D side effect volumes;
    d. a 3-D view of the leadwire;
    e. a cross sectional view of the leadwire; and
    f. an initial model stimulation field;
  5. automatically calculate the settings that create a best fit of the stimulation field to the target stimulation field;
  6. receive input, e.g., via selection of one or more of six linear directional inputs (left, right, up, down, into or out of the screen) and/or one of two rotational inputs (clockwise, counterclockwise), for making manual adjustments to move the stimulation field until the stimulation field is located approximately at the target stimulation field; and
  7. increase/decrease the intensity in order to best fit the fill of the target stimulation volume.

Method of Implanting a DBS Leadwire

A method of implanting a DBS leadwire has been described for example with respect to FIGS. 5 and 6. Additionally various methods of estimating VOAs, selecting optimal stimulation parameters, and modifying parameters affecting location and size of VOAs have been described. In an example embodiment of the present invention, these various methods may be used to perform a method of implanting a DBS leadwire. A method of implanting a DBS leadwire according to an example embodiment of the present invention is to (the sequence of some of the steps may be changed and various steps, e.g., the display of side effect volumes step 5(c) and/or the stimulation to verify position step 17, may be omitted):
  1. acquire imaging data (MRI, CT, DTI, other) (various forms of data can be acquired such as MRI with a headframe or CT with a headframe and MRI without a headframe);
  2. fuse imaging data (MRI and CT, other) including MRI data with surgical headframe;

3. display a 2-D and/or 3-D atlas;
4. automatically and/or manually stretch, translate, rotate, deform, and fit the atlas to the patient's brain structures;
5. display at least one of:
   a. a 3-D view of the atlas;
   b. a 3-D target stimulation field (e.g., based on a database of previous patients programming); and
   c. 3-D side effect volumes (e.g., based on a database from previous patients programming);
6. determine a surgical plan for placing the DBS leadwire, including determination of:
   a. location of burr hole;
   b. angle of entry; and
   c. track of leadwire from burr hole to target;
7. display one or more leadwires in 3-D in the 3-D view of the atlas;
8. simulate possible VOAs in the target stimulation volume for each of the one or more leadwires, including to:
   a. manually adjust the leadwire location (angle, depth, etc.) and stimulation settings to get best coverage of the target stimulation volume; and/or
   b. autofit to best VOA and leadwire location;
9. automatically and/or manually analyze leadwire locations and VOA's of step 8, and determine and select best leadwire, location, and stimulation settings;
10. create burr holes;
11. perform MER recordings;
12. enter MER data into software or automatically acquire the data (if data is auto acquired the brain structures would be auto identified as well);
13. adjust the atlas to fit MER recording data:
    a. manually;
    b. automatically;
    c. using linear scaling; and/or
    d. using non linear statistical methods;
14. recalculate or adjust and display the target stimulation volume according to the adjusted atlas;
15. recalculate which leadwire is to be implanted, the optimal location, and optimal stimulation settings as described in steps 8 and 9;
16. insert the leadwire; and
17. stimulate to verify positioning.

Method of Programming a DBS Leadwire

As described above, method according to example embodiments of the present invention may provide for estimation of VOAs for certain parameter settings. Similarly, parameter settings may be estimated for a selected VOA. Moreover, for a target activation region, the system may estimate the possible VOAs close to the target activation region for various possible parameter settings. The target activation region may be one selected with respect to a model of the patient anatomy, e.g., without regard to the particular placement of the leadwire. The system and method of the present invention may, based on the leadwire location and configuration, determine estimated parameter settings for an estimated VOA closely corresponding to the target region. A clinician may subsequently test the system-suggested parameters or similar parameters, and adjust the parameters using some of the methods described above, since the resulting benefits and side effects may be different than those anticipated by the system. For example, the actual VOA may be different than the estimated VOA.

Accordingly, a method of programming a DBS leadwire, e.g., subsequent to implantation of the leadwire in a patient's brain, according to an example embodiment of the present invention is to (the sequence of some of the steps may be changed and various steps, e.g., step 2(e), may be omitted):

1. obtain, e.g., by receipt of user-input or by importation of a file, folder, or other data structure from a surgical planning system, surgical planning data including but not limited to:
   a. imaging data;
   b. atlas location;
   c. a surgical plan;
   d. MER data;
   e. leadwire location and type; and
   f. initial stimulation parameters, e.g., those determined via the system estimations for a target stimulation volume;
2. display the following:
   a. a 3-D atlas;
   b. a 3-D leadwire;
   c. the target stimulation volume;
   d. the initial stimulation parameters; and
   e. the estimated VOA(s) for the initial stimulation parameters;
3. test initial stimulation parameters;
4. obtain additional possible stimulation parameter sets, the determination including one of:
   a. monopolar review (a wizard is included in the software for stepping through a parameter setting for each electrode separately);
   b. propose stimulation settings based on an algorithm to minimize the number of settings to get to the best therapeutic outcome;
   c. other regimented sequence of initial programming parameters; and
   d. combination of 'a' and 'b' where 'a' is performed and then 'b' to further narrow the field;
5. test the various proposed stimulation settings obtained in step 4;
6. during each test of a stimulation setting, receive input regarding, and record, the following:
   a. benefits of the stimulation—each benefit individually and quantitatively; and
   b. negative effects of the stimulation—each side effect individually and quantitatively;
7. the system calculates and displays the following based on the tested parameters and the received input regarding the test results:
   a. volume of tissue that has been explored, e.g., using the flashlight feature:
      i. 2-D for each MRI slice; and/or
      ii. 3-D;
   b. for each benefit, a target stimulation volume by finding an overlap in volumes where benefits were observed and a subtraction of volumes where benefits were not observed:
      i. 2-D for each MRI slice; and/or
      ii. 3-D;
   c. for each side effect, a side effect volume by finding an overlap in volumes where side effects were observed and a subtraction of volumes where side effects were not observed:
      i. 2-D for each MRI slice; and/or
      ii. 3-D;
8. based on the noted benefits and side effects relative to the various tested VOAs, the system determines and displays:
   a. a new target stimulation volume for each benefit individually;

b. a collective target stimulation volume that incorporates an addition of all the volumes of step 8(a);
c. side effect volumes for each individual side effect; and/or
d. a collective side effect volume that incorporates the addition of all side effects volumes of step 8(c);
9. the system estimates and outputs:
a. stimulation settings that result in a VOA that fills the intended benefit volumes without filling the side effect volumes for a specific benefit; and
b. stimulation settings that result in a VOA that fills the intended benefit volumes without filling the side effect volumes for a collective therapy where:
i. for example in Parkinson's, a particular benefit such as tremor may be weighted differently than rigidity, the goal of the stimulation settings being to optimize the total benefit to the patient;
ii. benefit profile can be user defined based on the patient's needs; and
iii. a benefit index is developed based on initial user inputs and patient desires;
10. after the target stimulation volumes and the side effect volumes are calculated the user can input, via a user interface, instruction that:
a. have the positioning of the atlas automatically updated based on the volumes; or
b. manually move the atlas to position the atlas to better correlate to the volumes;
11. for each set of parameter settings tested subsequent to the initial performance of step 8, update the explored volumes of tissue and the targeted stimulation volume;
12. optionally save different benefit profiles either on the IPG or in the patient or clinician programmer system, where profiles may include:
a. a tremor control profile indicating, for a tremor control therapy, a targeted stimulation volume, suggested parameters, and/or corresponding estimated VOA for best filling the targeted stimulation volume;
b. a rigidity control profile indicating, for a rigidity control therapy, a targeted stimulation volume, suggested parameters, and/or corresponding estimated VOA for best filling the targeted stimulation volume; and/or
c. a patient total benefit index profile indicating, for total patient benefit, a targeted stimulation volume, suggested parameters, and/or corresponding estimated VOA for best filling the targeted stimulation volume; and
13. at the end of a programming session, sync, by the physician, the software, to a database that will automatically update the data set for determining the initial target stimulation volume for a particular therapy and the side effect volumes.

For example, with respect to steps 4 and 5, the monopolar review may include initially setting the electrode current values to zero, and stepping up the value of one electrode incrementally. For example, the value for the subject electrode may be increased, while the values of the other electrodes remain the same. This may be separately repeated for each electrode. For each step, the setting may be tested to determine whether it causes a side effect. In this way, the clinician can get a good idea of the upper limits of, for example, the amplitude values to be applied to the various electrodes.

With respect to step 4(b), instead of stepping incrementally through the various values for each electrode, one set increment at a time, the system may incorporate user input indicating results of a previous setting to skip through certain settings. For example, if a certain type of a severe side effect is indicated by the clinician to have occurred when the value of electrode 1 was at value four, the system may determine that a similar side effect is likely to occur at values five to eight, and may therefore skip to value nine. Alternatively or in addition, the system may begin at or near the initial estimated stimulation parameters and continue with the monopolar review from those initial settings.

With respect to step 9, estimation equations, e.g., as described above with respect to the monopolar and bipolar configurations, may be used.

With respect to step 10, where a target stimulation volume determined at step 8 differs from an initial target stimulation volume, which may be based on data concerning multiple patients, it may be determined that the patient atlas obtained at step 1 is likely to be incorrect. At step 10, the atlas may be adjusted in view of such discrepancies. For example, if the new target stimulation volume is slightly shifted to the right from the initial target stimulation volume, anatomical structures of the atlas may be shifted so that the new target stimulation volume is shifted to the left.

Patient Monitoring and Interaction

In an example embodiment of the present invention, the system is configured to store or log information (e.g., received information, sensor information, stimulation parameter information, such as stimulation duration, cycling parameters, etc.). In certain examples, the system is configured to receive, store, and/or display user or patient information (e.g., comments) regarding the user or patient's observation of the efficacy of therapy, therapy benefits, noticed side effects, etc.

In an example embodiment of the present invention, the system is configured to include data input or data analysis capabilities. In an example, the system includes one or more sensors used for the data input or analysis capabilities. In an example embodiment, the system is configured to receive information from at least one sensor or other instrument coupled to the clinician programmer system (e.g., anesthesia or other monitoring equipment). For example, the clinician programmer system can intra-operatively receive data input from an anesthesia cart.

In an example embodiment, the clinician programmer system (or another component communicatively coupled to the clinician programmer system) includes a camera, video camera, audio recorder, and/or other sensor configured to take or receive a still, moving, and/or other image, video, and/or audio of the patient, the patient's surroundings, etc.

In an example embodiment, the one or more sensors of the clinician programmer system or of another system or device coupled thereto include an accelerometer, a force transducer, a temperature sensor, and/or other sensor configured to sense physiological or other information from a patient or the patient's environment or otherwise receive input on a patient's recovery. In an example, the accelerometer, force transducer, or other sensor can be used as part of a rehabilitation routine.

In example embodiments, the physiological sensors of or coupled to the clinician programmer system may include, e.g., a brain activity sensor (e.g., one or more electrodes configured to detect brain activity, etc.), an EEG sensor, a cardiac sensor (e.g., one or more sensors configured to detect a depolarization, or other information, of the heart, etc.), a pressure sensor (e.g., a blood pressure, etc.), a respiration sensor (e.g., a tidal volume sensor, etc.), an impedance sensor (thoracic impedance, etc.), an activity sensor (e.g., an accelerometer or other activity, posture, sleep, or other sensor configured to receive information about the level or state of activity of the patient), and/or other physiological sensor configured to sense or receive physiological or other information from the patient.

In an example embodiment, the clinician programmer system is configured to receive information from the sensor(s), and analyze or store the information, for example, to establish a medical history of the patient (e.g., establish a log for a specific patient for a clinician or other user to review), for later analysis by a clinician or other user (e.g., to monitor stimulation efficacy, etc.), to suggest or alter a stimulation setting or parameter, or for other uses.

The data from the sensors can be stored on the clinician programmer system and tracked over time to see how the patient is doing with their stimulation in conjunction with rehabilitation. In certain examples, the camera, video camera, audio recorder, or other sensor configured to take or receive the still, moving, and/or other image, video, and/or audio of the patient can be configured to actively or passively monitor the patient (e.g., patient progress, condition, etc.), receive information from the patient (e.g., information from a query), or otherwise monitor or record information from the patient for immediate or later medical or other uses.

For example, in an embodiment in which the system includes a camera (e.g., video and/or still), the camera can be used to document patient progress, or to observe patient performance as they respond to instructions or to different stimulation parameters or settings. In certain examples, the images and/or video can be stored, e.g., for later review or use, such as to judge the effectiveness of certain stimulation settings. In other examples, the images and/or video can be time stamped and can be compared to other physiological information (e.g., EEG, etc.).

In an example embodiment, the one or more sensors can be used to evaluate the efficacy of certain programming parameters, such as by receiving information in response to certain (e.g., predefined, known, etc.) patient tasks in order to evaluate patient status (e.g., to monitor overall patient status or improvement, to monitor patient status or improvement since the patient's last office visit, etc.). For example, sensors may be used to obtain physiological data while the patient performs the task and the obtained data may be compared to values expected for the performance of the task. For example, the task may be to pull on a strain gauge in order to measure the patient's strength. In another example, a temperature may be used to sense the patient's temperature while performing a certain task. In another example, motion sensors may be used to record information, e.g., speed, force, and/or duration, regarding the patient's motion when performing a certain task, e.g., lifting a certain object over the patient's head.

In an example embodiment of the present invention, the system includes a query module configured to provide a query to a user or patient and receive an answer to the query. In various examples, the query module may be configured to deliver a video, text, audible, and/or graphical query to the user or patient. In certain examples, the query can include information regarding generally physiological or personal information, a therapy efficacy, a noticed side effect, etc. In an example embodiment, the system is configured to receive and record the answer to the query, e.g., for later review or use, such as to judge the effectiveness of a therapy and/or of certain stimulation settings, to suggest further programming changes, etc.

The query may be for, for example, a Barthel index activity query for which answers include a numeric metric indicating degree. For example, a query may be regarding feeding of the patient, where 0=unable, 5=needs help, and 10=independent. Other metrics may be used for other example queries.

The query can be given by a clinician in direct (office visit) or indirect (through email, phone, or other communication) contact with the patient, or the query can be given by the clinician programmer system or other device in contact with the patient (e.g., a patient programmer system coupled to the clinician programmer system).

In an example embodiment of the present invention, the system is configured to store any received information, such as received sensor, video, query, or other received information. The system may be configured to organize the received information and/or display the information (e.g., in an easy-to-interpret graphical fashion). In certain examples, the system is configured to store some or all of the information, received or derived, locally on the clinician programmer system, or some outside device can store some or all of the information.

In an example embodiment of the present invention, a system includes a clinician programmer system and/or terminal as well as a patient programmer system and/or terminal. In an example, the patient programmer system is configured to receive information from the IPG or other sensor and communicate the information to the clinician programmer system. In other examples, the clinician programmer system is configured to communicate queries, programmer settings, and/or other information to the patient programmer system for display at the patient programmer system to the user, and/or upload to the IPG or other sensor. For example, the system is configured to receive stimulation parameters for new wave shapes and patterns. Once entered, the system is configured to provide for the new wave shape or pattern to be uploaded to the IPG or other therapy delivery module for delivery to the patient. In an example, the patient programmer system is configured to allow a patient to change, alter, or otherwise adjust one or more therapy parameters, such as an on/off state, or other acceptable stimulation parameters, e.g., within safe operating guidelines.

In an example embodiment of the present invention, the clinician programmer system is configured to automatically adjust one or more therapy parameters, e.g., based upon patient status or physiological conditions, etc.

Figure 8:
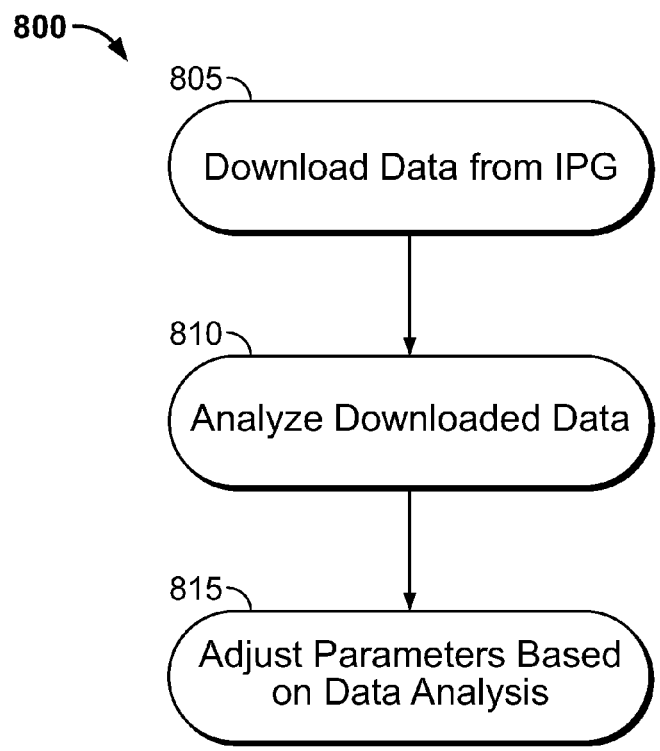
FIG. 8 illustrates generally an example of an example of adjusting parameters based on data analysis.

FIG. 8 illustrates generally an example of a method 800 including downloading data from the IPG, analyzing downloaded data, and adjusting parameters based on data analysis.

At step 805, data from the IPG is downloaded. In an example, the data from the IPG includes physiological data of the patient, therapy parameters, or IPG status information (e.g., battery status, lead impedance, etc.).

At step 810, the downloaded data is analyzed.

At step 815, parameters are adjusted based on data analysis. In this regard, it is noted that VOA, benefit, and side effect estimations may be used to initially select parameters, but the parameters may be subsequently adjusted in view of results of actual stimulations. In an example, the duty cycle, and consequently, other therapy parameters, can be adjusted to save power, yet yield optimal therapy given the power constraints. In other examples, other parameters, such as electrode configuration, etc., can be manually or automatically adjusted depending on received information (e.g., lead impedance, etc.).

Patient History Functions

In an example embodiment of the present invention, the system is configured to sense, and/or otherwise receive, store, and/or track over time, one or more physiological measurements, parameters, and/or other information of a patient. In an example embodiment, the system may include a patient history application for such functions. For example, information from each patient inquiry, checkup, visit with a physician or other caregiver, etc., can be stored and saved using the system of the present invention.

Figure 11:
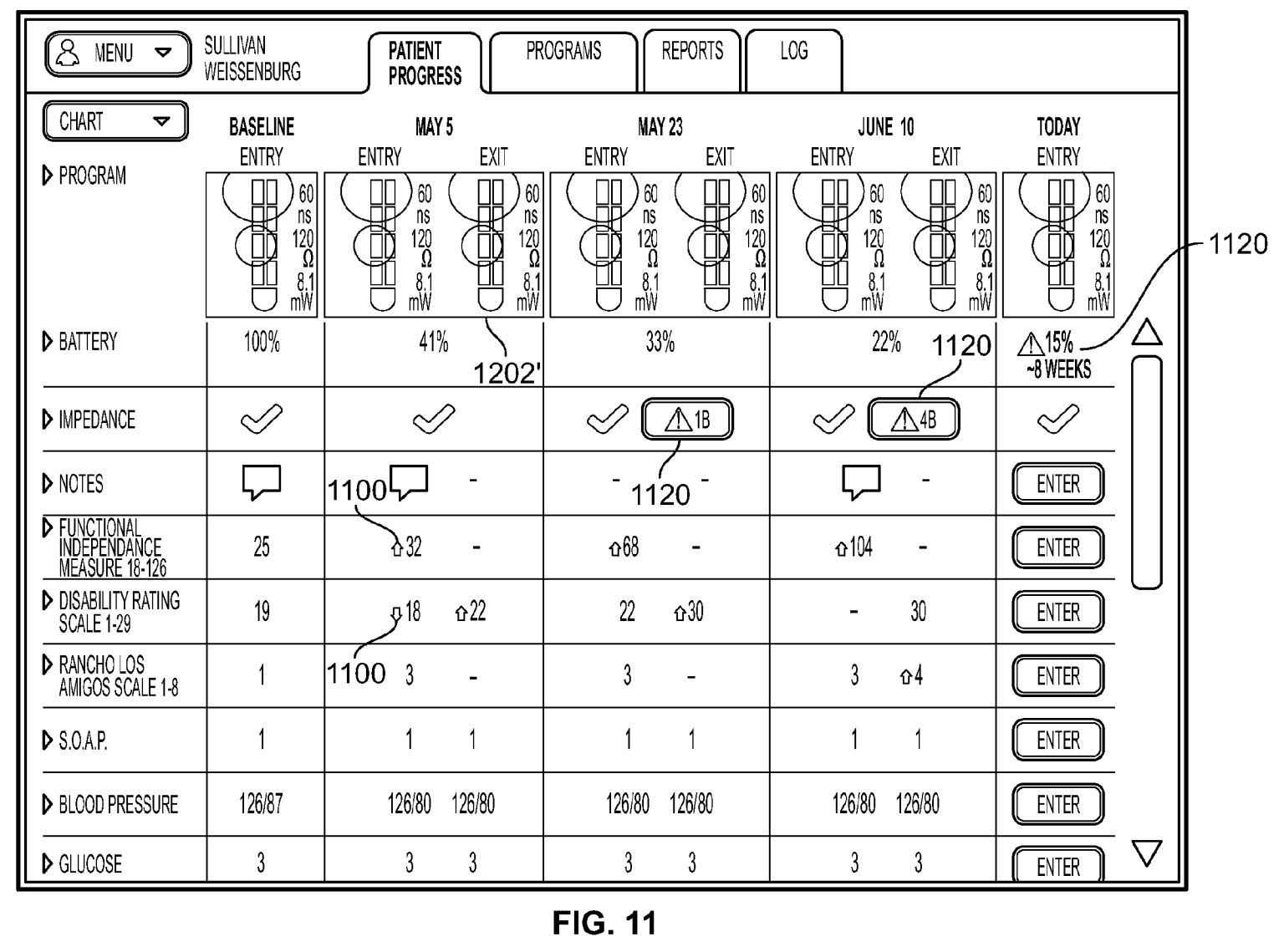
Figure 12:
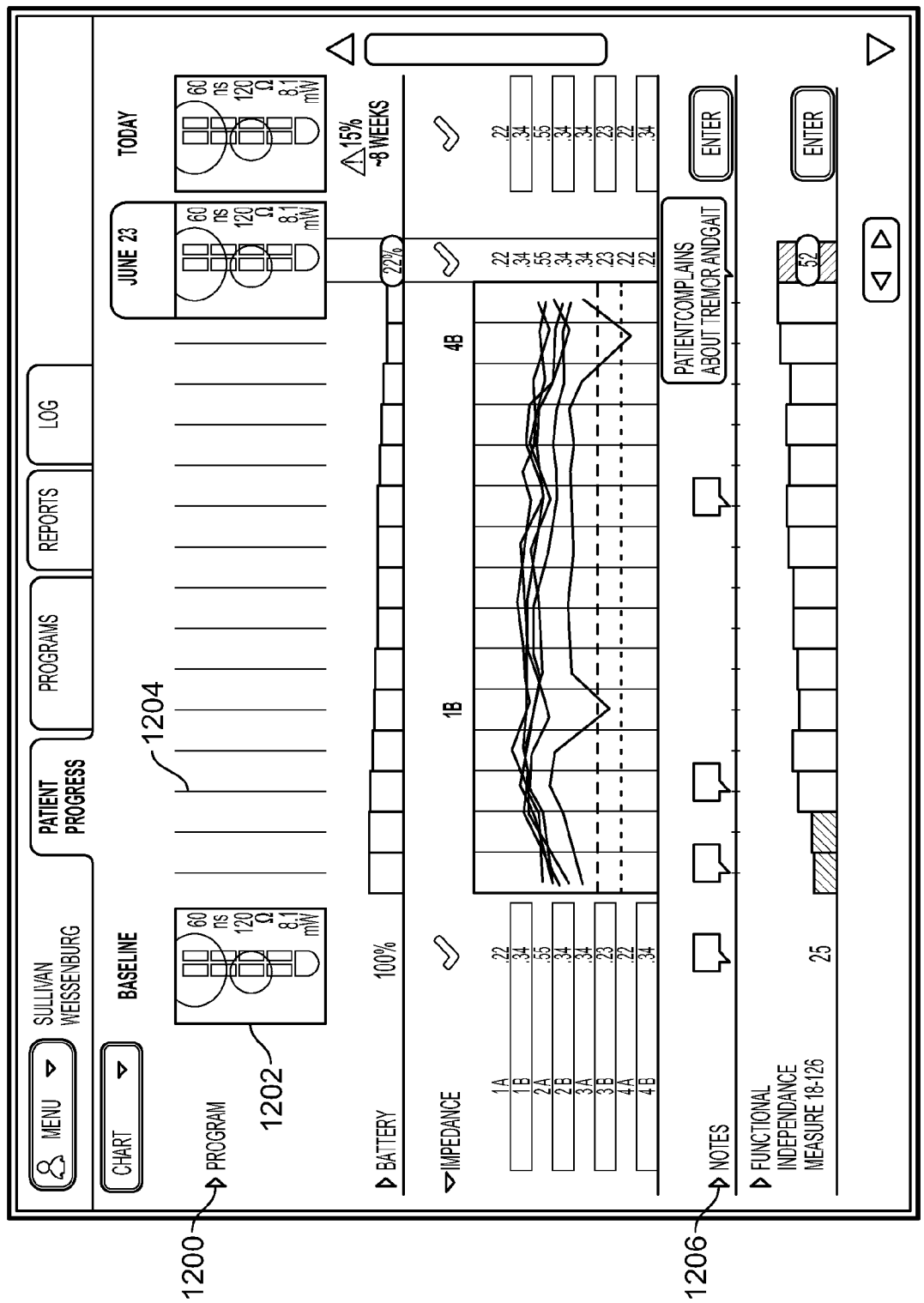

FIGS. 11-12 illustrate example screenshots of system output for patient history functions. For example, the information from each inquiry, such as the clinician programmer stimulation settings, can be displayed as a thumbnail view, such as the thumbnails 1202 shown in the "Program" timeline 1200 in FIG. 12. An inquiry or session may be that which is defined in memory as a session structure, e.g., a defined folder. In an example embodiment, therapeutic stimulation delivery may be conducted in sessions at a patient terminal. Information recorded during those sessions may be stored on a session basis. The stored sessions may be transmitted to a clinician programmer terminal at which the patient history functions may be performed using those received session data. Alternatively, sensors at the patient terminal may be time-stamp recorded data and the clinician programmer terminal may use the time-stamps to arrange the data in sessions. The patient terminal may be, for example, a portable terminal used by the patient on a daily basis. For example, the device may attachable to the patient's body. In addition, the various sensors may also be portable sensors, e.g., attached or attachable to the patient's body. Alternatively, the therapy delivery and the patient history functions may be performed at the same terminal.

In an example, the thumbnails may be provided such that, with scrolling along the Program timeline 1200, thumbnails may be removed from display when scrolled past an edge location of the timeline. In certain examples, with continued scrolling along the timeline 1200, the thumbnail may be re-displayed at an opposite edge of the screen, so that it appears to have been scrolled about the screen. In certain examples, certain ones of the thumbnails 1202 may be displayed to show its respective detailed information, while other are displayed as though rotated so that only a side-profile outline, shown as lines 1204 in FIG. 12, are displayed.

In certain examples, until a thumbnail representing an inquiry is selected, and not hidden or rotated, other information can be shown and tracked, e.g., in the form of various graphs of values against time, while the specific values from a specific inquiry are not shown. In an example, the thumbnails 1202 and corresponding detailed values of the first inquiry and/or the last inquiry can be shown by default, such as shown in FIG. 12. In an example embodiment, a dark highlight bar can be used to illustrate selection of a point along the timeline corresponding to a selected thumbnail, such as shown in FIG. 12. In one example, the highlight bar may be moved across the timeline, as the user scrolls through the thumbnails.

In an example embodiment, the patient history application is configured to compare numerically and/or graphically historical metrics of a physiological parameter or other sensed or generated information for the patient (e.g., a simulated or actual VOA, etc.). The patient history application may allow a user to select one or more metrics (e.g., historical metrics) to track on a per-patient basis. For example, FIG. 12 shows graphs for impedance, battery life, and a functional impedance measure. The system tracking aspects enable a user to customize the metric to focus on the patient's therapy and symptoms or other indications. In an example embodiment, the system may store groups of suggested tracking aspects on a per therapy or symptom basis, selectable as a whole by a user. In certain examples, the one or more metrics can be individually selectable and/or created by the user as the user sees fit.

The historical metric can be selected to display information from one or more previous sessions (e.g., the previous 3 sessions, the first and the last session, etc.). In an example, the system is configured to provide for comparison of one or more previous session information to a baseline or for the information to otherwise be displayed over several months or years, or through the timeline of the one or more selected sessions. For example, a baseline thumbnail may be continuously displayed, even as the user scrolls through the Program timeline to display different ones of the thumbnails corresponding to prior sessions. Further, the patient history application allows the user to zoom in on a specific day or other time period (e.g., days, hours, etc.) in conjunction with, or separate from viewing the longer timeline (e.g., the several months or years, or through the timeline of the one or more selected sessions). For example, an initial timeline representing a first time period may be replaced by another timeline representing a shorter or longer time period depending on whether the user as zoomed in or out.

In an example, the system is configured to output an alert when one or more parameters are out of a normal or otherwise defined specification, threshold, or boundary of the therapy or system. For example, the system may store information regarding ranges of normal or desired/required values for various parameters for comparison to actual values. FIG. 11, for example, shows displayed alerts 1120. In one example, the stored values may vary depending, e.g., on a particular therapy, symptoms, and/or patient. In an example, the alert is configurable to graphically display negative trends or times while the one or more parameters are out of the normal or otherwise defined specification, threshold, or boundary of the therapy or system.

In an example, the patient history application includes a comparison feature that allows the user to quickly and accurately determine if the device and/or patient symptoms are changing over time (in either a positive or negative perspective). For example, any change in a positive or negative direction for a value of one or more parameters may be flagged, even if not out of a tolerance range. For example, FIG. 11 shows arrows 1100 showing used for flagging such changes.

In an example, one or more metrics can include physiological information, device information, and/or one or more other types or categories of information, such as a stimulation setting or parameter, etc. The one or more metrics can be displayed graphically or otherwise presented to a user, such as is shown in FIG. 12. Further, notes can be input, received, or stored, such as shown in FIG. 12, e.g., in a timeline 1206 corresponding to the displayed thumbnails.

In an example embodiment of the present invention, thumbnails may be displayed in date order, without a timeline, i.e., without an indicator scaled to time, e.g., as shown in FIG. 11. As further shown in FIG. 11, a thumbnail 1202' may further include details regarding a beginning (entry) of a session and an end (exit) of the session.

Population Repository

In an example embodiment of the present invention, results of a patient therapy are transferred to a remote repository, e.g., a remote programmer system or a remote database, such as through a network or other communication method. In certain examples, the patient's results, as well as the results of one or more other patients, are collected, stored, or analyzed using the remote programmer system or the remote database, for example, to create patient population information. In certain examples, the population information can be used to update or otherwise program the clinician programmer system. For example, the information can be used for populating a library of VOAs and corresponding parameters, and/or for generating brain atlases.

Additional Notes

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

What is claimed is:

1. A method of a stimulation parameter selection machine, the method comprising:
   displaying, by a processor of the machine, via a display device, and in relation to a displayed model of a leadwire, an initial current field corresponding to a first stimulation parameter set;
   in response to user input, shifting, by the processor, the display of the current field with respect to the displayed leadwire model;
   determining, by the processor, a second stimulation parameter set that results in the shifted current field; and
   at least one of (a) outputting the second stimulation parameter set, and (b) setting a stimulation device with the second stimulation parameter set, the stimulation device configured for performing a stimulation (1) using a leadwire modeled by the leadwire model and (2) in accordance with the second stimulation parameter set;
   wherein:
      the user input is via hitting one or more displayed components of a user interface;
      the displayed components include a first set of directional buttons that each corresponds to a respective axial direction and for each of which the processor is configured to interpret hitting of the respective button as an instruction to shift the displayed current field in the respective axial direction to which the respective directional button corresponds; and
      at least one of:
         the displayed components further include a rotational directional button, hitting of which the processor is configured to interpret as an instruction for a gradual shift of the displayed current field rotationally about a central axis; and
         the first set of directional buttons includes a button, a hit of which the processor is configured to interpret as an instruction to shift the displayed current field from a first location to a second location that mirrors the first location about a predetermined axis.

2. The method of claim 1, further comprising:
   calculating, by the processor, a first volume of activation (VOA) for the first stimulation parameter set;
   displaying, by the processor and in the display device, the first VOA in relation to anatomical structures of a patient; and
   responsive to the user input:
      calculating, by the processor, a second VOA for the second stimulation parameter set; and
      displaying the second VOA in place of the first VOA relative to the anatomical structures of the patient and in a separate section of a same user interface display arrangement in which the shifted current field is displayed.

3. The method of claim 2, wherein the second VOA is displayed simultaneously with the display of the shifted current field.

4. The method of claim 1, wherein the leadwire model includes model electrodes, and each of the model electrodes is separately selectable for cycling through a plurality of options associable with the respective electrode, the set of options including off, active cathode, and active anode.

5. The method of claim 1, wherein the leadwire model includes model electrodes, and user interface, via interaction with which to receive the user input, includes for each of active ones of the model electrodes a respective directional selection component, selectable for increasing and decreasing stimulation amplitude associated with the respective electrode.

6. The method of claim 1, wherein the first set of directional buttons includes a pair of oppositely oriented directional buttons, and the user interface in which the first set of directional buttons is displayed also displays the current field.

7. The method of claim 1, wherein the user interface further includes a component for receipt of input for rotating a view of the displayed leadwire model and current field about a longitudinal central axis of the leadwire model.

8. The method of claim 7, wherein the display of the leadwire model and current field includes at least a first view showing the leadwire model along a length of the leadwire model and a second view showing at least one of a cross-section of the leadwire model and a view of the leadwire model orthogonal to a longitudinal axis of the leadwire model.

9. The method of claim 1, wherein:
   the current field resides in a defined cubed area; and
   the user interface, via interaction with which the user input is received, includes at least one of (a) a first set of eight input components for shifting the current field towards any of eight points of the cubed area, (b) a second set of six input components for shifting the current field towards centers of any of six planes defined by the cubed area, and (c) a third set of twelve input components for shifting the current field towards centers of any of twelve edges defined by the cubed area.

10. The method of claim 9, wherein the user interface includes the first, second, and third sets of input components.

11. The method of claim 1, wherein, for each of at least one of the first set of directional buttons, each hit of the respective button is interpreted as an instruction to shift the displayed current field orthogonally to a longitudinal axis of the leadwire model.

12. The method of claim 1, wherein, for each of at least one of the first set of directional buttons, each hit of the respective button is interpreted as an instruction to shift the displayed current field parallel to a longitudinal axis of the leadwire model.

13. The method of claim 1, wherein a center point of the current field is shifted in response to the user input via the selection of the component.

14. The method of claim 1, wherein the performance of the stimulation using the leadwire in accordance with the second stimulation parameter set is estimated by the processor to produce the shifted current field, which shifted current field is further estimated by the processor to result in a corresponding volume of activated tissue, the volume being different than the shifted current field.

15. The method of claim 14, further comprising displaying, by the processor the estimated volume of activated tissue.

16. The method of claim 15, wherein the display of the estimated volume of activated tissue is provided in a same display window as, and concurrently with, the display of the shifted current field.

17. The method of claim 1, wherein the displayed components include the rotational directional button.

18. The method of claim 1, wherein the first set of directional buttons includes the button, the hit of which the processor is configured to interpret as the instruction to shift the displayed current field from the first location to the second location that mirrors the first location about the predetermined axis.

19. A method of a stimulation parameter selection machine, the method comprising:
  calculating, by a processor of the machine, an initial current field for a first stimulation parameter set, wherein the calculation is dependent upon a leadwire to which the first stimulation parameter set is to be applied;
  displaying, by the processor and via a display device, the initial current field in relation to a displayed model of the leadwire; and
  in response to user input, shifting, by the processor, the display of the current field with respect to the displayed leadwire model;
  wherein:
    the user input is via hitting one or more displayed components of a user interface;
    the displayed components include a first set of directional buttons that each corresponds to a respective axial direction and for each of which the processor is configured to interpret hitting of the respective button as an instruction to shift the displayed current field in the respective axial direction to which the respective directional button corresponds; and
    at least one of:
      the displayed components further include a rotational directional button, hitting of which the processor is configured to interpret as an instruction for a gradual shift of the displayed current field rotationally about a central axis; and
      the first set of directional buttons includes a button, a hit of which the processor is configured to interpret as an instruction to shift the displayed current field from a first location to a second location that mirrors the first location about a predetermined axis.

20. The method of claim 19, wherein, for each of at least one of the first set of directional buttons, each hit of the respective button is interpreted as an instruction to shift the displayed current field orthogonally to a longitudinal axis of the leadwire model.

21. The method of claim 19, wherein, for each of at least one of the first set of directional buttons, each hit of the respective button is interpreted as an instruction to shift the displayed current field parallel to a longitudinal axis of the leadwire model.

22. A stimulation parameter selection system, comprising:
  a display device; and
  a processor configured to:
    display via the display device and in relation to a displayed model of a leadwire, an initial current field corresponding to a first stimulation parameter set;
    in response to user input, shift, the display of the current field with respect to the displayed leadwire model;
    determine a second stimulation parameter set that results in the shifted current field; and
    at least one of (a) output the second stimulation parameter set, and (b) set a stimulation device with the second stimulation parameter set, the stimulation device configured for performing a stimulation (1) using a leadwire modeled by the leadwire model and (2) in accordance with the second stimulation parameter set;
  wherein:
    the user input is via hitting one or more displayed components of a user interface;
    the displayed components include a first set of directional buttons that each corresponds to a respective axial direction and for each of which the processor is configured to interpret hitting of the respective button as an instruction to shift the displayed current field in the respective axial direction to which the respective directional button corresponds; and
    at least one of:
      the displayed components further include a rotational directional button, hitting of which the processor is configured to interpret as an instruction for a gradual shift of the displayed current field rotationally about a central axis; and
      the first set of directional buttons includes a button, a hit of which the processor is configured to interpret as an instruction to shift the displayed current field from a first location to a second location that mirrors the first location about a predetermined axis.

23. The system of claim 22, wherein, for each of at least one of the first set of directional buttons, each hit of the respective button is interpreted as an instruction to shift the displayed current field orthogonally to a longitudinal axis of the leadwire model.

24. The system of claim 22, wherein, for each of at least one of the first set of directional buttons, each hit of the respective button is interpreted as an instruction to shift the displayed current field parallel to a longitudinal axis of the leadwire model.

25. A method of a stimulation parameter selection machine, the method comprising:
  displaying, by a processor of the machine, via a display device, in relation to a displayed model of a leadwire, and in a first position, an initial current field corresponding to a first stimulation parameter set;
  in response to user input, shifting, by the processor, the display of the current field with respect to the displayed leadwire model;
  determining, by the processor, a second stimulation parameter set that results in the shifted current field; and
  at least one of (a) outputting the second stimulation parameter set, and (b) setting a stimulation device with the second stimulation parameter set, the stimulation device configured for performing a stimulation (1) using a leadwire modeled by the leadwire model and (2) in accordance with the second stimulation parameter set;
  wherein, a user interface, via interaction with which the user input is received, displays a grid of nodes three-dimensionally arranged about the displayed initial current field, each of the nodes being selectable, the processor being configured, for each of the nodes, to respond to a selection of the respective node by shifting the initial current field from the first position towards the selected node.

\* \* \* \* \*